US012566113B2

(12) United States Patent
Delaney et al.

(10) Patent No.: US 12,566,113 B2
(45) Date of Patent: Mar. 3, 2026

(54) REVERSIBLE FIXING REAGENTS AND METHODS OF USE THEREOF

(71) Applicant: 10x Genomics, Inc., Pleasanton, CA (US)

(72) Inventors: Joshua Delaney, Pleasanton, CA (US); Shalini Gohil, Pleasanton, CA (US); Adam Lowe, Pleasanton, CA (US); Yi Luo, Pleasanton, CA (US); Dagmar Walter, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 719 days.

(21) Appl. No.: 17/845,331

(22) Filed: Jun. 21, 2022

(65) Prior Publication Data

US 2022/0334031 A1 Oct. 20, 2022

Related U.S. Application Data

(63) Continuation of application No. PCT/US2020/066705, filed on Dec. 22, 2020.

(60) Provisional application No. 62/952,677, filed on Dec. 23, 2019, provisional application No. 63/026,513, filed on May 18, 2020.

(51) Int. Cl.

*G01N 1/30* (2006.01)
*C07D 403/12* (2006.01)

(52) U.S. Cl.

CPC ............. *G01N 1/30* (2013.01); *C07D 403/12* (2013.01); *G01N 2001/305* (2013.01)

(58) Field of Classification Search

CPC ... C07D 403/12; G01N 1/30; G01N 2001/305
See application file for complete search history.

(56) References Cited

U.S. PATENT DOCUMENTS

| | | | |
|---|---|---|---|
| 4,683,195 | A | 7/1987 | Mullis |
| 4,683,202 | A | 7/1987 | Mullis |
| 4,800,159 | A | 1/1989 | Mullis |
| 4,883,867 | A | 11/1989 | Lee |
| 4,965,188 | A | 10/1990 | Mullis |
| 4,988,617 | A | 1/1991 | Landegren et al. |
| 5,002,882 | A | 3/1991 | Lunnen |
| 5,130,238 | A | 7/1992 | Malek |
| 5,308,751 | A | 5/1994 | Ohkawa |
| 5,321,130 | A | 6/1994 | Yue |
| 5,410,030 | A | 4/1995 | Yue |
| 5,436,134 | A | 7/1995 | Haugland |
| 5,455,166 | A | 10/1995 | Walker |
| 5,494,810 | A | 2/1996 | Barany et al. |
| 5,503,980 | A | 4/1996 | Cantor |
| 5,512,439 | A | 4/1996 | Hornes |
| 5,512,462 | A | 4/1996 | Cheng |
| 5,582,977 | A | 12/1996 | Yue |
| 5,599,675 | A | 2/1997 | Brenner |
| 5,641,658 | A | 6/1997 | Adams |
| 5,648,245 | A | 7/1997 | Fire et al. |
| 5,658,751 | A | 8/1997 | Yue |
| 5,695,940 | A | 12/1997 | Drmanac et al. |
| 5,750,341 | A | 5/1998 | Macevicz |
| 5,752,982 | A | 5/1998 | Lang et al. |
| 5,763,175 | A | 6/1998 | Brenner |
| 5,830,711 | A | 11/1998 | Barany et al. |
| 5,837,832 | A | 11/1998 | Chee et al. |
| 5,854,033 | A | 12/1998 | Lizardi |
| 5,863,753 | A | 1/1999 | Haugland |
| 5,871,921 | A | 2/1999 | Landegren et al. |
| 5,912,148 | A | 6/1999 | Eggerding |
| 5,925,545 | A | 7/1999 | Reznikoff et al. |
| 5,928,906 | A | 7/1999 | Koester et al. |
| 5,958,775 | A | 9/1999 | Wickstrrom |
| 5,962,271 | A | 10/1999 | Chenchik et al. |
| 5,962,272 | A | 10/1999 | Chenchik et al. |
| 5,965,443 | A | 10/1999 | Reznikoff et al. |
| 6,013,440 | A | 1/2000 | Lipshutz |
| 6,027,889 | A | 2/2000 | Barany et al. |
| 6,054,274 | A | 4/2000 | Sampson et al. |
| 6,060,240 | A | 5/2000 | Kamb et al. |
| 6,130,073 | A | 10/2000 | Eggerding |
| 6,143,496 | A | 11/2000 | Brown |
| 6,153,389 | A | 11/2000 | Haarer |
| 6,159,736 | A | 12/2000 | Reznikoff et al. |
| 6,165,714 | A | 12/2000 | Lane et al. |
| 6,210,891 | B1 | 4/2001 | Nyren |
| 6,210,894 | B1 | 4/2001 | Brennan |
| 6,214,587 | B1 | 4/2001 | Dattagupta |
| 6,251,639 | B1 | 6/2001 | Kurn |
| 6,258,568 | B1 | 7/2001 | Nyren |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Gruttadauria et al., "Supported proline and proline-derivatives as recyclable organocatalysts," Chemical Society Reviews, Aug. 1, 2008, 37(8):1666-1688.

Sun et al., "Joint single-cell multiomic analysis in Wnt3a induced asymmetric stem cell division," Nature Comm., Oct. 12, 2021, 12:5941, 19 pages.

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual," Affymetrix Part No. 90094 (Affymetrix, Santa Clara, Calif.), GeneChip, 2000, 104 pages.

(Continued)

*Primary Examiner* — Bruck Kifle
(74) *Attorney, Agent, or Firm* — Fish & Richardson P.C.

(57) ABSTRACT

The present disclosure relates to compositions and methods for reversible fixation of biological samples using fixation reagents that form bis-carbamate crosslinks between amine-bearing moieties in biomolecules.

12 Claims, 16 Drawing Sheets

(56) References Cited

U.S. PATENT DOCUMENTS

| | | | |
|---|---|---|---|
| 6,265,552 | B1 | 7/2001 | Schatz |
| 6,266,459 | B1 | 7/2001 | Walt |
| 6,268,148 | B1 | 7/2001 | Barany et al. |
| 6,274,320 | B1 | 8/2001 | Rothberg |
| 6,291,180 | B1 | 9/2001 | Chu |
| 6,291,187 | B1 | 9/2001 | Kingsmore et al. |
| 6,300,063 | B1 | 10/2001 | Lipshutz et al. |
| 6,309,824 | B1 | 10/2001 | Drmanac |
| 6,323,009 | B1 | 11/2001 | Lasken et al. |
| 6,344,316 | B1 | 2/2002 | Lockhart |
| 6,344,329 | B1 | 2/2002 | Lizardi et al. |
| 6,355,431 | B1 | 3/2002 | Chee |
| 6,368,801 | B1 | 4/2002 | Faruqi |
| 6,401,267 | B1 | 6/2002 | Drmanac |
| 6,404,907 | B1 | 6/2002 | Gilchrist |
| 6,432,360 | B1 | 8/2002 | Church et al. |
| 6,503,713 | B1 | 1/2003 | Rana |
| 6,506,561 | B1 | 1/2003 | Cheval et al. |
| 6,534,266 | B1 | 3/2003 | Singer |
| 6,544,732 | B1 | 4/2003 | Chee |
| 6,573,043 | B1 | 6/2003 | Cohen et al. |
| 6,579,695 | B1 | 6/2003 | Lambalot |
| 6,620,584 | B1 | 9/2003 | Chee |
| 6,632,641 | B1 | 10/2003 | Brennan |
| 6,737,236 | B1 | 5/2004 | Pieken et al. |
| 6,770,441 | B2 | 8/2004 | Dickinson |
| 6,773,886 | B2 | 8/2004 | Kaufman |
| 6,787,308 | B2 | 9/2004 | Balasubramanian |
| 6,797,470 | B2 | 9/2004 | Barany et al. |
| 6,800,453 | B2 | 10/2004 | Labaer |
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,852,487 | B1 | 2/2005 | Barany et al. |
| 6,859,570 | B2 | 2/2005 | Walt |
| 6,864,052 | B1 | 3/2005 | Drmanac |
| 6,867,028 | B2 | 3/2005 | Janulaitis |
| 6,872,816 | B1 | 3/2005 | Hall et al. |
| 6,875,572 | B2 | 4/2005 | Prudent et al. |
| 6,890,741 | B2 | 5/2005 | Fan et al. |
| 6,897,023 | B2 | 5/2005 | Fu |
| 6,913,881 | B1 | 7/2005 | Aizenstein et al. |
| 6,942,968 | B1 | 9/2005 | Dickinson et al. |
| 7,011,944 | B2 | 3/2006 | Prudent et al. |
| 7,057,026 | B2 | 6/2006 | Barnes |
| 7,083,980 | B2 | 8/2006 | Reznikoff et al. |
| 7,115,400 | B1 | 10/2006 | Adessi |
| 7,118,883 | B2 | 10/2006 | Inoue |
| 7,166,431 | B2 | 1/2007 | Chee et al. |
| 7,192,735 | B2 | 3/2007 | Lambalot |
| 7,211,414 | B2 | 5/2007 | Hardin |
| 7,255,994 | B2 | 8/2007 | Lao |
| 7,258,976 | B2 | 8/2007 | Mitsuhashi |
| 7,282,328 | B2 | 10/2007 | Kong et al. |
| 7,297,518 | B2 | 11/2007 | Quake |
| 7,329,492 | B2 | 2/2008 | Hardin |
| 7,358,047 | B2 | 4/2008 | Hafner et al. |
| 7,361,488 | B2 | 4/2008 | Fan et al. |
| 7,378,242 | B2 | 5/2008 | Hurt |
| 7,393,665 | B2 | 7/2008 | Brenner |
| 7,405,281 | B2 | 7/2008 | Xu |
| 7,407,757 | B2 | 8/2008 | Brenner |
| 7,473,767 | B2 | 1/2009 | Dimitrov |
| 7,499,806 | B2 | 3/2009 | Kermani et al. |
| 7,537,897 | B2 | 5/2009 | Brenner |
| 7,563,576 | B2 | 7/2009 | Chee |
| 7,579,153 | B2 | 8/2009 | Brenner |
| 7,582,420 | B2 | 9/2009 | Oliphant et al. |
| 7,601,498 | B2 | 10/2009 | Mao |
| 7,608,434 | B2 | 10/2009 | Reznikoff et al. |
| 7,611,869 | B2 | 11/2009 | Fan |
| 7,635,566 | B2 | 12/2009 | Brenner |
| 7,666,612 | B2 | 2/2010 | Johnsson |
| 7,674,752 | B2 | 3/2010 | He |
| 7,709,198 | B2 | 5/2010 | Luo et al. |
| 7,776,547 | B2 | 8/2010 | Roth |
| 7,776,567 | B2 | 8/2010 | Mao |
| 7,803,943 | B2 | 9/2010 | Mao |
| 7,888,009 | B2 | 2/2011 | Barany et al. |
| 7,892,747 | B2 | 2/2011 | Barany et al. |
| 7,910,304 | B2 | 3/2011 | Drmanac |
| 7,914,981 | B2 | 3/2011 | Barany et al. |
| 7,955,794 | B2 | 6/2011 | Shen et al. |
| 7,960,119 | B2 | 6/2011 | Chee |
| 7,985,565 | B2 | 7/2011 | Mayer et al. |
| 8,003,354 | B2 | 8/2011 | Shen et al. |
| 8,076,063 | B2 | 12/2011 | Fan |
| 8,092,784 | B2 | 1/2012 | Mao |
| 8,148,068 | B2 | 4/2012 | Brenner |
| 8,206,917 | B2 | 6/2012 | Chee |
| 8,268,554 | B2 | 9/2012 | Schallmeiner |
| 8,288,103 | B2 | 10/2012 | Oliphant |
| 8,288,122 | B2 | 10/2012 | O'Leary et al. |
| 8,343,500 | B2 | 1/2013 | Wraith |
| 8,383,338 | B2 | 2/2013 | Kitzman |
| 8,431,691 | B2 | 4/2013 | McKernan et al. |
| 8,460,865 | B2 | 6/2013 | Chee |
| 8,481,257 | B2 | 7/2013 | Van Eijk |
| 8,481,258 | B2 | 7/2013 | Church et al. |
| 8,481,292 | B2 | 7/2013 | Casbon |
| 8,481,698 | B2 | 7/2013 | Lieberman et al. |
| 8,507,204 | B2 | 8/2013 | Pierce et al. |
| 8,519,115 | B2 | 8/2013 | Webster et al. |
| 8,551,710 | B2 | 10/2013 | Bernitz et al. |
| 8,568,979 | B2 | 10/2013 | Stuelpnagel et al. |
| 8,586,310 | B2 | 11/2013 | Mitra |
| 8,597,891 | B2 | 12/2013 | Barany et al. |
| 8,603,743 | B2 | 12/2013 | Liu et al. |
| 8,604,182 | B2 | 12/2013 | Luo et al. |
| 8,614,073 | B2 | 12/2013 | Van Eijk |
| 8,624,016 | B2 | 1/2014 | Barany et al. |
| 8,685,889 | B2 | 4/2014 | Van Eijk |
| 8,741,564 | B2 | 6/2014 | Seligmann |
| 8,741,606 | B2 | 6/2014 | Casbon |
| 8,771,950 | B2 | 7/2014 | Church et al. |
| 8,785,353 | B2 | 7/2014 | Van Eijk |
| 8,790,873 | B2 | 7/2014 | Namsaraev et al. |
| 8,809,238 | B2 | 8/2014 | Livak et al. |
| 8,815,512 | B2 | 8/2014 | Van Eijk |
| 8,835,358 | B2 | 9/2014 | Fodor |
| 8,865,410 | B2 | 10/2014 | Shendure |
| 8,906,626 | B2 | 12/2014 | Oliphant et al. |
| 8,911,945 | B2 | 12/2014 | Van Eijk |
| 8,936,912 | B2 | 1/2015 | Mitra |
| 8,951,726 | B2 | 2/2015 | Luo et al. |
| 8,951,728 | B2 | 2/2015 | Rasmussen |
| 8,986,926 | B2 | 3/2015 | Ferree et al. |
| 9,005,891 | B2 | 4/2015 | Sinicropi et al. |
| 9,005,935 | B2 | 4/2015 | Belyaev |
| 9,023,768 | B2 | 5/2015 | Van Eijk |
| 9,062,348 | B1 | 6/2015 | Van Eijk |
| 9,080,210 | B2 | 7/2015 | Van Eijk |
| 9,194,001 | B2 | 11/2015 | Brenner |
| 9,201,063 | B2 | 12/2015 | Sood et al. |
| 9,273,349 | B2 | 3/2016 | Nguyen et al. |
| 9,290,808 | B2 | 3/2016 | Fodor |
| 9,290,809 | B2 | 3/2016 | Fodor |
| 9,328,383 | B2 | 5/2016 | Van Eijk |
| 9,334,536 | B2 | 5/2016 | Van Eijk |
| 9,371,563 | B2 | 6/2016 | Geiss et al. |
| 9,371,598 | B2 | 6/2016 | Chee |
| 9,376,716 | B2 | 6/2016 | Van Eijk |
| 9,376,717 | B2 | 6/2016 | Gao et al. |
| 9,376,719 | B2 | 6/2016 | Eijk |
| 9,404,156 | B2 | 8/2016 | Hicks |
| 9,416,409 | B2 | 8/2016 | Hayden |
| 9,447,459 | B2 | 9/2016 | Van Eijk |
| 9,453,256 | B2 | 9/2016 | Van Eijk |
| 9,493,820 | B2 | 11/2016 | Van Eijk |
| 9,506,061 | B2 | 11/2016 | Brown et al. |
| 9,512,422 | B2 | 12/2016 | Barnard et al. |
| 9,574,230 | B2 | 2/2017 | Van Eijk |
| 9,593,365 | B2 | 3/2017 | Frisen et al. |
| 9,598,728 | B2 | 3/2017 | Barany et al. |

(56) References Cited

U.S. PATENT DOCUMENTS 9,624,538 B2 4/2017 Church et al.
9,644,204 B2 5/2017 Hindson et al.
9,657,335 B2 5/2017 Van Eijk
9,670,542 B2 6/2017 Eijk
9,694,361 B2 7/2017 Bharadwaj
9,702,004 B2 7/2017 Van Eijk
9,714,446 B2 7/2017 Webster et al.
9,714,937 B2 7/2017 Dunaway
9,727,810 B2 8/2017 Fodor et al.
9,745,627 B2 8/2017 Van Eijk
9,777,324 B2 10/2017 Van Eijk
9,783,841 B2 10/2017 Nolan et al.
9,790,476 B2 10/2017 Gloeckner et al.
9,816,134 B2 11/2017 Namsaraev
9,834,814 B2 12/2017 Peter et al.
9,850,536 B2 12/2017 Oliphant et al.
9,856,521 B2 1/2018 Stevens et al.
9,868,979 B2 1/2018 Chee et al.
9,879,313 B2 1/2018 Chee et al.
9,896,721 B2 2/2018 Van Eijk
9,898,576 B2 2/2018 Van Eijk
9,898,577 B2 2/2018 Van Eijk
9,902,950 B2 2/2018 Church et al.
9,902,991 B2 2/2018 Sinicropi et al.
9,909,167 B2 3/2018 Samusik et al.
9,938,566 B2 4/2018 Shepard et al.
9,957,550 B2 5/2018 Yeakley et al.
9,975,122 B2 5/2018 Masquelier et al.
10,002,316 B2 6/2018 Fodor et al.
10,011,872 B1 7/2018 Belgrader et al.
10,023,907 B2 7/2018 Van Eijk
10,030,261 B2 7/2018 Frisen et al.
10,035,992 B2 7/2018 Gloeckner et al.
10,041,949 B2 8/2018 Bendall et al.
10,053,723 B2 8/2018 Hindson et al.
10,059,989 B2 8/2018 Giresi et al.
10,059,990 B2 8/2018 Boyden et al.
10,071,377 B2 9/2018 Bharadwaj et al.
10,095,832 B2 10/2018 Van Eijk
10,144,966 B2 12/2018 Cantor
10,208,982 B2 2/2019 Bannish et al.
10,227,639 B2 3/2019 Levner et al.
10,266,876 B2 4/2019 Cai et al.
10,267,808 B2 4/2019 Cai
10,273,541 B2 4/2019 Hindson et al.
10,308,982 B2 6/2019 Chee
10,357,771 B2 7/2019 Bharadwaj
10,370,698 B2 8/2019 Nolan et al.
10,415,080 B2 9/2019 Dunaway et al.
10,428,326 B2 10/2019 Belhocine et al.
10,465,235 B2 11/2019 Gullberg et al.
10,472,669 B2 11/2019 Chee
10,480,022 B2 11/2019 Chee
10,480,029 B2 11/2019 Bent et al.
10,494,667 B2 12/2019 Chee
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,544,403 B2 1/2020 Gloeckner et al.
10,550,429 B2 2/2020 Harada et al.
10,590,244 B2 3/2020 Delaney et al.
10,633,648 B2 4/2020 Seelig et al.
10,640,816 B2 5/2020 Beechem et al.
10,640,826 B2 5/2020 Church et al.
10,662,468 B2 5/2020 Chee
10,669,569 B2 6/2020 Gullberg et al.
10,724,078 B2 7/2020 Van Driel et al.
10,725,027 B2 7/2020 Bell
10,774,372 B2 9/2020 Chee et al.
10,774,374 B2 9/2020 Frisen et al.
10,787,701 B2 9/2020 Chee
10,815,519 B2 10/2020 Husain et al.
10,829,803 B2 11/2020 Terbrueggen et al.
10,844,426 B2 11/2020 Daugharthy et al.
10,858,698 B2 12/2020 Church et al.
10,858,702 B2 12/2020 Lucero et al.
10,872,679 B2 12/2020 Cai et al.
10,913,975 B2 2/2021 So et al.
10,914,730 B2 2/2021 Chee et al.
10,927,403 B2 2/2021 Chee et al.
10,961,566 B2 3/2021 Chee
11,001,879 B1 5/2021 Chee
11,008,607 B2 5/2021 Chee
11,008,608 B2 5/2021 Samusik et al.
11,046,996 B1 6/2021 Chee et al.
11,067,567 B2 7/2021 Chee
11,104,936 B2 8/2021 Zhang et al.
11,118,216 B2 9/2021 Koshinsky et al.
11,156,603 B2 10/2021 Chee
11,162,132 B2 11/2021 Frisen et al.
11,208,684 B2 12/2021 Chee
11,214,796 B2 1/2022 Shirai et al.
11,286,515 B2 3/2022 Chee et al.
11,293,917 B2 4/2022 Chee
11,299,774 B2 4/2022 Frisen et al.
11,313,856 B2 4/2022 Chee
11,332,790 B2 5/2022 Chell et al.
11,352,659 B2 6/2022 Frisen et al.
11,352,667 B2 6/2022 Hauling et al.
11,359,228 B2 6/2022 Chee et al.
11,365,442 B2 6/2022 Chee
11,371,086 B2 6/2022 Chee
11,384,386 B2 7/2022 Chee
11,390,912 B2 7/2022 Frisen et al.
11,401,545 B2 8/2022 Chee
11,407,992 B2 8/2022 Dadhwal
11,408,029 B2 8/2022 Katiraee et al.
11,434,524 B2 9/2022 Ramachandran Iyer et al.
11,459,607 B1 10/2022 Terry et al.
11,479,809 B2 10/2022 Frisen et al.
11,479,810 B1 10/2022 Chee
11,492,612 B1 11/2022 Dadhwal
11,501,440 B2 11/2022 Weisenfeld et al.
11,505,828 B2 11/2022 Chell et al.
11,512,308 B2 11/2022 Gallant et al.
11,519,022 B2 12/2022 Chee
11,519,033 B2 12/2022 Schnall-Levin et al.
11,530,438 B2 12/2022 Persson et al.
11,535,887 B2 12/2022 Gallant et al.
11,542,543 B2 1/2023 Chee
11,549,138 B2 1/2023 Chee
11,560,587 B2 1/2023 Chee
11,560,592 B2 1/2023 Chew et al.
11,560,593 B2 1/2023 Chell et al.
11,592,447 B2 2/2023 Uytingco et al.
11,608,498 B2 3/2023 Gallant et al.
11,608,520 B2 3/2023 Galonska et al.
11,613,773 B2 3/2023 Frisen et al.
11,618,897 B2 4/2023 Kim et al.
11,618,918 B2 4/2023 Chee et al.
11,624,063 B2 4/2023 Dadhwal
11,624,086 B2 4/2023 Uytingco et al.
11,634,756 B2 4/2023 Chee
11,649,485 B2 5/2023 Yin et al.
11,661,619 B2 5/2023 Paczkowski et al.
11,661,626 B2 5/2023 Katiraee et al.
11,680,260 B2 6/2023 Kim et al.
11,692,218 B2 7/2023 Engblom et al.
11,702,693 B2 7/2023 Bharadwaj
11,702,698 B2 7/2023 Stoeckius
11,713,480 B2 8/2023 Lee
11,732,292 B2 8/2023 Chee
11,732,299 B2 8/2023 Ramachandran Iyer
11,732,300 B2 8/2023 Bava
11,733,238 B2 8/2023 Chee
11,739,372 B2 8/2023 Frisen et al.
11,739,381 B2 8/2023 Chew et al.
11,753,673 B2 9/2023 Chew et al.
11,753,674 B2 9/2023 Chee et al.
11,753,675 B2 9/2023 Ramachandran Iyer
11,761,030 B2 9/2023 Chee
11,761,038 B1 9/2023 Stoeckius
11,767,550 B2 9/2023 Chee

(56) References Cited

U.S. PATENT DOCUMENTS

| | | | |
|---|---|---|---|
| 11,768,175 | B1 | 9/2023 | Kim et al. |
| 11,773,433 | B2 | 10/2023 | Gallant et al. |
| 11,781,130 | B2 | 10/2023 | Dadhwal |
| 11,788,122 | B2 | 10/2023 | Frisen et al. |
| 11,795,498 | B2 | 10/2023 | Frisen et al. |
| 11,795,507 | B2 | 10/2023 | Chell et al. |
| 11,808,769 | B2 | 11/2023 | Uytingco et al. |
| 11,821,024 | B2 | 11/2023 | Chee et al. |
| 11,821,035 | B1 | 11/2023 | Bent et al. |
| 11,827,935 | B1 | 11/2023 | Ramachandran Iyer et al. |
| 11,835,462 | B2 | 12/2023 | Bava |
| 11,840,687 | B2 | 12/2023 | Gallant et al. |
| 11,840,724 | B2 | 12/2023 | Chew et al. |
| 11,845,979 | B2 | 12/2023 | Engblom et al. |
| 11,859,178 | B2 | 1/2024 | Gallant et al. |
| 11,866,767 | B2 | 1/2024 | Uytingco et al. |
| 11,866,770 | B2 | 1/2024 | Chee |
| 11,873,482 | B2 | 1/2024 | Kim et al. |
| 11,891,654 | B2 | 2/2024 | Alvarado Martinez et al. |
| 11,898,205 | B2 | 2/2024 | Bava |
| 11,926,822 | B1 | 3/2024 | Gohil et al. |
| 11,926,863 | B1 | 3/2024 | Boutet |
| 11,926,867 | B2 | 3/2024 | Yin et al. |
| 11,933,957 | B1 | 3/2024 | Tentori et al. |
| 11,952,627 | B2 | 4/2024 | Stoeckius |
| 11,959,076 | B2 | 4/2024 | Kim et al. |
| 11,959,130 | B2 | 4/2024 | Galonska et al. |
| 11,965,213 | B2 | 4/2024 | Williams |
| 11,970,739 | B2 | 4/2024 | Chew et al. |
| 11,981,958 | B1 | 5/2024 | Galonska |
| 11,981,960 | B1 | 5/2024 | Lin et al. |
| 11,981,965 | B2 | 5/2024 | Chell et al. |
| RE50,065 | E | 7/2024 | Frisen et al. |
| 12,024,741 | B2 | 7/2024 | Tentori et al. |
| 12,031,177 | B1 | 7/2024 | Tentori et al. |
| 12,060,604 | B2 | 8/2024 | Katiraee et al. |
| 12,071,655 | B2 | 8/2024 | Sukovich et al. |
| 12,076,701 | B2 | 9/2024 | Bava |
| 12,098,417 | B2 | 9/2024 | Engblom et al. |
| 12,098,985 | B2 | 9/2024 | Cox et al. |
| 12,110,541 | B2 | 10/2024 | Bava |
| 12,117,439 | B2 | 10/2024 | Delaney et al. |
| 12,128,403 | B2 | 10/2024 | Kim et al. |
| 12,129,516 | B2 | 10/2024 | Tentori et al. |
| 12,157,124 | B2 | 12/2024 | Cox et al. |
| 12,180,543 | B2 | 12/2024 | Uytingco et al. |
| 12,195,790 | B2 | 1/2025 | Sukovich et al. |
| 12,203,134 | B2 | 1/2025 | Nagendran et al. |
| 12,209,280 | B1 | 1/2025 | Mignardi et al. |
| 12,223,751 | B2 | 2/2025 | Li et al. |
| 12,228,544 | B2 | 2/2025 | Kim et al. |
| 12,234,505 | B2 | 2/2025 | Chee |
| 12,241,060 | B2 | 3/2025 | Kim et al. |
| 12,241,890 | B2 | 3/2025 | Delaney et al. |
| 12,249,085 | B2 | 3/2025 | Tentori et al. |
| 12,265,079 | B1 | 4/2025 | Bent |
| 12,270,077 | B2 | 4/2025 | Schnall-Levin et al. |
| 12,275,988 | B2 | 4/2025 | Galonska et al. |
| 12,281,357 | B1 | 4/2025 | Tentori et al. |
| 12,286,673 | B2 | 4/2025 | Bava |
| 12,287,264 | B2 | 4/2025 | Cox et al. |
| 12,297,486 | B2 | 5/2025 | Patterson et al. |
| 12,297,487 | B2 | 5/2025 | Chee |
| 12,297,488 | B2 | 5/2025 | Chee |
| 12,344,892 | B2 | 7/2025 | Schnall-Levin et al. |
| 12,365,935 | B2 | 7/2025 | Chew et al. |
| 12,365,942 | B2 | 7/2025 | Stoeckius |
| 12,371,688 | B2 | 7/2025 | Kim et al. |
| 12,378,607 | B2 | 8/2025 | Schnall-Levin et al. |
| 12,385,083 | B2 | 8/2025 | Shah |
| 12,391,979 | B2 | 8/2025 | Chee |
| 12,391,980 | B2 | 8/2025 | Chee |
| 2001/0055764 | A1 | 12/2001 | Empendocles et al. |
| 2002/0040275 | A1 | 4/2002 | Cravatt |
| 2002/0051986 | A1 | 5/2002 | Baez et al. |
| 2002/0055100 | A1 | 5/2002 | Kawashima |
| 2002/0058250 | A1 | 5/2002 | Firth |
| 2002/0086441 | A1 | 7/2002 | Baranov et al. |
| 2002/0164611 | A1 | 11/2002 | Bamdad |
| 2003/0017451 | A1 | 1/2003 | Wang et al. |
| 2003/0022207 | A1 | 1/2003 | Balasubramanian |
| 2003/0064398 | A1 | 4/2003 | Barnes |
| 2003/0087232 | A1 | 5/2003 | Christians |
| 2003/0092624 | A1 | 5/2003 | Wang et al. |
| 2003/0138879 | A1 | 7/2003 | Lambalot |
| 2003/0148335 | A1 | 8/2003 | Shen et al. |
| 2003/0162216 | A1 | 8/2003 | Gold |
| 2003/0165948 | A1 | 9/2003 | Alsmadi et al. |
| 2003/0211489 | A1 | 11/2003 | Shen et al. |
| 2003/0224419 | A1 | 12/2003 | Corcoran |
| 2003/0232348 | A1 | 12/2003 | Jones et al. |
| 2003/0232382 | A1 | 12/2003 | Brennan |
| 2003/0235854 | A1 | 12/2003 | Chan et al. |
| 2004/0033499 | A1 | 2/2004 | Ilsley et al. |
| 2004/0067492 | A1 | 4/2004 | Peng et al. |
| 2004/0082059 | A1 | 4/2004 | Webb et al. |
| 2004/0096853 | A1 | 5/2004 | Mayer |
| 2004/0106110 | A1 | 6/2004 | Balasubramanian |
| 2004/0235103 | A1 | 11/2004 | Reznikoff et al. |
| 2004/0241660 | A1 | 12/2004 | Wojtowicz et al. |
| 2004/0248325 | A1 | 12/2004 | Bukusoglu et al. |
| 2004/0259105 | A1 | 12/2004 | Fan et al. |
| 2005/0003431 | A1 | 1/2005 | Wucherpfennig |
| 2005/0014203 | A1 | 1/2005 | Darfler et al. |
| 2005/0037393 | A1 | 2/2005 | Gunderson et al. |
| 2005/0048580 | A1 | 3/2005 | Labaer |
| 2005/0064460 | A1 | 3/2005 | Holliger et al. |
| 2005/0095627 | A1 | 5/2005 | Kolman et al. |
| 2005/0100900 | A1 | 5/2005 | Kawashima et al. |
| 2005/0118602 | A1 | 6/2005 | Li et al. |
| 2005/0130173 | A1 | 6/2005 | Leamon et al. |
| 2005/0136414 | A1 | 6/2005 | Gunderson et al. |
| 2005/0164292 | A1 | 7/2005 | Farooqui |
| 2005/0170373 | A1 | 8/2005 | Monforte |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0239119 | A1 | 10/2005 | Tsukada et al. |
| 2005/0260653 | A1 | 11/2005 | LaBaer |
| 2005/0266417 | A1 | 12/2005 | Barany et al. |
| 2006/0041385 | A1 | 2/2006 | Bauer et al. |
| 2006/0046313 | A1 | 3/2006 | Roth |
| 2006/0084078 | A1 | 4/2006 | Zhao |
| 2006/0105352 | A1 | 5/2006 | Qiao et al. |
| 2006/0154286 | A1 | 7/2006 | Kong et al. |
| 2006/0188901 | A1 | 8/2006 | Barnes et al. |
| 2006/0199183 | A1 | 9/2006 | Valat et al. |
| 2006/0211001 | A1 | 9/2006 | Yu et al. |
| 2006/0216775 | A1 | 9/2006 | Burkart et al. |
| 2006/0240439 | A1 | 10/2006 | Smith et al. |
| 2006/0263789 | A1 | 11/2006 | Kincaid |
| 2006/0275782 | A1 | 12/2006 | Gunderson et al. |
| 2006/0281109 | A1 | 12/2006 | Barr Ost et al. |
| 2007/0020640 | A1 | 1/2007 | McCloskey et al. |
| 2007/0020669 | A1 | 1/2007 | Ericsson |
| 2007/0026430 | A1 | 2/2007 | Andersen et al. |
| 2007/0054288 | A1 | 3/2007 | Su et al. |
| 2007/0087360 | A1 | 4/2007 | Boyd |
| 2007/0099208 | A1 | 5/2007 | Drmanac et al. |
| 2007/0128624 | A1 | 6/2007 | Gormley et al. |
| 2007/0128656 | A1 | 6/2007 | Agrawal |
| 2007/0134723 | A1 | 6/2007 | Kozlov et al. |
| 2007/0161020 | A1 | 7/2007 | Luo et al. |
| 2007/0166705 | A1 | 7/2007 | Milton et al. |
| 2007/0172873 | A1 | 7/2007 | Brenner et al. |
| 2007/0207482 | A1 | 9/2007 | Church et al. |
| 2007/0254305 | A1 | 11/2007 | Paik et al. |
| 2007/0269805 | A1 | 11/2007 | Hogers |
| 2008/0003586 | A1 | 1/2008 | Hyde et al. |
| 2008/0009420 | A1 | 1/2008 | Schroth et al. |
| 2008/0108082 | A1 | 5/2008 | Rank et al. |
| 2008/0108804 | A1 | 5/2008 | Hayashizaki et al. |
| 2008/0132429 | A1 | 6/2008 | Perov et al. |

(56) References Cited

U.S. PATENT DOCUMENTS

2008/0160580 A1 7/2008 Adessi et al.
2008/0220434 A1 9/2008 Thomas
2008/0261204 A1 10/2008 Lexow
2008/0286795 A1 11/2008 Kawashima et al.
2008/0293046 A1 11/2008 Allawi et al.
2009/0005252 A1 1/2009 Drmanac et al.
2009/0006002 A1 1/2009 Honisch et al.
2009/0011943 A1 1/2009 Drmanac et al.
2009/0018024 A1 1/2009 Church et al.
2009/0026082 A1 1/2009 Rothberg et al.
2009/0036323 A1 2/2009 van Eijk et al.
2009/0060866 A1 3/2009 Dousson et al.
2009/0082212 A1 3/2009 Williams
2009/0099041 A1 4/2009 Church et al.
2009/0105959 A1 4/2009 Braverman et al.
2009/0117573 A1 5/2009 Fu et al.
2009/0127589 A1 5/2009 Rothberg et al.
2009/0155781 A1 6/2009 Drmanac et al.
2009/0170713 A1 7/2009 van Eijk et al.
2009/0202998 A1 8/2009 Schlumpberger et al.
2009/0233802 A1 9/2009 Bignell et al.
2009/0253581 A1 10/2009 van Eijk et al.
2009/0270273 A1 10/2009 Burns et al.
2009/0283407 A1 11/2009 Van Eijk
2009/0286249 A1 11/2009 Becker et al.
2009/0289184 A1 11/2009 Deininger
2009/0291854 A1 11/2009 Weisinger-Mayr et al.
2009/0312193 A1 12/2009 Kim et al.
2010/0035249 A1 2/2010 Hayashizaki et al.
2010/0047790 A1 2/2010 Southern et al.
2010/0069263 A1 3/2010 Shendure et al.
2010/0105052 A1 4/2010 Drmanac et al.
2010/0105112 A1 4/2010 Heltze et al.
2010/0120097 A1 5/2010 Matz et al.
2010/0120098 A1 5/2010 Grunenwald et al.
2010/0129874 A1 5/2010 Mitra et al.
2010/0145037 A1 6/2010 Brive et al.
2010/0173384 A1 7/2010 Johnsson et al.
2010/0184618 A1 7/2010 Namsaraev et al.
2010/0210475 A1 8/2010 Lee et al.
2010/0227329 A1 9/2010 Cuppens
2010/0273219 A1 10/2010 May et al.
2011/0028685 A1 2/2011 Purkayastha et al.
2011/0033854 A1 2/2011 Drmanac et al.
2011/0045462 A1 2/2011 Fu et al.
2011/0059436 A1 3/2011 Hardin et al.
2011/0111409 A1 5/2011 Sinicropi et al.
2011/0152111 A1 6/2011 Fan et al.
2011/0223613 A1 9/2011 Gut
2011/0237449 A1 9/2011 McMaster et al.
2011/0245101 A1 10/2011 Chee et al.
2011/0245111 A1 10/2011 Chee
2011/0287435 A1 11/2011 Grunenwald et al.
2012/0010091 A1 1/2012 Linnarson
2012/0021930 A1 1/2012 Schoen et al.
2012/0046175 A1 2/2012 Rodesch et al.
2012/0046178 A1 2/2012 Van Den Boom et al.
2012/0065081 A1 3/2012 Chee
2012/0135871 A1 5/2012 van Eijk et al.
2012/0202698 A1 8/2012 van Eijk et al.
2012/0202704 A1 8/2012 Fan et al.
2012/0220479 A1 8/2012 Ericsson et al.
2012/0245053 A1 9/2012 Shirai et al.
2012/0252702 A1 10/2012 Muratani et al.
2012/0258871 A1 10/2012 Kozlov et al.
2012/0289414 A1 11/2012 Mitra et al.
2012/0301925 A1 11/2012 Belyaev
2012/0322099 A1 12/2012 Lapen et al.
2013/0005594 A1 1/2013 Terbrueggen et al.
2013/0005600 A1 1/2013 Olek
2013/0023433 A1 1/2013 Luo et al.
2013/0035239 A1 2/2013 Kong et al.
2013/0040842 A1 2/2013 Lim et al.
2013/0065768 A1 3/2013 Zheng et al.
2013/0079232 A1 3/2013 Kain et al.
2013/0171621 A1 7/2013 Luo et al.
2013/0244884 A1 9/2013 Jacobson et al.
2013/0261019 A1 10/2013 Lin et al.
2013/0302801 A1 11/2013 Asbury et al.
2013/0338042 A1 12/2013 Shen et al.
2014/0065609 A1 3/2014 Hicks et al.
2014/0066318 A1 3/2014 Frisen et al.
2014/0099637 A1 4/2014 Nolan et al.
2014/0121118 A1 5/2014 Warner
2014/0155295 A1 6/2014 Hindson et al.
2014/0270435 A1 9/2014 Dunn
2014/0272965 A1 9/2014 Handique et al.
2014/0274731 A1 9/2014 Raymond et al.
2014/0323330 A1 10/2014 Glezer et al.
2014/0342921 A1 11/2014 Weiner
2014/0378345 A1 12/2014 Hindson et al.
2014/0378350 A1 12/2014 Hindson et al.
2015/0000854 A1 1/2015 Gann-Fetter et al.
2015/0132743 A1 5/2015 Egidio et al.
2015/0292988 A1 10/2015 Bharadwaj et al.
2015/0298091 A1 10/2015 Weitz et al.
2015/0344942 A1 12/2015 Frisen et al.
2015/0368704 A1 12/2015 Fan et al.
2015/0376609 A1 12/2015 Hindson et al.
2016/0019337 A1 1/2016 Roberts et al.
2016/0024576 A1 1/2016 Chee
2016/0032282 A1 2/2016 Vigneault et al.
2016/0041159 A1 2/2016 Labaer et al.
2016/0060687 A1 3/2016 Zhu et al.
2016/0108458 A1 4/2016 Frei et al.
2016/0122817 A1 5/2016 Jarosz et al.
2016/0138091 A1 5/2016 Chee et al.
2016/0145677 A1 5/2016 Chee et al.
2016/0160169 A1 6/2016 Paczkowski et al.
2016/0194692 A1 7/2016 Gore et al.
2016/0201125 A1 7/2016 Samuels et al.
2016/0253584 A1 9/2016 Fodor et al.
2016/0289669 A1 10/2016 Fan et al.
2016/0289740 A1 10/2016 Fu et al.
2016/0298180 A1 10/2016 Chee
2016/0305856 A1 10/2016 Boyden et al.
2016/0333403 A1 11/2016 Chee
2016/0376642 A1 12/2016 Landegren et al.
2017/0009278 A1 1/2017 Söderberg et al.
2017/0016053 A1 1/2017 Beechem et al.
2017/0029875 A1 2/2017 Zhang et al.
2017/0058339 A1 3/2017 Chee
2017/0058340 A1 3/2017 Chee
2017/0058345 A1 3/2017 Chee
2017/0067096 A1 3/2017 Wassie et al.
2017/0088881 A1 3/2017 Chee
2017/0089811 A1 3/2017 Tillberg et al.
2017/0159109 A1 6/2017 Zheng et al.
2017/0166962 A1 6/2017 van Eijk et al.
2017/0220733 A1 8/2017 Zhuang et al.
2017/0233722 A1 8/2017 Seelig et al.
2017/0241911 A1 8/2017 Rockel et al.
2017/0242020 A1 8/2017 Yamauchi et al.
2017/0283860 A1 10/2017 Kool et al.
2017/0335297 A1 11/2017 Ha et al.
2017/0335410 A1 11/2017 Driscoll et al.
2017/0342405 A1 11/2017 Fu et al.
2017/0343545 A1 11/2017 Hadrup et al.
2017/0349940 A1 12/2017 Morin et al.
2018/0051322 A1 2/2018 Church et al.
2018/0057873 A1 3/2018 Zhou et al.
2018/0080019 A1 3/2018 Blainey et al.
2018/0088112 A1 3/2018 Fan et al.
2018/0094316 A1 4/2018 Oliphant et al.
2018/0105808 A1 4/2018 Mikkelsen et al.
2018/0112212 A1 4/2018 Nicol et al.
2018/0112261 A1 4/2018 Van Driel et al.
2018/0114316 A1 4/2018 Lele et al.
2018/0127817 A1 5/2018 Borchert et al.
2018/0163265 A1 6/2018 Zhang et al.
2018/0179590 A1 6/2018 Belgrader et al.
2018/0179591 A1 6/2018 Eijk
2018/0201925 A1 7/2018 Steemers et al.
2018/0201980 A1 7/2018 Chee et al.

(56) References Cited

U.S. PATENT DOCUMENTS

| | | | |
|---|---|---|---|
| 2018/0208967 | A1 | 7/2018 | Larman et al. |
| 2018/0216161 | A1 | 8/2018 | Chen et al. |
| 2018/0216162 | A1 | 8/2018 | Belhocine et al. |
| 2018/0237864 | A1 | 8/2018 | Imler et al. |
| 2018/0237951 | A1 | 8/2018 | Bock et al. |
| 2018/0245142 | A1 | 8/2018 | So et al. |
| 2018/0247017 | A1 | 8/2018 | van Eijk et al. |
| 2018/0251825 | A1 | 9/2018 | Stoeckius et al. |
| 2018/0282803 | A1 | 10/2018 | Belgrader et al. |
| 2018/0291427 | A1 | 10/2018 | Edelman |
| 2018/0291439 | A1 | 10/2018 | van Eijk et al. |
| 2018/0305681 | A1 | 10/2018 | Jovanovich et al. |
| 2018/0312822 | A1 | 11/2018 | Lee et al. |
| 2018/0320226 | A1 | 11/2018 | Church et al. |
| 2018/0334670 | A1 | 11/2018 | Bharadwaj et al. |
| 2018/0346970 | A1 | 12/2018 | Chang |
| 2019/0055594 | A1 | 2/2019 | Samusik et al. |
| 2019/0064173 | A1 | 2/2019 | Bharadwaj et al. |
| 2019/0071656 | A1 | 3/2019 | Chang et al. |
| 2019/0085324 | A1 | 3/2019 | Regev et al. |
| 2019/0085383 | A1 | 3/2019 | Church et al. |
| 2019/0100632 | A1 | 4/2019 | Delaney et al. |
| 2019/0119735 | A1 | 4/2019 | Deisseroth et al. |
| 2019/0135774 | A1 | 5/2019 | Orbai |
| 2019/0144936 | A1 | 5/2019 | Gierahn et al. |
| 2019/0145982 | A1 | 5/2019 | Chee et al. |
| 2019/0161796 | A1 | 5/2019 | Hauling et al. |
| 2019/0177777 | A1 | 6/2019 | Chee |
| 2019/0177778 | A1 | 6/2019 | Chee |
| 2019/0177789 | A1 | 6/2019 | Hindson et al. |
| 2019/0177800 | A1 | 6/2019 | Boutet et al. |
| 2019/0194709 | A1 | 6/2019 | Church et al. |
| 2019/0203275 | A1 | 7/2019 | Frisen et al. |
| 2019/0218276 | A1 | 7/2019 | Regev et al. |
| 2019/0218607 | A1 | 7/2019 | Love et al. |
| 2019/0218608 | A1 | 7/2019 | Daugharthy et al. |
| 2019/0233878 | A1 | 8/2019 | Delaney et al. |
| 2019/0233880 | A1 | 8/2019 | Mir |
| 2019/0249226 | A1 | 8/2019 | Bent et al. |
| 2019/0262831 | A1 | 8/2019 | West et al. |
| 2019/0264268 | A1 | 8/2019 | Frisen et al. |
| 2019/0271028 | A1 | 9/2019 | Khafizov et al. |
| 2019/0271030 | A1 | 9/2019 | Chee |
| 2019/0271031 | A1 | 9/2019 | Chee |
| 2019/0276880 | A1 | 9/2019 | Fan et al. |
| 2019/0300943 | A1 | 10/2019 | Chee et al. |
| 2019/0300944 | A1 | 10/2019 | Chee et al. |
| 2019/0300945 | A1 | 10/2019 | Chee et al. |
| 2019/0309353 | A1 | 10/2019 | Chee |
| 2019/0309354 | A1 | 10/2019 | Chee |
| 2019/0309355 | A1 | 10/2019 | Chee |
| 2019/0323071 | A1 | 10/2019 | Chee |
| 2019/0323088 | A1 | 10/2019 | Boutet et al. |
| 2019/0330617 | A1 | 10/2019 | Church et al. |
| 2019/0338353 | A1 | 11/2019 | Belgrader et al. |
| 2019/0352708 | A1 | 11/2019 | Gaige et al. |
| 2019/0360034 | A1 | 11/2019 | Zhou et al. |
| 2019/0360043 | A1 | 11/2019 | Pham et al. |
| 2019/0367969 | A1 | 12/2019 | Belhocine et al. |
| 2019/0367982 | A1 | 12/2019 | Belhocine et al. |
| 2019/0367997 | A1 | 12/2019 | Bent et al. |
| 2020/0002763 | A1 | 1/2020 | Belgrader et al. |
| 2020/0002764 | A1 | 1/2020 | Belgrader et al. |
| 2020/0010891 | A1 | 1/2020 | Beechem et al. |
| 2020/0024641 | A1 | 1/2020 | Nolan et al. |
| 2020/0047010 | A1 | 2/2020 | Lee et al. |
| 2020/0048690 | A1 | 2/2020 | Chee |
| 2020/0063191 | A1 | 2/2020 | Kennedy-Darling et al. |
| 2020/0063195 | A1 | 2/2020 | Chee |
| 2020/0063196 | A1 | 2/2020 | Chee |
| 2020/0071751 | A1 | 3/2020 | Daugharthy et al. |
| 2020/0080136 | A1 | 3/2020 | Zhang et al. |
| 2020/0109443 | A1 | 4/2020 | Chee |
| 2020/0123597 | A1 | 4/2020 | Daniel |
| 2020/0140920 | A1 | 5/2020 | Pierce et al. |
| 2020/0173985 | A1 | 6/2020 | Dong et al. |
| 2020/0199565 | A1 | 6/2020 | Chen et al. |
| 2020/0199572 | A1 | 6/2020 | Kuersten et al. |
| 2020/0217850 | A1 | 7/2020 | Liu et al. |
| 2020/0224244 | A1 | 7/2020 | Nilsson et al. |
| 2020/0239874 | A1 | 7/2020 | Mikkelsen |
| 2020/0239946 | A1 | 7/2020 | Dewal |
| 2020/0256867 | A1 | 8/2020 | Hennek et al. |
| 2020/0277663 | A1 | 9/2020 | Iyer |
| 2020/0277664 | A1 | 9/2020 | Frenz |
| 2020/0283852 | A1 | 9/2020 | Oliphant et al. |
| 2020/0299757 | A1 | 9/2020 | Chee et al. |
| 2020/0325531 | A1 | 10/2020 | Chee |
| 2020/0362398 | A1 | 11/2020 | Kishi et al. |
| 2020/0370095 | A1 | 11/2020 | Farmer et al. |
| 2020/0399687 | A1 | 12/2020 | Frisen et al. |
| 2020/0407781 | A1 | 12/2020 | Schnall-Levin |
| 2021/0010068 | A1 | 1/2021 | Chee et al. |
| 2021/0010070 | A1 | 1/2021 | Schnall-Levin et al. |
| 2021/0017587 | A1 | 1/2021 | Cai et al. |
| 2021/0095331 | A1 | 4/2021 | Fan et al. |
| 2021/0115504 | A1 | 4/2021 | Cai et al. |
| 2021/0123040 | A1 | 4/2021 | Macosko et al. |
| 2021/0130881 | A1 | 5/2021 | Cox |
| 2021/0140982 | A1 | 5/2021 | Uytingco et al. |
| 2021/0150707 | A1 | 5/2021 | Weisenfeld et al. |
| 2021/0155982 | A1 | 5/2021 | Yin et al. |
| 2021/0158522 | A1 | 5/2021 | Weisenfeld et al. |
| 2021/0172007 | A1 | 6/2021 | Chee et al. |
| 2021/0189475 | A1 | 6/2021 | Tentori et al. |
| 2021/0190770 | A1 | 6/2021 | Delaney et al. |
| 2021/0198741 | A1 | 7/2021 | Williams |
| 2021/0199660 | A1 | 7/2021 | Williams et al. |
| 2021/0207202 | A1 | 7/2021 | Chee |
| 2021/0214785 | A1 | 7/2021 | Stoeckius |
| 2021/0222235 | A1 | 7/2021 | Chee |
| 2021/0222241 | A1 | 7/2021 | Bharadwaj |
| 2021/0222242 | A1 | 7/2021 | Ramachandran Iyer |
| 2021/0222253 | A1 | 7/2021 | Uytingco |
| 2021/0223227 | A1 | 7/2021 | Stoeckius |
| 2021/0230584 | A1 | 7/2021 | Mikkelsen et al. |
| 2021/0230681 | A1 | 7/2021 | Patterson et al. |
| 2021/0230692 | A1 | 7/2021 | Daugharthy et al. |
| 2021/0237022 | A1 | 8/2021 | Bava |
| 2021/0238581 | A1 | 8/2021 | Mikkelsen et al. |
| 2021/0238664 | A1 | 8/2021 | Bava et al. |
| 2021/0238675 | A1 | 8/2021 | Bava |
| 2021/0238680 | A1 | 8/2021 | Bava |
| 2021/0247316 | A1 | 8/2021 | Bava |
| 2021/0255175 | A1 | 8/2021 | Chee et al. |
| 2021/0262018 | A1 | 8/2021 | Bava et al. |
| 2021/0262019 | A1 | 8/2021 | Alvarado Martinez et al. |
| 2021/0269864 | A1 | 9/2021 | Chee |
| 2021/0270822 | A1 | 9/2021 | Chee |
| 2021/0277460 | A1 | 9/2021 | Bava |
| 2021/0285036 | A1 | 9/2021 | Yin et al. |
| 2021/0285046 | A1 | 9/2021 | Chell et al. |
| 2021/0292748 | A1 | 9/2021 | Frisen et al. |
| 2021/0292822 | A1 | 9/2021 | Frisen et al. |
| 2021/0317510 | A1 | 10/2021 | Chee et al. |
| 2021/0317524 | A1 | 10/2021 | Lucero et al. |
| 2021/0324457 | A1 | 10/2021 | Ramachandran Iyer et al. |
| 2021/0332424 | A1 | 10/2021 | Schnall-Levin |
| 2021/0332425 | A1 | 10/2021 | Pfeiffer et al. |
| 2021/0348221 | A1 | 11/2021 | Chell et al. |
| 2022/0002791 | A1 | 1/2022 | Frisen et al. |
| 2022/0003755 | A1 | 1/2022 | Chee |
| 2022/0010367 | A1 | 1/2022 | Ramachandran Iyer et al. |
| 2022/0017951 | A1 | 1/2022 | Ramachandran Iyer et al. |
| 2022/0025446 | A1 | 1/2022 | Shah |
| 2022/0025447 | A1 | 1/2022 | Tentori et al. |
| 2022/0033888 | A1 | 2/2022 | Schnall-Levin et al. |
| 2022/0049293 | A1 | 2/2022 | Frenz et al. |
| 2022/0064630 | A1 | 3/2022 | Bent et al. |
| 2022/0081728 | A1 | 3/2022 | Williams |
| 2022/0090058 | A1 | 3/2022 | Frisen et al. |
| 2022/0090175 | A1 | 3/2022 | Uytingco et al. |
| 2022/0098576 | A1 | 3/2022 | Dadhwal |
| 2022/0098661 | A1 | 3/2022 | Chew et al. |

(56) References Cited

U.S. PATENT DOCUMENTS

| | | | |
|---|---|---|---|
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0112545 | A1 | 4/2022 | Chee |
| 2022/0119869 | A1 | 4/2022 | Ramachandran Iyer et al. |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |
| 2022/0170083 | A1 | 6/2022 | Khaled et al. |
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |
| 2022/0220544 | A1 | 7/2022 | Ach et al. |
| 2022/0241780 | A1 | 8/2022 | Tentori et al. |
| 2022/0267844 | A1 | 8/2022 | Ramachandran Iyer et al. |
| 2022/0282329 | A1 | 9/2022 | Chell et al. |
| 2022/0290217 | A1 | 9/2022 | Frenz et al. |
| 2022/0290219 | A1 | 9/2022 | Chee |
| 2022/0298560 | A1 | 9/2022 | Frisen et al. |
| 2022/0315984 | A1 | 10/2022 | Edelman et al. |
| 2022/0325325 | A1 | 10/2022 | Chee et al. |
| 2022/0326251 | A1 | 10/2022 | Uytingco et al. |
| 2022/0333171 | A1 | 10/2022 | Chee |
| 2022/0333191 | A1 | 10/2022 | Mikkelsen et al. |
| 2022/0333192 | A1 | 10/2022 | Uytingco |
| 2022/0333195 | A1 | 10/2022 | Schnall-Levin et al. |
| 2022/0348905 | A1 | 11/2022 | Dadhwal |
| 2022/0348992 | A1 | 11/2022 | Stoeckius et al. |
| 2022/0356464 | A1 | 11/2022 | Kim et al. |
| 2022/0364163 | A1 | 11/2022 | Stahl et al. |
| 2022/0389491 | A1 | 12/2022 | Chee |
| 2022/0389503 | A1 | 12/2022 | Mikkelsen et al. |
| 2022/0389504 | A1 | 12/2022 | Chew et al. |
| 2022/0403374 | A1 | 12/2022 | Soumillon |
| 2022/0403455 | A1 | 12/2022 | Ramachandran Iyer et al. |
| 2022/0404245 | A1 | 12/2022 | Chell et al. |
| 2023/0002812 | A1 | 1/2023 | Stoeckius et al. |
| 2023/0014008 | A1 | 1/2023 | Shastry |
| 2023/0017773 | A1 | 1/2023 | Kim et al. |
| 2023/0031305 | A1 | 2/2023 | Hernandez Neuta et al. |
| 2023/0033960 | A1 | 2/2023 | Gallant et al. |
| 2023/0034039 | A1 | 2/2023 | Shahjamali |
| 2023/0034216 | A1 | 2/2023 | Bava |
| 2023/0040363 | A1 | 2/2023 | Chee |
| 2023/0042088 | A1 | 2/2023 | Chee |
| 2023/0042817 | A1 | 2/2023 | Mignardi |
| 2023/0047782 | A1 | 2/2023 | Tentori et al. |
| 2023/0056549 | A1 | 2/2023 | Dadhwal |
| 2023/0064372 | A1 | 3/2023 | Chell et al. |
| 2023/0069046 | A1 | 3/2023 | Chew et al. |
| 2023/0077364 | A1 | 3/2023 | Patterson et al. |
| 2023/0080543 | A1 | 3/2023 | Katiraee et al. |
| 2023/0081381 | A1 | 3/2023 | Chew et al. |
| 2023/0100497 | A1 | 3/2023 | Frisen et al. |
| 2023/0107023 | A1 | 4/2023 | Chee |
| 2023/0111225 | A1 | 4/2023 | Chew et al. |
| 2023/0113230 | A1 | 4/2023 | Kim et al. |
| 2023/0126825 | A1 | 4/2023 | Nagendran et al. |
| 2023/0129552 | A1 | 4/2023 | Ramachandran Iyer |
| 2023/0135010 | A1 | 5/2023 | Tentori et al. |
| 2023/0143569 | A1 | 5/2023 | Iyer et al. |
| 2023/0145575 | A1 | 5/2023 | Gallant et al. |
| 2023/0147726 | A1 | 5/2023 | Hadrup et al. |
| 2023/0151412 | A1 | 5/2023 | Chee |
| 2023/0159994 | A1 | 5/2023 | Chee |
| 2023/0159995 | A1 | 5/2023 | Iyer et al. |
| 2023/0160008 | A1 | 5/2023 | Chell et al. |
| 2023/0175045 | A1 | 6/2023 | Katsori et al. |
| 2023/0183684 | A1 | 6/2023 | Gallant et al. |
| 2023/0183785 | A1 | 6/2023 | Frisen et al. |
| 2023/0194469 | A1 | 6/2023 | Tentori et al. |
| 2023/0194470 | A1 | 6/2023 | Kim et al. |
| 2023/0203478 | A1 | 6/2023 | Kim et al. |
| 2023/0212650 | A1 | 7/2023 | Chew et al. |
| 2023/0212655 | A1 | 7/2023 | Chee |
| 2023/0212656 | A1 | 7/2023 | Chow et al. |
| 2023/0220368 | A1 | 7/2023 | Kim |
| 2023/0220454 | A1 | 7/2023 | Bent et al. |
| 2023/0220455 | A1 | 7/2023 | Galonska et al. |
| 2023/0227811 | A1 | 7/2023 | Dadhwal |
| 2023/0228762 | A1 | 7/2023 | Uytingco et al. |
| 2023/0242973 | A1 | 8/2023 | Frisen et al. |
| 2023/0242976 | A1 | 8/2023 | Tentori et al. |
| 2023/0265488 | A1 | 8/2023 | Gohil et al. |
| 2023/0265489 | A1 | 8/2023 | Uytingco et al. |
| 2023/0265491 | A1 | 8/2023 | Tentori et al. |
| 2023/0267625 | A1 | 8/2023 | Tentori et al. |
| 2023/0279474 | A1 | 9/2023 | Katiraee |
| 2023/0279477 | A1 | 9/2023 | Kvastad et al. |
| 2023/0279481 | A1 | 9/2023 | Marrache et al. |
| 2023/0287399 | A1 | 9/2023 | Gallant et al. |
| 2023/0287475 | A1 | 9/2023 | Chell et al. |
| 2023/0287481 | A1 | 9/2023 | Katsori et al. |
| 2023/0295699 | A1 | 9/2023 | Sukovich et al. |
| 2023/0295722 | A1 | 9/2023 | Bharadwaj |
| 2023/0304072 | A1 | 9/2023 | Gohil et al. |
| 2023/0304074 | A1 | 9/2023 | Chee et al. |
| 2023/0304078 | A1 | 9/2023 | Frisen et al. |
| 2023/0313279 | A1 | 10/2023 | Giacomello et al. |
| 2023/0323340 | A1 | 10/2023 | Dadhwal |
| 2023/0323434 | A1 | 10/2023 | Yin et al. |
| 2023/0323436 | A1 | 10/2023 | Chee |
| 2023/0323447 | A1 | 10/2023 | Schnall-Levin et al. |
| 2023/0323453 | A1 | 10/2023 | Stoeckius |
| 2023/0332138 | A1 | 10/2023 | Kim et al. |
| 2023/0332211 | A1 | 10/2023 | Chee |
| 2023/0332212 | A1 | 10/2023 | Chew et al. |
| 2023/0332227 | A1 | 10/2023 | Ramachandran Iyer |
| 2023/0332247 | A1 | 10/2023 | Singh et al. |
| 2023/0351619 | A1 | 11/2023 | Tentori et al. |
| 2023/0358733 | A1 | 11/2023 | Chee |
| 2023/0366008 | A1 | 11/2023 | Chew et al. |
| 2023/0383285 | A1 | 11/2023 | Kim et al. |
| 2023/0383344 | A1 | 11/2023 | Stoeckius |
| 2023/0392204 | A1 | 12/2023 | Chell et al. |
| 2023/0393071 | A1 | 12/2023 | Bava |
| 2023/0407404 | A1 | 12/2023 | Baumgartner et al. |
| 2023/0416807 | A1 | 12/2023 | Chee |
| 2023/0416808 | A1 | 12/2023 | Sukovich et al. |
| 2023/0416850 | A1 | 12/2023 | Singh et al. |
| 2024/0002931 | A1 | 1/2024 | Bava |
| 2024/0011081 | A1 | 1/2024 | Chee |
| 2024/0011090 | A1 | 1/2024 | Chew et al. |
| 2024/0018572 | A1 | 1/2024 | Mignardi |
| 2024/0018575 | A1 | 1/2024 | Gallant et al. |
| 2024/0018589 | A1 | 1/2024 | Schnall-Levin et al. |
| 2024/0026445 | A1 | 1/2024 | Ramachandran Iyer et al. |
| 2024/0033743 | A1 | 2/2024 | Tentori et al. |
| 2024/0035937 | A1 | 2/2024 | Cox et al. |
| 2024/0043908 | A1 | 2/2024 | Chew et al. |
| 2024/0043925 | A1 | 2/2024 | Bent et al. |
| 2024/0052343 | A1 | 2/2024 | Gallant et al. |
| 2024/0053351 | A1 | 2/2024 | Uytingco et al. |
| 2024/0060115 | A1 | 2/2024 | Chee et al. |
| 2024/0067953 | A1 | 2/2024 | Mikkelsen et al. |
| 2024/0068016 | A1 | 2/2024 | Frisen et al. |
| 2024/0068017 | A1 | 2/2024 | Lundeberg et al. |
| 2024/0076723 | A1 | 3/2024 | Mignardi |
| 2024/0080346 | A1 | 3/2024 | Engblom et al. |
| 2024/0084365 | A1 | 3/2024 | Frisen et al. |
| 2024/0084366 | A1 | 3/2024 | Chee |
| 2024/0084383 | A1 | 3/2024 | Ramachandran Iyer et al. |
| 2024/0093274 | A1 | 3/2024 | Frisen et al. |
| 2024/0093290 | A1 | 3/2024 | Stahl et al. |
| 2024/0110228 | A1 | 4/2024 | Uytingco et al. |
| 2024/0124933 | A1 | 4/2024 | Chell et al. |
| 2024/0125772 | A1 | 4/2024 | Delaney et al. |
| 2024/0141327 | A1 | 5/2024 | Kim et al. |
| 2024/0158838 | A1 | 5/2024 | Alvarado Martinez et al. |
| 2024/0175080 | A1 | 5/2024 | Galonska et al. |
| 2024/0182968 | A1 | 6/2024 | Bava |

(56) References Cited

U.S. PATENT DOCUMENTS

| | | | |
|---|---|---|---|
| 2024/0191286 | A1 | 6/2024 | Boutet et al. |
| 2024/0200121 | A1 | 6/2024 | Boutet |
| 2024/0209425 | A1 | 6/2024 | Yin et al. |
| 2024/0218427 | A1 | 7/2024 | Sukovich et al. |
| 2024/0218432 | A1 | 7/2024 | Mielinis |
| 2024/0219701 | A1 | 7/2024 | Tentori et al. |
| 2024/0253036 | A1 | 8/2024 | Kim et al. |
| 2024/0263218 | A1 | 8/2024 | Katiraee et al. |
| 2024/0271190 | A1 | 8/2024 | Stoeckius et al. |
| 2024/0271195 | A1 | 8/2024 | Mikhaiel et al. |
| 2024/0279747 | A1 | 8/2024 | Williams |
| 2024/0287600 | A1 | 8/2024 | Iyer et al. |
| 2024/0294971 | A1 | 9/2024 | Galonska |
| 2024/0294974 | A1 | 9/2024 | Galonska et al. |
| 2024/0294975 | A1 | 9/2024 | Lin et al. |
| 2024/0301488 | A1 | 9/2024 | Stoeckius |
| 2024/0301489 | A1 | 9/2024 | Chew et al. |
| 2024/0360494 | A1 | 10/2024 | Costa et al. |
| 2024/0368711 | A1 | 11/2024 | Giacomello et al. |
| 2024/0377297 | A1 | 11/2024 | Cox et al. |
| 2024/0385088 | A1 | 11/2024 | Kim et al. |
| 2024/0392349 | A1 | 11/2024 | Frisen et al. |
| 2024/0392351 | A1 | 11/2024 | Chee |
| 2024/0392352 | A1 | 11/2024 | Stahl et al. |
| 2024/0392353 | A1 | 11/2024 | Engblom et al. |
| 2024/0401109 | A1 | 12/2024 | Kim et al. |
| 2024/0401117 | A1 | 12/2024 | Bava |
| 2024/0401118 | A1 | 12/2024 | Tentori et al. |
| 2024/0404301 | A1 | 12/2024 | Li et al. |
| 2024/0408593 | A1 | 12/2024 | Kim et al. |
| 2024/0416315 | A1 | 12/2024 | Bava |
| 2024/0417783 | A1 | 12/2024 | Chew et al. |
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019689 | A1 | 1/2025 | Galonska et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101501 | A1 | 3/2025 | Chee |
| 2025/0101502 | A1 | 3/2025 | Chee |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154565 | A1 | 5/2025 | Chee |
| 2025/0154566 | A1 | 5/2025 | Chee |
| 2025/0154567 | A1 | 5/2025 | Chee |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |
| 2025/0179475 | A1 | 6/2025 | Borgstrom et al. |
| 2025/0182305 | A1 | 6/2025 | Tentori et al. |
| 2025/0182503 | A1 | 6/2025 | Li et al. |
| 2025/0188526 | A1 | 6/2025 | Sukovich et al. |
| 2025/0189483 | A1 | 6/2025 | Kim et al. |
| 2025/0197847 | A1 | 6/2025 | Kim et al. |
| 2025/0197938 | A1 | 6/2025 | Bjorninen |
| 2025/0207125 | A1 | 6/2025 | Gupta et al. |
| 2025/0207182 | A1 | 6/2025 | Chee |
| 2025/0207183 | A1 | 6/2025 | Chee |
| 2025/0207195 | A1 | 6/2025 | Chell et al. |
| 2025/0208115 | A1 | 6/2025 | Bent |
| 2025/0215482 | A1 | 7/2025 | Mignardi et al. |
| 2025/0215484 | A1 | 7/2025 | Ramachandran Iyer et al. |
| 2025/0216300 | A1 | 7/2025 | Delaney et al. |
| 2025/0216303 | A1 | 7/2025 | Cox et al. |
| 2025/0223633 | A1 | 7/2025 | Frenz et al. |
| 2025/0230487 | A1 | 7/2025 | Chee et al. |
| 2025/0230498 | A1 | 7/2025 | Katiraee |
| 2025/0250621 | A1 | 8/2025 | Galonska et al. |
| 2025/0250632 | A1 | 8/2025 | Mignardi et al. |
| 2025/0257393 | A1 | 8/2025 | Katiraee et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1813059 | 8/2006 |
| CN | 1898398 | 1/2007 |
| CN | 101142325 | 3/2008 |
| CN | 101221182 | 7/2008 |
| CN | 101522915 | 9/2009 |
| CN | 105441549 | 3/2016 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| EP | 3425053 | 8/2020 |
| GB | 2520765 | 6/2015 |
| JP | 2007-014297 | 1/2007 |
| JP | 2007-074967 | 3/2007 |
| JP | 2009-036694 | 2/2009 |
| RU | 2270254 | 2/2006 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/024940 | 5/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/024952 | 3/2002 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |

(56) References Cited

FOREIGN PATENT DOCUMENTS

| | | |
|---|---|---|
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/117541 | 11/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/019964 | 2/2011 |
| WO | WO 2011/062933 | 5/2011 |
| WO | WO 2011/068088 | 6/2011 |
| WO | WO 2011/094669 | 8/2011 |
| WO | WO 2011/127006 | 10/2011 |
| WO | WO 2011/155833 | 12/2011 |
| WO | WO 2012/048341 | 4/2012 |
| WO | WO 2012/049316 | 4/2012 |
| WO | WO 2012/061832 | 5/2012 |
| WO | WO 2012/071428 | 5/2012 |
| WO | WO 2012/083225 | 6/2012 |
| WO | WO 2012/129242 | 9/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/128129 | 8/2014 |
| WO | WO 2014/130576 | 8/2014 |
| WO | WO 2014/144713 | 9/2014 |
| WO | WO 2014/152397 | 9/2014 |
| WO | WO 2014/201273 | 12/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2015/168161 | 11/2015 |
| WO | WO 2015/188839 | 12/2015 |
| WO | WO 2016/040476 | 3/2016 |
| WO | WO 2016/044313 | 3/2016 |
| WO | WO 2016/057552 | 4/2016 |
| WO | WO 2016/077763 | 5/2016 |
| WO | WO 2016/100196 | 6/2016 |
| WO | WO 2016/126871 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/013170 | 1/2017 |
| WO | WO 2017/019456 | 2/2017 |
| WO | WO 2017/019481 | 2/2017 |
| WO | WO 2017/044993 | 3/2017 |
| WO | WO 2017/075265 | 5/2017 |
| WO | WO 2017/075293 | 5/2017 |
| WO | WO 2017/096158 | 7/2017 |
| WO | WO 2017/143155 | 8/2017 |
| WO | WO 2017/147483 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/075693 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/148700 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/104337 | 5/2019 |
| WO | WO 2019/113457 | 6/2019 |
| WO | WO 2019/113533 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047007 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/077236 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/227309 | 11/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |

(56) References Cited

FOREIGN PATENT DOCUMENTS

| | | |
|---|---|---|
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |

OTHER PUBLICATIONS

[No Author Listed], "Microarray technologies have excellent possibilities in genomics-related researches," Science Tools From Amersham Pharmacia Biotech, 1998, 3(4): 8 pages (with English Translation).

[No Author Listed], "Proseek® Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide, " Jul. 2020, retrieved on May 25, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide RevD.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

Adamson et al., "A Multiplexed Single-Cell CRISPR Screening Platform Enables Systematic Dissection of the Unfolded Protein Response," Cell, Dec. 2016, 167(7):1867-1882.e21.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

(56) References Cited

OTHER PUBLICATIONS

Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage, " BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, p. 6.1-6.8.
Azioune et al., "Simple and rapid process for single cell micropatterning," Lab Chip, Jun. 2009, 9(11):1640-1642.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5): e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination, " Nucleic Acid Res., Aug. 2000, 28(15):2911-2914.
Bessmertnykh et al., "Efficient Palladium-Catalyzed Synthesis of Aminopyridyl Phosphonates from Bromopyridines and Diethyl Phosphite," Synthesis, 2008, 10:1575-1579.
Bielas et al., "Quantification of random genomic mutations," Nat. Methods, 2005, 2(4):285-290.
Biosyntagma.com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine, " J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35 - The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119- 129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.

(56) References Cited

OTHER PUBLICATIONS

Butler et al., "Integrating single-cell transcriptomic data across different conditions, technologies, and species," Nat Biotechnol., Jun. 2018, 36(5):411-420.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663- 4674.
Chen et al., "ATAC-see reveals the accessible genome by transposase-mediated imaging and sequencing," Nature Methods, Dec. 2016, 13(12):1013-1020.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Geometric control of cell life and death," Science, May 1997, 276(5317): 1425-1428.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "uCB-seq: microfluidic cell barcoding and sequencing for high-resolution imaging and sequencing of single cells," Lab Chip, Nov. 2020, 20(21):3899-3913.
Cheng et al., "Sensitive Detection of Small Molecules by Competitive Immunomagnetic-Proximity Ligation Assay," Anal Chem, 2012, 84:2129-2132.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Chrisey et al., "Covalent attachment of synthetic DNA to self-assembled monolayer films," Nucleic Acids Res., Aug. 1996, 24(15):3031-9.
Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 2013, 497:332-337.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Collins et al., "Two-dimensional single-cell patterning with one cell per well driven by surface acoustic waves," Nature Communications, Nov. 2015, 6:8686, 11 pages.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Corces et al., "Lineage-specific and single-cell chromatin accessibility charts human hematopoiesis and leukemia evolution," Nature Genetics, Oct. 2016, 48(10):1193-1203.
Credle et al., "Multiplexed analysis of fixed tissue RNA using Ligation in situ Hybridization," Nucleic Acids Research, 2017, 45(14):e128, 9 pages.
Crisalli et al., "Importance of ortho Proton Donors in Catalysis of Hydrazone Formation," Org. Lett., 2013, 15(7):1646-1649.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Daley et al., "Predicting the molecular complexity of sequencing libraries," Nature Methods, Apr. 2013, 10:325-327.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Datlinger et al., "Pooled CRISPR screening with single-cell transcriptome readout," Nat Methods, Mar. 2017, 14(3):297-301.
Daubendiek et al., "Rolling-Circle RNA Synthesis: Circular Oligonucleotides as Efficient Substrates for T7 Rna Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Depasquale et al., "DoubletDecon: Deconvoluting Doublets from Single-Cell RNA-Sequencing Data," Cell Rep., Nov. 5, 2019, 29(6):1718-1727.e8, 19 pages.
Ding et al., "On-chip manipulation of single microparticles, cells, and organisms using surface acoustic waves," PNAS, Jul. 2012, 109(28):11105-11109.
Dixit et al., "Perturb-Seq: Dissecting Molecular Circuits with Scalable Single-Cell RNA Profiling of Pooled Genetic Screens," Cell, Dec. 2016, 167(7):1853-1866.e17.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine et al., "Analysis of gene expression in single live neurons," Proc. Natl. Acad. Sci., USA 89, 3010-3014, 1992.

(56) References Cited

OTHER PUBLICATIONS

Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Falconnet et al., "Surface engineering approaches to micropattern surfaces for cell-based assays," Biomaterials, Jun. 2006, 27(16):3044-3063.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Folch et al., "Microfabricated elastomeric stencils for micropatterning cell cultures," J Biomed Mater Res, Nov. 2000, 52(2):346-353.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels, " PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 Dna ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Giam et al., "Scanning probe-enabled nanocombinatorics define the relationship between fibronectin feature size and stem cell fate," PNAS, Mar. 2012, 109(12):4377-4382.
Gierahn et al., "Seq-Well: portable, low-cost RNA sequencing of single cells at high throughput," ResearchSquare, 2017, 53 pages.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in Drosophila," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gross et al., "Technologies for Single-Cell Isolation," Int. J Mol. Sci., Jul. 2015, 16(8):16897-16919.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hafner et al., "Identification of microRNAs and other small regulatory RNAs using cDNA library sequencing, " Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS ONE, 2012, 7(7):e40405, 9 pages.

(56) References Cited

OTHER PUBLICATIONS

Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencing, " PLoS One, 5(7): e11345, 2010.
Hejatko et al., "In situ hybridization technique for mRNA detection in whole mount Arabidopsis samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains, " PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hu et al., "High reproducibility using sodium hydroxide-stripped long oligonucleotide DNA microarrays," Biotechniques, Jan. 2005, 38(1):121-4.
Hughes et al., "Choose Your Label Wisely: Water-Soluble Fluorophores Often Interact with Lipid Bilayers," PLoS One, Feb. 4, 2014, 9(2):e87649, 8 pages.
Hughes et al., "Highly Efficient, Massively-Parallel Single-Cell RNA-Seq Reveals Cellular States and Molecular Features of Human Skin Pathology," bioRxiv, Jul. 2019, 51 pages.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-ZeroR rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jabara et al., Accurate sampling and deep sequencing of the HIV-1 protease gene using a Primer ID. PNAS 108(50); 20166-20171, 2011.
Jaitin et al., "Dissecting Immune Circuits by Linking CRISPR-Pooled Screens with Single-Cell RNA-Seq," Cell, Dec. 2016, 167(7):1883-1896.e15.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jones et al., "Comparative lesion sequencing provides insights into tumor evolution," Proc. Natl. Acad. Sci. USA, 105(11): 4283-4288, 2008.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase 0 is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1): 173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Korsunsky et al., "Fast, sensitive and accurate integration of single-cell data with Harmony," Nat. Methods, Dec. 2019, 16(12):1289-1296.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.

(56) References Cited

OTHER PUBLICATIONS

Kuliszewska et al., "On the rearrangement of N-aryl-N.Box-phsphoramidates to N-Boc-protectedo-aminoarylphosphonates, " Chemical Monthly, Dec. 2017, 149(1):87-98.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA - protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lacar et al., "Nuclear RNA-seq of single neurons reveals molecular signatures of activation," Nat Commun., Apr. 2016, 7:11022, 12 pages.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lake et al., "Neuronal subtypes and diversity revealed by single-nucleus RNA sequencing of the human brain," Science, Jun. 2016, 352(6293):1586-90.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Laurell et al., "Chip integrated strategies for acoustic separation and manipulation of cells and particles," Chem. Soc. Rev., Mar. 2007, 36(3):492-506.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Lee et al., "XYZeq: Spatially resolved single-cell RNA sequencing reveals expression heterogeneity in the tumor microenvironment," Science Advances, 2021, 7:eabg4755, 1-14.
Leriche et al., "Cleavable linkers in chemical biology," Bioorganic & Medicinal Chemistry, 2012, 20:571-582.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Liberali et al., "Single-cell and multivariate approaches in genetic perturbation screens," Nat Rev Genet., Jan. 2015, 16(1):18-32.
Lin et al., "Highly multiplexed imaging of single cells using a high-throughput cyclic immunofluorescence method," Nat Commun., Sep. 2015, 6:8390, 7 pages.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods - general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lubeck et al., "Single cell systems biology by super-resolution imaging and combinatorial labeling," Nature Methods, Jan. 2013, 9(7):743-748, 18 pages.
Lubeck et al., "Single-cell in situ RNA profiling by sequential hybridization," Nature Methods, Apr. 2014, 11(4):360-361, 2 pages (Supplemental Materials).
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality Dna, Rna and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Macosko et al., "Highly Parallel Genome-wide Expression Profiling of Individual Cells Using Nanoliter Droplets," Cell, 2015, 161:1202-1214.
Madissoon et al., "scRNA-seq assessment of the human lung, spleen, and esophagus tissue stability after cold preservation," Genome Biol., Dec. 2019, 21(1):1, 16 pages.
Marx, "Method of the Year: spatially resolved transcriptomics," Nature Methods, 2021, 18(1):9-14.

(56) References Cited

OTHER PUBLICATIONS

Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
McGinnis et al., "MULTI-seq: sample multiplexing for single-cell RNA sequencing using lipid-tagged indices," Nat Methods, Jul. 2019, 16(7): 619-626, 14 pages.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies - the next generation," Nature Reviews Genetics, 2010, 11(1):31-46.
Miele et al., "Mapping cis- and trans- chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole- genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLOS One, Aug. 2012, 7(8):e42882, 8 pages.
Mortazavi et al., "Mapping and quantifying mammalian transcriptomes by RNA-Seq," Nature Methods, 5(7): 621-8, 2008.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nakamura et al., "Biocompatible inkjet printing technique for designed seeding of individual living cells," Tissue Eng, Nov. 2005, 11(11-12):1658-1666.
Nallur et al., "Signal amplification by rolling circle amplification on DNA microarrays," Nucleic Acids Res., Dec. 1, 2001, 29(23):e118, 9 pages.
Nam et al., "Somatic mutations and cell identity linked by Genotyping of Transcriptomes," Nature, Jul. 2019, 571(7765):355-360.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Noshita et al., "Diethylenetriamine-Mediated Direct Cleavage of Unactivated Carbamates and Ureas," Org. Lett., Nov. 15, 2016, 18:6062-6065.
Nowak et al., "Entering the Postgenome Era," Science, 1995, 270(5235):368-71.
O'Huallachain et al., "Ultra-high throughput single-cell analysis of proteins and RNAs by split-pool synthesis," Communications Biology, 2020, 3:213, 19 pages.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ostuni et al., "Patterning Mammalian Cells Using Elastomeric Membranes," Langmuir, Aug. 2000, 16(20):7811-7819.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/US2020/066705, dated Jun. 28, 2022, 9 pages.
PCT International Search Report and Written Opinion in International Appln. No. PCT/US2020/066705, dated Mar. 25, 2021, 14 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.

(56) References Cited

OTHER PUBLICATIONS

Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tcl/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rettig et al., "Large-scale single-cell trapping and imaging using microwell arrays," Anal Chem, Sep. 2005, 77(17):5628-5634.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution, " Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Satija et al., "Spatial reconstruction of single-cell gene expression data," Nature, Apr. 13, 2015, 33(5):495-402, 14 pages.
Satpathy et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health, " PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Setliff et al., High-Throughput Mapping of B Cell Receptor Sequences to Antigen Specificity, Cell, 2019, 179:1636-1646.
Shalon et al., "A Dna microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction, " Chem. Commun., 2011, 47(22):6257-6259.
Shendure et al., "Accurate multiplex polony sequencing of an evolved bacterial genome," Science, 2005, 309(5741):1728-1732.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections, " PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Stoeckius et al., "Cell Hashing with barcoded antibodies enables multiplexing and doublet detection for single cell genomics," Genome Biology, Dec. 19, 2018, 19: 224, 12 pages.
Stoeckius et al., "Simultaneous epitope and transcriptome measurement in single cells," Nature Methods, Jul. 31, 2017, 14(9):865-868.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.

(56) References Cited

OTHER PUBLICATIONS

Stuart et al., "Comprehensive Integration of Single-Cell Data," Cell, Jun. 2019, 177(7):1888-1902.
Suh et al., "A simple soft lithographic route to fabrication of poly(ethylene glycol) microstructures for protein and cell patterning," Biomaterials, Feb. 2004, 25(3):557-563.
Sutherland et al., "Utility of formaldehyde cross-linking and mass spectrometry in the study of protein-protein interactions," J. Mass Spectrom., Jun. 2008, 43(6):699-715.
Takei et al., "Integrated Spatial Genomics Reveals Global Architecture of Single Nuclei," Nature, Jan. 27, 2021, 590(7845):344-350, 53 pages.
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5:516-35, 2010.
Taniguchi et al., "Quantitative analysis of gene expression in a single cell by qPCR," Nature Methods, 6, pp. 503-506, 2009.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue, " PLoS ONE, Feb. 2019, 14(2):e0212031, 22 pages.
Tseng et al., "Magnetic nanoparticle-mediated massively parallel mechanical modulation of single-cell behavior," Nat Methods, Nov. 2012, 9(11):1113-1119.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Damme et al., "Chemical reversible crosslinking enables measurement of Rna 3D distances and alternative conformations in cells," Nature Communications, Feb. 17, 2022, 13:911, 13 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR, " Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Velema et al., "Trapping Transient RNA Complexes by Chemically Reversible Acylation," Angew Chem Int Ed Engl., Dec. 1, 2020, 59(49):22017-22022, 13 pages.
Vermesh et al., "High-density, multiplexed patterning of cells at single-cell resolution for tissue engineering and other applications," Angew Chem Int Ed Engl, Aug. 2011, 50(32):7378-7380.
Vickovic et al., "High-definition spatial transcriptomics for in situ tissue profiling," Nat Methods, Oct. 2019, 16(10):987-990.
Vickovic et al., "Massive and parallel expression profiling using microarrayed single-cell sequencing," Nat. Commun. Oct. 14, 2016, 7:13182, 9 pages.
Vickovic et al., "Massive and parallel expression profiling using microarrayed single-cell sequencing," Nature Communications, 2016, 7(13182):1-9.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Single cell analysis: the new frontier in 'omics," Trends Biotechnol., 28: 281-90, 2010.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Wei et al., "Redox-Responsive Polycondensate Neoepitope for Enhanced Personalized Cancer Vaccine," ACS Central Science, Feb. 3, 2020, 6:404-412.
Weinreich et al., "Evidence that the cis Preference of the Tn5 Transposase is Caused by Nonproductive Multimerization," Genes and Development, Oct. 1994, 8(19):2363-2374.
Wheeler et al., "Microfluidic device for single-cell analysis," Analytical Chemistry, Jul. 2003, 75(14):3581-3586.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.

(56) References Cited

OTHER PUBLICATIONS

Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Anal Biochem, 2001, 294(2):169-175.
Wright et al., "Reusable, reversibly sealable parylene membranes for cell and protein patterning," J Biomed Mater Res A., May 2008, 85(2):530-538.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples, " Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yamauchi et al., "Subcellular western blotting of single cells," Microsyst Nanoeng., 2017, 3:16079, 9 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling, " PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase, " PNAS, 2005, 102(44):15815-20.
Yusof et al., "Inkjet-like printing of single-cells," Lab Chip, Jul. 2011, 11(14):2447-2454.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Block-Cell-Printing for live single-cell printing, " PNAS, Feb. 2014, 111(8):2948-2953.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zhao et al., "Isothermal Amplification of Nucleic Acids," Chemical Reviews, Nov. 2015, 115(22):12491-12545.
Zheng et al., "Massively parallel digital transcriptional profiling of single cells," Nat Commun., Jan. 16, 2017, 8:14049, 12 pages.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
10xGenomics.com [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.
Gerard et al., "High-throughput single-cell activity-based screening and sequencing of antibodies using droplet microfluidics," Nature Biotechnology, Jun. 2020, 38(6):715-721, 19 pages.
Hatori et al., "Particle-Templated Emulsification for Microfluidics-Free Digital Biology," Anal. Chem., 2018, 90:9813-9820.
Kuhn et al., "A novel, high-performance random array platform for quantitative gene expression profiling," Genome Res, 2004, 14:2347-2356.
Asp et al., "A spatiotemporal organ-wide gene expression and cell atlas of the developing human heart," Cell, Dec. 12, 2019, 179(7):1647-1660.
Fiskin et al., "Single-cell multimodal profiling of proteins and chromatin accessibility using PHAGE-ATAC," bioRxiv, posted Oct. 20, 2020, 63 pages.
Howell et al., "iFRET: An Improved Fluorescence System for DNA-Melting Analysis," Genome Research, 2002, 12:1401-1407.
Lu et al., "Highly multiplexed profiling of single-cell effector functions reveals deep functional heterogeneity in response to pathogenic ligands," PNAS, Feb. 2, 2015, E607-E615.
Lu et al., "Highly multiplexed profiling of single-cell effector functions reveals deep functional heterogeneity in response to pathogenic ligands," PNAS, Feb. 2, 2015, E607-E615 (Supplementary Information), 94 pages.
Nam et al., "Nanoparticle-Based Bio-Bar Codes for the Ultrasensitive Detection of Proteins," Science, Sep. 26, 2003, 301(5641):1884-1886.
Pittcon, "Single Molecule Detection of Proteins in Single Cells," News-Medical, Feb. 3, 2017, retreived on Nov. 1, 2023, retrieved from URL <https://www.news-medical.net/news/20170203/Single-molecule-detection-of-proteins-in-single-cells.aspx>, 13 pages.
Redmond et al., "Single-cell TCRseq: paired recovery of entire T-cell alpha and beta chain transcripts in T-cell receptors from single-cell RNAseq," Genome Med, 2016, 8:80, 12 pages.
Tang et al., "mRNA-Seq whole-transcriptome analysis of a single cell," Nat Methods, 2009, 6:377-382.
U.S. Appl. No. 16/951,854.
Adam et al., "Psychrophilic proteases dramatically reduce single-cell RNA-seq artifacts: a molecular atlas of kidney development," Development, Oct. 1, 2017, 144(19):3625-3632.
Almog et al., "The crystal structures of the psychrophilic subtilisin S41 and the mesophilic subtilisin Sph reveal the same calcium-loaded state," Proteins, Feb. 1, 2009, 74(2):489-496.
Bibikova et al., "Quantitative gene expression profiling in formalin-fixed paraffin-embedded tissues using universal bead arrays," The American Journal of Pathology, Nov. 1, 2004, 165(5):1799-1807.
Cai et al., "Glutathione-mediated shedding of PEG layers based on disulfide-linked catiomers for DNA delivery," J. Mater. Chem., Sep. 20, 2011, 21(38):14639-14645.
Chapman et al., "All Wrapped up: Stabilization of Enzymes within Single Enzyme Nanoparticles," J. Am. Chem. Soc, Jan. 9, 2019, 141(7):2754-2769.
Choi et al., "Multiplexed detection of mRNA using porosity-tuned hydrogel microparticles," Analytical chemistry, Sep. 28, 2012, 84(21):9370-9378.
Eastburn et al., "Identification of Genetic Analysis of Cancer Cells with PCT-activated Cell Sorting," Nucleic Acids Research, Jul. 16, 2014, 42(16):e128, 10 pages.
Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.
Edsgard et al., "Identification of spatial expression trends in single-cell gene expression data," Nature Methods, Mar. 19, 2018, 15: 339-342, 16 pages.

(56) References Cited

OTHER PUBLICATIONS

Fan et al., “A versatile assay for high-throughput gene expression profiling on universal array matrices,” Genome Research, May 1, 2004, 14(5):878-885.
Gao et al., “Q&A: Expansion microscopy,” BMC Biology, 15:50, 9 pages, 2017.
Goldmeyer et al., “Development of a novel one-tube isothermal reverse transcription thermophilic helicase-dependent amplification platform for rapid RNA detection,” Journal of Molecular Diagnostics, American Society for Investigative Pathology and the Association for Molecular Pathology, Nov. 1, 2007, 9(5):639-644.
Ha et al., “Self-assembly hollow nanosphere for enzyme encapsulation,” Soft Matter, Feb. 11, 2010, 6, 1405-1408, 10 pages.
Hu et al., “A thermo-degradable hydrogel with light-tunable degradation and drug release,” Biomaterials, Jan. 2017, 112:133-140.
Ju et al., “Supramolecular dendrimer capsules by cooperative binding,” Chem. Commun., Jan. 7, 2011, 47(1):268-270, 8 pages.
Kuiper et al., “Enzymes containing porous polymersomes as nano reaction vessels for cascade reactions,” Org. Biomol, Chem, Oct. 15, 2008, 6(23):4315-4318.
Li et al., “Encapsulation of a Nerve Agent Detoxifying Enzyme by a Mesoporous Zirconium Metal-Organic Framework Engenders Thermal and Long-Term Stability,” J. Am. Chem. Soc., Jun. 24, 2016, 138(26):8052-8055, 4 pages.
Lian et al., “High efficiency and long-term intracellular activity of an enzymatic nanofactory based on metal-organic frameworks,” Nature Communications, Dec. 12, 2017, 8:2075, 10 pages.
Liu et al., “Preparation and Characterization of Temperature-Sensitive Poly(N-isopropylacrylamide)-b-poly(d,l-lactide) Microspheres for Protein Delivery,” Biomacromolecules, 2003, 4(6):1784-1793.
Luo et al., “Probing infectious disease by single-cell RNA sequencing: Progresses and perspectives,” Computational and Structural Biotechnology Journal, Oct. 21, 2020, 18:2962-2971.
Lyu et al., “One-Pot Synthesis of Protein-Embedded Metal-Organic Frameworks with Enhanced Biological Activities,” Nano Lett., Sep. 11, 2014, 14:5761-5765.
Massoni-Badosa et al., “Sampling artifacts in single-cell genomics cohort studies,” bioRxiv, Jan. 15, 2020, 32 pages.
Masuda et al., “Analysis of chemical modification of RNA from formalin-fixed samples and optimization of molecular biology applications for such samples,” Nucleic Acids Research, Nov. 1999, 27(22):4436-4443.
Miller et al., “Rapid and Efficient Enzyme Encapsulation in a Dendrimer Silica Nanocomposite,” Macromolecular Bioscience, Oct. 25, 2006, 6(10):839-845.
O’Flanagan et al., “Dissociation of solid tumor tissues with cold active protease for single-cell RNA-seq minimizes conserved collagenase-associated stress responses,” Genome Biology, Oct. 17, 2019, 20:210, 13 pages.
Pellegrino et al., “High-throughput Single-cell DNA Sequencing of Acut Myeloid Leukemia Tumors with Droplet Microfluidics,” Genome Research, Aug. 7, 2018, 28(9):1345-1352.
Rahimi et al., “Synthesis and Characterization of Thermo-Sensitive Nanoparticles for Drug Delivery Applications,” J. Biomed. Nanotechnol. Dec. 2008, 4(4):482-490, 19 pages.
Shieh, et al., “Imparting Functionality to Biocatalysts via Embedding Enzymes into Nanoporous Materials by a de Novo Approach: Size-Selective Sheltering of Catalase in Metal-Organic Framework Microcrystals,” J Am Chem Soc., Apr. 8, 2015, 137(13):4276-4279, 4 pages.
Soderberg, “Droplet Microfluidics Reverse Transcription and PCR Towards Single Cell and Exosome Analysis,” Doctoral Thesis, KTH School of Biotechnology Science for Life Laboratory, 2017, 69 pages.
Sun et al., “Statistical Analysis of Spatial Expression Pattern for Spatially Resolved Transcriptomic Studies,” Nature Methods, Jan. 27, 2020, 17(2): 193-200.
Svensson et al., “SpatialDE: identification of spatially variable genes,” Nature Methods, May 2018, 15:343-346, 15 pages.
Belaghzal et al., “Hi-C 2.0: An Optimized Hi-C Procedure for High-Resolution Genome-Wide Mapping of Chromosome Conformation,” Methods, Jul. 1, 2017, 123:56-65, 20 pages.
Belton et al., “Hi-C: A comprehensive technique to capture the conformation of genomes,” Methods, Nov. 2012, 58(3):268-276, 16 pages.
Bentzen et al., “Large-scale detection of antigen-specific T cells using peptide-MHC-I multimers labeled with DNA barcodes,” Nat Biotechnol., Oct. 2016, 34(10):1037-1045, 12 pages.
Chen et al. “Arrayed profiling of multiple glycans on whole living cell surfaces.” Analytical chemistry, Oct. 15, 2013, 85(22):11153-11158.
Fan et al., “Illumina Universal Bead Arrays,” Methods in Enzymology, 2006, 410:57-73.
Hadrup et al., “Parallel detection of antigen-specific T-cell responses by multidimensional encoding of MHC multimers,” Nat. Methods., Jul. 2009, 6(7), 520-526.
Hobro et al., “An evaluation of fixation methods: Spatial and compositional cellular changes observed by Raman imaging,” Vibrational Spectroscopy, Jul. 2017, 91:31-45.
Landegren et al., “A Ligase-Mediated Gene Detection Technique,” Science, 1988, 241(4869):1077-1080.
Mabruk et al., “In situ hybridization: detecting viral nucleic acid in formalin-fixed, paraffin-embedded tissue samples,” Expert Rev. Mol. Diagn., 2004, 4(5):653-661.
Mamedov et al., “Preparing unbiased T-cell receptor and antibody cDNA libraries for the deep next generation sequencing profiling,” Frontiers in Immunol., Dec. 23, 2013, 4(456):1-10.
Oksuz et al., “Systematic evaluation of chromosome conformation capture assays,” Nature Methods, Sep. 2021, 18:1046-1055.
Rohland et al., “Partial uracil-DNA-glycosylase treatment for screening of ancient DNA,” Phil. Trans. R. Soc. B, Jan. 19, 2015, 370(1660):20130624, 11 pages.
Schmidl et al., “ChIPmentation: fast, robust, low-input ChIP-seq for histones and transcription factors,” Nature Methods, Oct. 2015, 12:963-965.
Su et al., “Restriction enzyme selection dictates detection range sensitivity in chromatin conformation capture-based variant-to-gene mapping approaches,” bioRxiv, Dec. 15, 2020, 22 pages.
Streets et al., “Microfluidic single-cell whole-transcriptome sequencing,” Proc. Natl. Acad. Sci. U.S.A., 2014, 111(19):7048-7053.
Wang et al., “Multiplexed PCR-Free Detection of MicroRNAs in Single Cancer Cells Using a DNA-Barcoded Microtrough Array Chip,” Micromachines, 2019, 10(4):215, 11 pages.

REVERSIBLE FIXING REAGENTS AND METHODS OF USE THEREOF

CROSS-REFERENCE TO RELATED APPLICATIONS

The present application claims the benefit of priority to International Application No. PCT/US2020/066705, filed Dec. 22, 2020, U.S. Provisional Application No. 62/952,677, filed Dec. 23, 2019, and to U.S. Provisional Application No. 63/026,513, filed May 18, 2020, each of which are incorporated herein by reference.

FIELD

The present disclosure relates to fixing reagent compositions comprising bis-imidazole-carboxylate compounds and methods of their use to prepare reversibly fixed biological samples.

BACKGROUND

Biological samples containing a variety of biomolecules can be processed for various purposes, such as detection of a disease (e.g., cancer) and/or genotyping (e.g., species identification). Microfluidic technologies have been developed to facilitate processing biological samples by partitioning each sample (e.g., cells) into a discrete partition (e.g., a well or a droplet) that is separate from other partitions (e.g., a droplet fluidically isolated from other droplets). This partitioning into discrete partitions enables accurate control of the respective environments interacting with a biological sample. Further, biological samples partitioned in discrete partitions can be barcoded and subjected to chemical or physical processes such as heating, cooling, or chemical reactions. Thus, each discrete partition can contain its own separate sample and subject it to its own separate assay that can be qualitatively or quantitatively processed.

Biological samples, however, are unstable. When a biological sample is removed from its viable niche physical decomposition begins immediately. The degree of decomposition is determined by a number of factors including time, solution buffering conditions, temperature, source (e.g., certain tissues and cells a have higher levels of endogenous RNase activity), biological stress (e.g., enzymatic tissue dissociation can activate stress response genes), and physical manipulation (e.g. pipetting, centrifuging). The degradation includes important nucleic acid molecules (e.g., RNA), proteins, as well as higher-order 3D structure of molecular complexes, whole cells, tissues, organs, and organisms. The instability of biological samples is a significant obstacle for their use with partition-based assays (e.g., droplet-based or well-based single cell assays). Sample degradation greatly limits the ability to use such assays accurately and reproducibly with a wide range of available biological samples.

The problem of biological sample instability can be mitigated by fixing the sample using standard methods such as cryopreservation, dehydration (e.g., in methanol), high-salt storage (e.g., using RNAssist or RNAlater), and/or chemical fixing agents that create covalent crosslinks (e.g., paraformaldehyde or DSP). The ability to use such a fixed biological sample in an assay, particularly a partition-based assay, requires that the fixed biological sample can be rapidly and efficiently un-fixed, so that the relevant assay can be carried out before sample degradation occurs.

There remains a need for compositions and methods that provide reversible fixation of biological samples in a manner compatible with partition-based assays (e.g., microfluidic droplet-based assays or well-based assays).

SUMMARY

The present disclosure provides compositions and methods that allow for the reversible fixation of biological samples, and the use of such compositions and methods in partition-based assays (e.g., well- or droplet-based assays), such as gene expression profiling assays.

In at least one embodiment, the present disclosure provides a method for preparing a biological sample comprising contacting the sample with a first fixing reagent composition comprising a compound of formula (I)

(I)

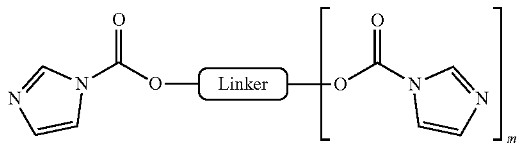

wherein, the "Linker" comprises an ethylene glycol moiety, and/or a linear or branched alkane moiety of 2-24 carbons; and m is 1 to 12; optionally, wherein m=1. In at least one embodiment, the "Linker" comprises: (a) a linear alkane moiety of 2-24 carbons; (b) an ethylene glycol moiety; (c) a disulfide bond; and/or (d) a branched alkane moiety.

In at least one embodiment of the method the compound of formula (I) is a compound of formula (II)

(II)

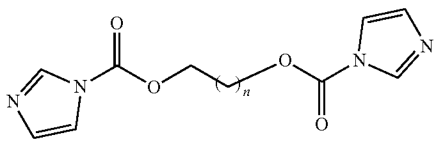

wherein n is 1 to 13.

In at least one embodiment of the method the compound of formula (I) is a compound of formula (III)

(III)

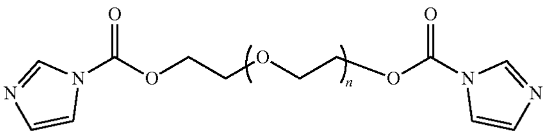

wherein n is 1 to 12.

In at least one embodiment of the method the compound of formula (I) is a compound of formula (IV)

(IV)

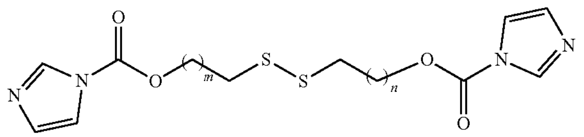

wherein m is 1 to 13, and n is 1 to 13.

In at least one embodiment of the method the compound of formula (I) is a compound of formula (V)

(V)

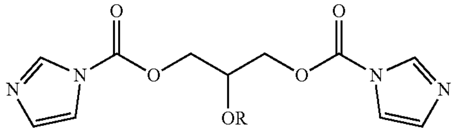

wherein R is selected from —H, —O(CO)—$CH_3$, and —O(CO)-imidazole.

In at least one embodiment of the method the compound of formula (I) is compound (6)

(6)

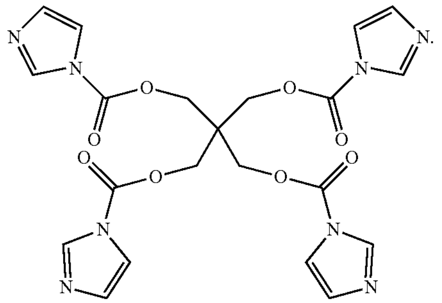

In at least one embodiment of the method, the first fixing reagent composition comprises: (a) the compound of formula (I) at a concentration of 50 mM or less, 25 mM or less, 15 mM or less, 10 mM or less, or 5 mM or less; and/or (b) DMSO at a concentration of 5% or less, 2.5% or less, or 1.5% or less.

In at least one embodiment of the method, contacting with the first fixing reagent composition at room temperature (RT) is for 3 h or less, 60 min or less, 30 min or less, 15 min or less, or 5 min or less.

In at least one embodiment the method further comprises contacting the sample with a second fixing reagent composition; optionally, wherein the second fixing reagent composition comprises paraformaldehyde; optionally, wherein the paraformaldehyde concentration is 1% or less.

In at least one embodiment of the method, the first fixing reagent composition comprises a compound of formula (II)

(II)

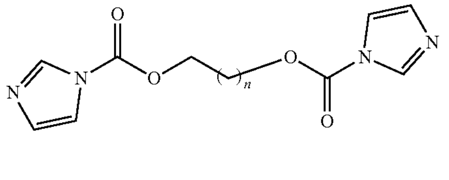

wherein n is 1 to 13; and the second fixing reagent composition comprises a compound of formula (III):

(III)

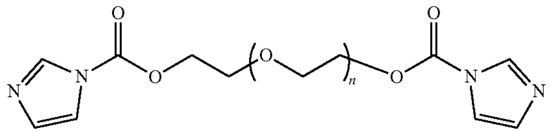

wherein n is 1 to 12.

In at least one embodiment of the method, the first fixing reagent composition comprises a compound of formula (III), wherein n is 1 to 12; and the second fixing reagent composition comprises a compound of formula (II), wherein n is 1 to 13.

In at least one embodiment of the method, the method further comprises contacting the sample with an unfixing agent; optionally, wherein the unfixing agent comprises: (a) a compound capable of cleaving a carbamate bond; optionally, wherein the compound capable of cleaving a carbamate bond selected from DETA, EDA, hydrazine monohydrate, a carboxyesterase, or a combination thereof; (b) a compound capable of cleaving a disulfide bond; optionally, wherein the compound capable of cleaving a disulfide bond is DTT; and/or (c) a compound capable of reversing paraformaldehyde fixation.

In at least one embodiment, the present disclosure also provides a composition comprising a fixed biological sample, wherein the sample comprises crosslinked biomolecules of formula (Ia)

(Ia)

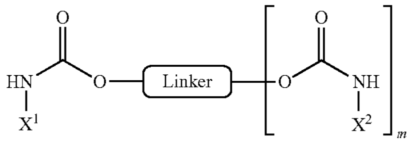

wherein, $X^1$ and $X^2$ are amine-bearing moieties of the same or different biomolecules of the sample; and "Linker" comprises an ethylene glycol moiety, and/or a linear or branched alkane moiety of 2-24 carbons; and m is 1 to 12. In at least one embodiment, the "Linker" comprises: (a) a linear alkane moiety of 2-24 carbons; (b) an ethylene glycol moiety; (c) a disulfide bond; and/or (d) a branched alkane moiety.

In at least one embodiment of the composition, the fixed biological sample comprises crosslinked biomolecules of formula (IIa)

(IIa)

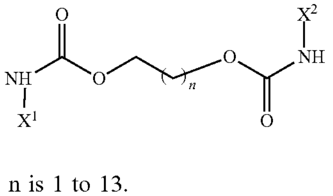

wherein, n is 1 to 13.

In at least one embodiment of the composition, the fixed biological sample comprises crosslinked biomolecules of formula (IIIa)

(IIIa)

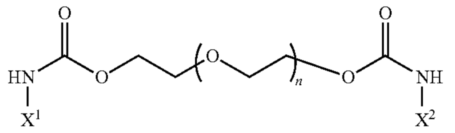

wherein, n is 1 to 12.

In at least one embodiment of the composition, the fixed biological sample comprises crosslinked biomolecules of formula (IVa)

(IVa)

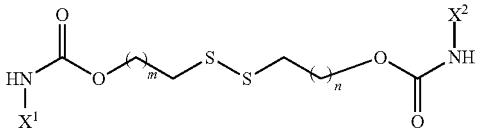

wherein m is 1 to 13, and n is 1 to 13.

In at least one embodiment of the composition, the fixed biological sample comprises crosslinked biomolecules of formula (Va)

(Va)

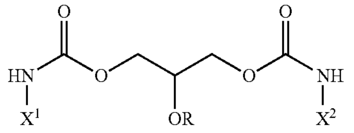

wherein R is selected from —H, —O(CO)—$CH_3$, and —O(CO)-imidazole.

In at least one embodiment of the composition, the fixed biological sample comprises crosslinked biomolecules of formula (VIa)

(VIa)

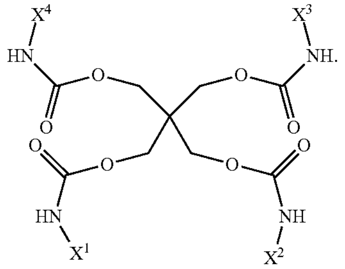

In at least one embodiment of the composition, the fixed biological sample is derived from a tissue sample, a biopsy sample, or a blood sample; optionally, wherein the fixed biological sample is a single cell.

In at least one embodiment of the composition, the fixed biological sample has been fixed with a fixing reagent composition comprising a compound of any one of formulas (I), (II), (III), (IV), (V), or compounds (6).

In at least one embodiment of the composition, the fixed biological sample is provided in a discrete partition (e.g., provided or encapsulated in a discrete droplet or provided in a well) with a lysis and/or an unfixing agent; optionally, wherein the unfixing agent comprises a compound capable of cleaving a carbamate bond; optionally, wherein the compound capable of cleaving a carbamate bond selected from DETA, EDA, hydrazine monohydrate, a carboxyesterase, or a combination thereof.

In at least one embodiment of the composition, the fixed biological sample is provided in a discrete partition (e.g., provided or encapsulated in a discrete droplet or provided in a well), wherein the discrete partition further comprises a support (e.g., a bead); optionally, wherein the unfixing agent is contained in a support (e.g., a bead).

In at least one embodiment of the composition, the fixed biological sample is provided in a discrete partition (e.g., provided or encapsulated in a discrete droplet or provided in a discrete well), wherein the discrete partition further comprises assay reagents; optionally, wherein the assay reagents are provided as part of a support (e.g., a bead) or contained in a support (e.g., a bead).

In at least one embodiment of the composition, the fixed biological sample is provided in a discrete partition (e.g., provided or encapsulated in a discrete droplet or provided in a discrete well), wherein the discrete partition further comprises a barcode optionally, wherein the barcode is contained as part of a support (e.g., a bead).

In at least one embodiment, the present disclosure also provides an assay method comprising: (a) generating a discrete partition comprising a fixed biological sample (e.g., a droplet comprising or encapsulating a fixed biological sample), a lysis and/or an unfixing agent, and assay reagents, wherein the fixed sample comprises crosslinks of formula (Ia)

(Ia)

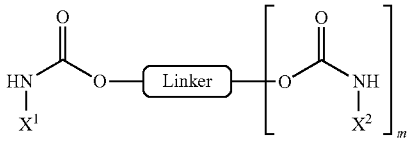

wherein, $X^1$ and $X^2$ are amine-bearing moieties of the same or different biomolecules of the sample; the "Linker" comprises an ethylene glycol moiety, and/or a linear or branched alkane moiety of 2-24 carbons; and m is 1 to 12; the unfixing agent comprises a compound capable of cleaving a carbamate bond; optionally, wherein the compound capable of cleaving a carbamate bond selected from DETA, EDA, hydrazine monohydrate, a carboxyesterase, or a combination thereof; and (b) detecting analytes from the reaction of the assay reagents and the un-fixed biological sample.

In at least one embodiment, the present disclosure also provides a kit comprising: assay reagents; and a fixing reagent composition comprising a compound of formula (I)

(I)

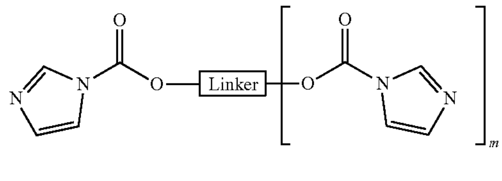

wherein, the "Linker" comprises an ethylene glycol moiety, and/or a linear or branched alkane moiety of 2-24 carbons; and m is 1 to 12. In at least one embodiment, the "Linker" comprises: (a) a linear alkane moiety of 2-24 carbons; (b) an ethylene glycol moiety; (c) a disulfide bond; and/or (d) a branched alkane moiety. In at least one embodiment, the fixing reagent composition comprises a compound of any one of formulas (II), (Ill), (IV), (V), or compound (6).

BRIEF DESCRIPTION OF THE DRAWINGS

A better understanding of the novel features and advantages of the present disclosure will be obtained by reference to the following detailed description that sets forth illustrative embodiments, in which the principles of the disclosure are utilized, and the accompanying drawings (also "Figure" and "FIG." herein), of which.

DETAILED DESCRIPTION

Figure 1:
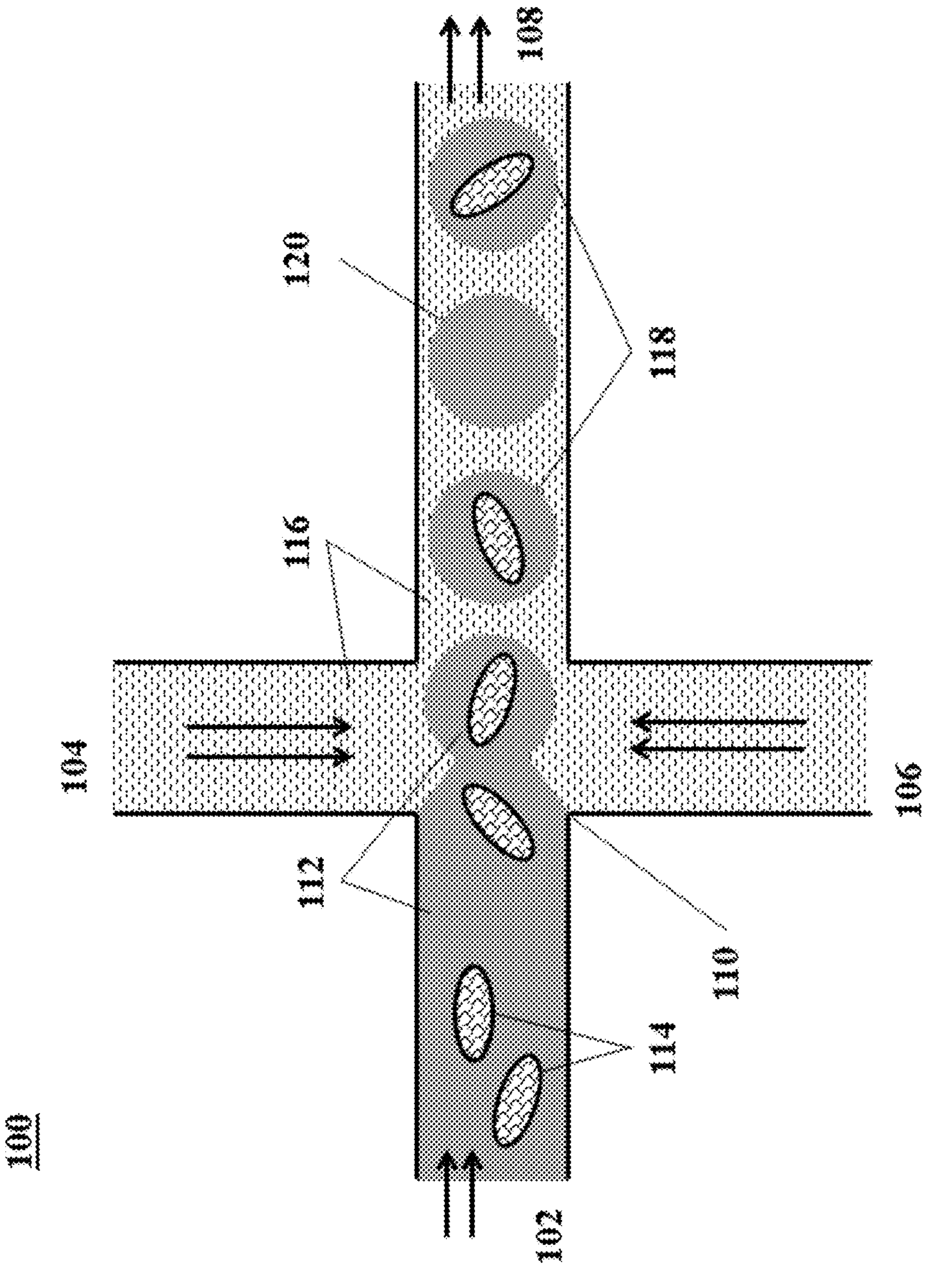
FIG. 1 shows an example of a microfluidic channel structure for partitioning individual biological particles.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the embodiments of the disclosure. The upper and lower limits of these smaller ranges may independently be included in the smaller ranges, and are also encompassed within the embodiments of the disclosure, subject to any specifically excluded limit in the stated range. Where the stated range includes one or both of these limits, ranges excluding (i) either or (ii) both of those included limits are also included in the embodiments of the disclosure. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning—A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel").

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present disclosure pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

A. Fixing Reagent Compositions of Bis-Imidazole-Carboxylate Compounds

The present disclosure provides compositions and methods that allow for the reversible fixation of biological samples. The ability to reversible fix biological samples is based on the use of a fixing reagent composition comprising a bis-imidazole-carboxylate compound of general formula (I):

(I)

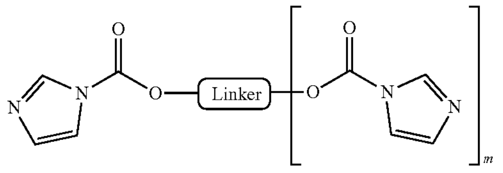

The "Linker" depicted schematically in formula (I) can be any chemical group capable of covalently linking the imidazole carbon/late moieties. In at least one embodiment of the compound of formula (I), "Linker" comprises an ethylene glycol moiety, and/or a linear or branched alkane moiety of 2-24 carbons; and m is 1 to 12.

The compounds of formula (I) can be prepared by reacting carbonyl diimidazole (CDI) with a desired bis-hydroxy linker compound as depicted in Scheme 1.

Scheme 1

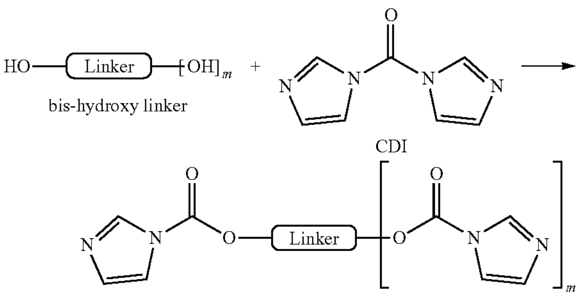

(I)

Typical CDI synthesis reaction conditions can be used, e.g., 1.5-fold to 4-fold excess CDI in dichloromethane, 16 h at RT, as described in Example 1. The general CDI-based reaction of Scheme 1 can be used with a wide range of bis-hydroxy linker compounds (e.g., glycerol, bis-hydroxy-alkanes, PEG compounds, hydroxy-substituted branched-alkyl compounds) to provide a wide range of fixation reagent compounds of formula (I).

Accordingly, in at least one embodiment, the present disclosure also provides a fixing reagent composition, wherein the compound of formula (I) is selected from:

(a) a compound of formula (II)

(II)

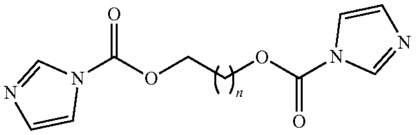

wherein n is 1 to 13;

(b) a compound of formula (III)

(III)

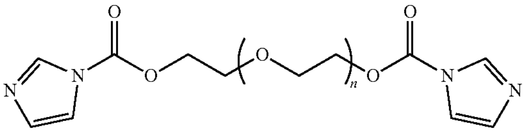

wherein, n is 1 to 12;

(c) a compound of formula (IV)

(IV)

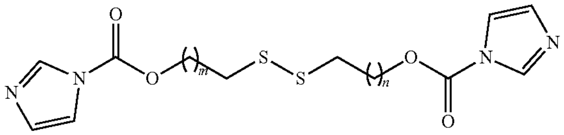

wherein m is 1 to 13, and n is 1 to 13;

(d) a compound of formula (V)

(V)

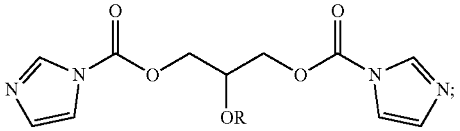

wherein R is —H, —O—(CO)—$CH_3$, or —O—(CO)-imidazole or (e) a compound (6)

(6)

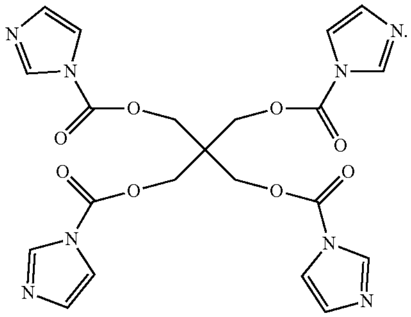

Additional specific bis-imidazole-carboxylate compounds of formulas (I), (II), (Ill), (IV), and (V) are contemplated. A non-exhaustive list of such compounds useful as fixing reagents in the compositions and methods of the present disclosure are provided in Table 1.

TABLE 1

(2a)

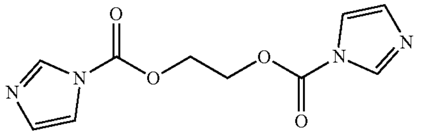

ethane-1,2-diyl bis(1H-imidazole-1-carboxylate)

TABLE 1-continued
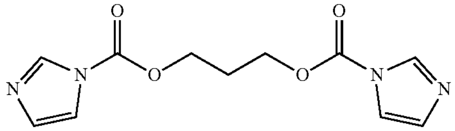 [SMILES: O=C(OCCCOC(=O)n1ccnc1)n1ccnc1]
(2b)
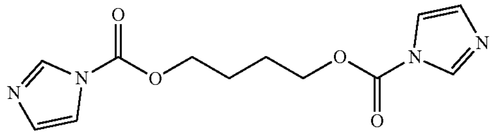 [SMILES: O=C(OCCCCOC(=O)n1ccnc1)n1ccnc1]
(2c)
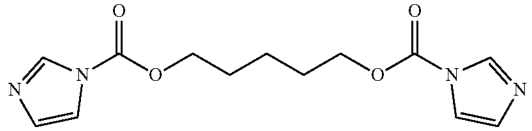 [SMILES: O=C(OCCCCCOC(=O)n1ccnc1)n1ccnc1]
(2d)
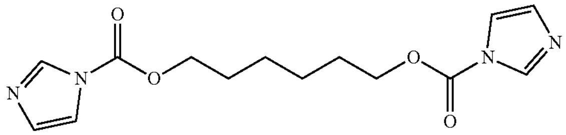 [SMILES: O=C(OCCCCCCOC(=O)n1ccnc1)n1ccnc1]
(2e)
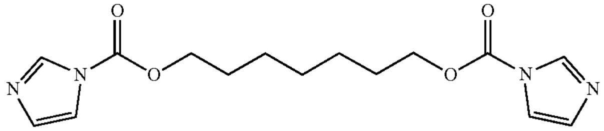 [SMILES: O=C(OCCCCCCCOC(=O)n1ccnc1)n1ccnc1]
(2f)
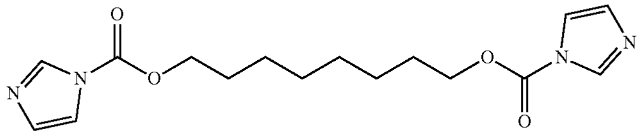 [SMILES: O=C(OCCCCCCCCOC(=O)n1ccnc1)n1ccnc1]
(2g)
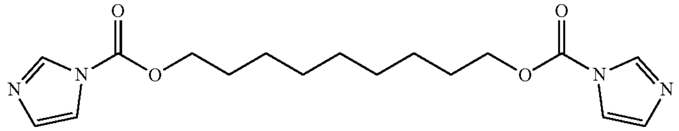 [SMILES: O=C(OCCCCCCCCCOC(=O)n1ccnc1)n1ccnc1]
(2h)
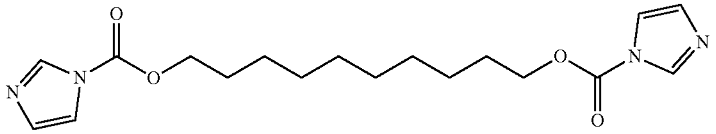 [SMILES: O=C(OCCCCCCCCCCOC(=O)n1ccnc1)n1ccnc1]
(2i)
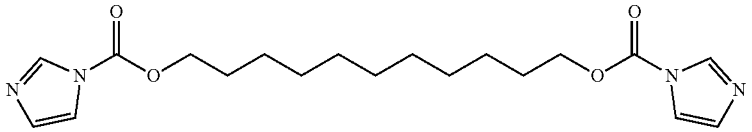 [SMILES: O=C(OCCCCCCCCCCCOC(=O)n1ccnc1)n1ccnc1]
(2j)
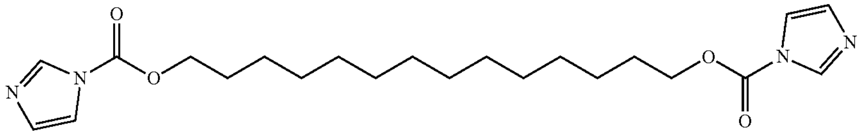 [SMILES: O=C(OCCCCCCCCCCCCCCOC(=O)n1ccnc1)n1ccnc1]
(2k)
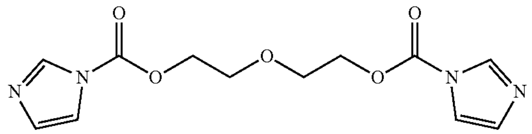
(3a)

TABLE 1-continued
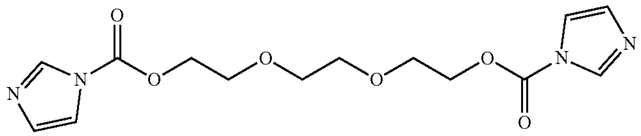 [SMILES: O=C(OCCOCCOCCOC(=O)n1ccnc1)n1ccnc1]
(3b)
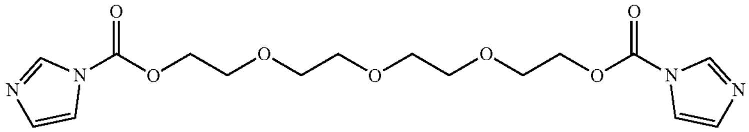 [SMILES: O=C(OCCOCCOCCOCCOC(=O)n1ccnc1)n1ccnc1]
(3c)
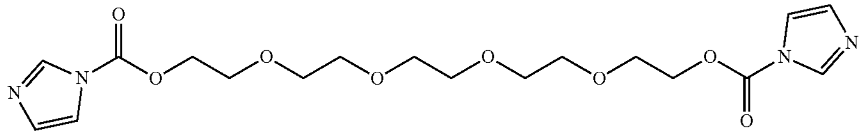 [SMILES: O=C(OCCOCCOCCOCCOCCOC(=O)n1ccnc1)n1ccnc1]
(3d)
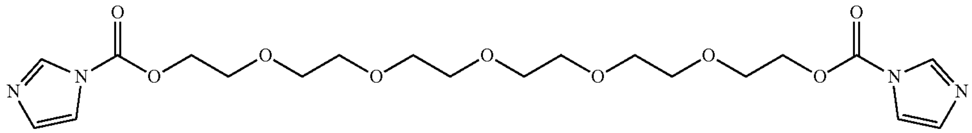 [SMILES: O=C(OCCOCCOCCOCCOCCOCCOC(=O)n1ccnc1)n1ccnc1]
(3e)
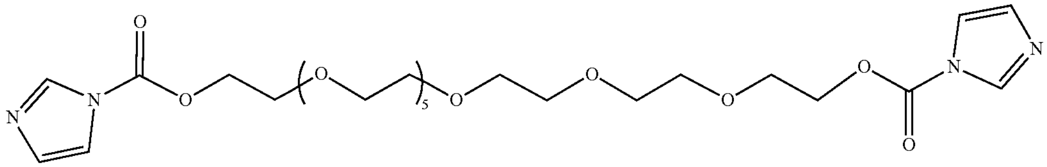
(3f)
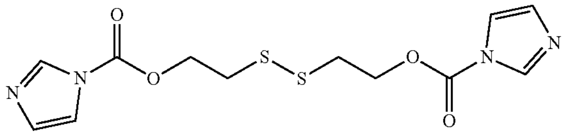 [SMILES: O=C(OCCSSCCOC(=O)n1ccnc1)n1ccnc1]
(4a)
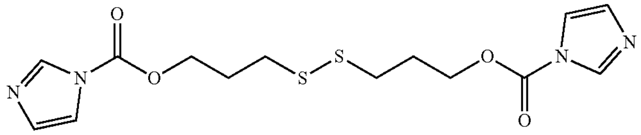 [SMILES: O=C(OCCCSSCCCOC(=O)n1ccnc1)n1ccnc1]
(4b)
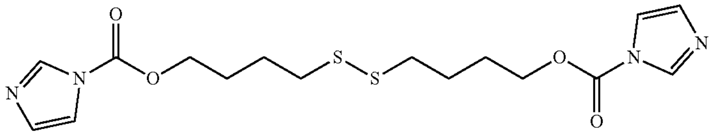 [SMILES: O=C(OCCCCSSCCCCOC(=O)n1ccnc1)n1ccnc1]
(4c)
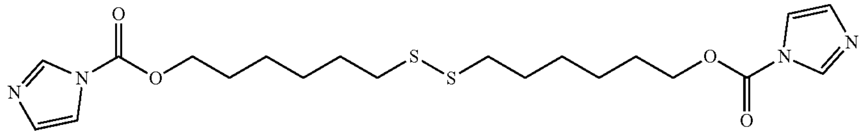 [SMILES: O=C(OCCCCCCSSCCCCCCOC(=O)n1ccnc1)n1ccnc1]
(4d)
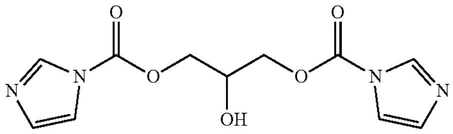 [SMILES: O=C(OCC(O)COC(=O)n1ccnc1)n1ccnc1]
(5a)

TABLE 1-continued

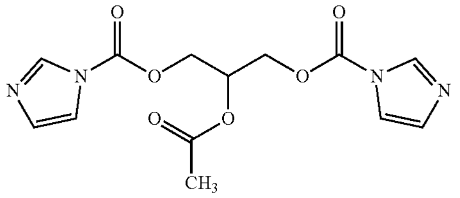 [SMILES: CC(=O)OC(COC(=O)n1ccnc1)COC(=O)n1ccnc1]

(5b)

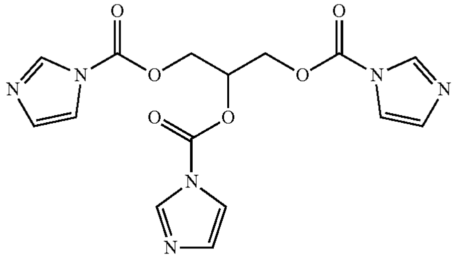 [SMILES: O=C(OCC(COC(=O)n1ccnc1)OC(=O)n1ccnc1)n1ccnc1]

(5c)

B. Use of Bis-Imidazole-Carboxylate Compounds to Prepare Biological Samples

The bis-imidazole-carboxylate compounds of formula (I) (and sub-genus compounds of formulas (II), (Ill), (IV), (V) and Table 1) provide the advantageous technical effect of rapidly and efficiently reacting with the amine-bearing moieties of biomolecules in a biological sample (e.g., protein lysine and arginine side-chains; nucleic acid adenine and guanine nucleobases) to form bis-carbamate crosslinks. A generalized biological sample fixation reaction using a fixation reagent of formula (I) is shown in Scheme 2.

Scheme 2

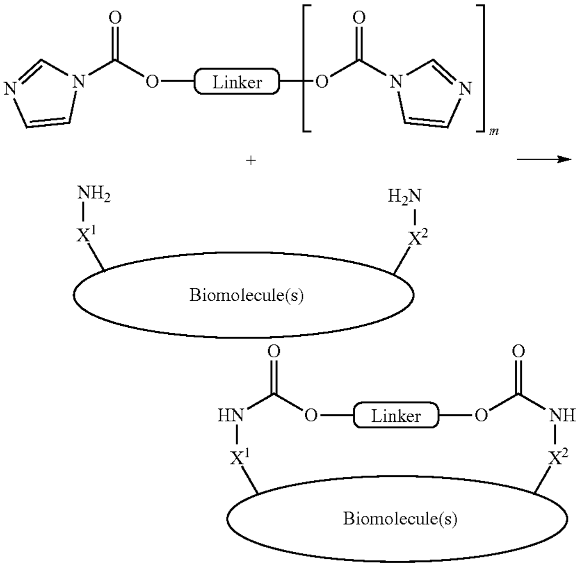

As used herein, the term "biological sample," refers to any sample of biological origin that includes a biomolecule. The term "biomolecule" is intended to encompass proteins, peptides, nucleic acids, carbohydrates, lipids, and all other biological macromolecules. Biological samples used in the methods and compositions of the present disclosure include blood and other liquid samples of biological origin, solid tissue samples such as a tissue sample (i.e., tissue specimen), a biopsy (i.e., a biopsy specimen), or tissue cultures or cells derived therefrom and the progeny thereof. This includes samples that have been manipulated in any way after isolation from the biological source, such as by treatment with reagents (e.g., fixation reagents, thereby generating a fixed biological sample); samples such as tissues that are embedded in medium (e.g., paraffin); sectioned tissue sample (e.g., sectioned samples that are mounted on a solid substrate such as a glass slide); washed; or enrichment for certain cell populations, such as cancer cells, neurons, stem cells, etc. The term also encompasses samples that have been enriched for particular types of molecules, e.g., nucleic acids, polypeptides, etc. Biological sample is also intended to include a clinical sample, including tissue obtained by surgical resection, tissue obtained by biopsy, cells in culture, cell supernatants, cell lysates, tissue samples (i.e., tissue specimens), organs, bone marrow, blood, plasma, serum, and the like. A biological sample can also include a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample having cells (e.g., cancer cells) from a patient.

The term "fixed" as used herein with regard to biological samples refers to a state of being preserved from decay and/or degradation. "Fixation" refers to a process that results in a fixed sample, and can include contacting the biomolecules within a biological sample with a fixation reagent (or "fixative") for some amount of time, whereby the fixation reagent reacts with the biomolecules of the sample to form covalent crosslinks between chemical moieties of the biomolecules (e.g., amine-bearing moieties). The reaction of the bis-imidazole-carboxylate fixation reagents with the amine-bearing moieties of biomolecules is described in greater detail below.

Herein, "un-fixed" refers to the processed condition of a cell, a plurality of cells, a tissue sample or any other biological sample that is characterized by a prior state of fixation followed by a reversal of the prior state of fixation. For instance, an un-fixed cell may also be referred to as a "previously fixed" cell. In one embodiment, an un-fixed cell is characterized by broken or reversed covalent bonds in the biomolecules of the cell(s) or sample, where such covalent bonds were previously formed by treatment with a fixation agent described herein.

The general biological sample fixation reaction of Scheme 2 can be carried out using a fixing reagent composition comprising compounds of formula (I) under standard aqueous conditions typically used for fixation of biological samples. The amount of time a biological sample is contacted with a fixative to provide a fixed biological sample depend on the temperature, the nature of the sample, and the fixative used. For example, as described elsewhere herein and the Examples an isolated sample of cells is incubated with an aliquot of a solution of the compound (2a) at a concentration of e.g., 5-15 mM for 30-60 minutes at room temperature, before quenching with excess buffer. The resulting fixed biological sample is preserved and can be stored under typical cryopreservation conditions for days, weeks, or months, before use.

Accordingly, in at least embodiment, the present disclosure provides a method for preparing a biological sample comprising contacting the sample with a first fixing reagent composition comprising a compound of formula (I)

(I)

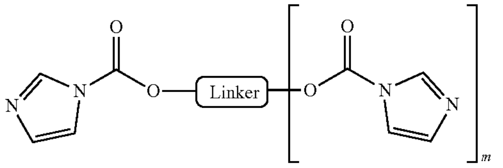

wherein, "Linker" comprises an ethylene glycol moiety, and/or a linear or branched alkane moiety of 2-24 carbons; and m is 1 to 12. It is further contemplated that the methods can be carried out wherein the compound of formula (I) is a compound of any of formulas (II), (Ill), (IV), or (V), or compound (6), or any one or more of the bis-imidazole-carboxylate compounds disclosed in Table 1.

For example, a biological fixation reaction of the method can be carried out using a fixing reagent compound of formula (IV) as depicted Scheme 3.

Scheme 3

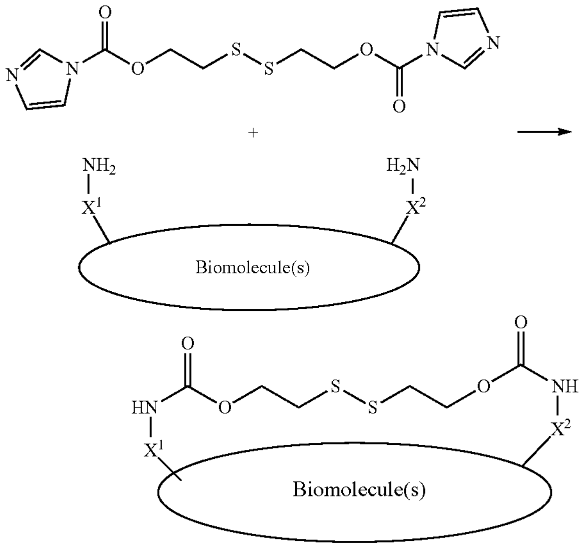

Similarly, a biological fixation reaction can be carried out using a fixation reagent compound of formula (I) wherein m=3. Such a reaction, which can be carried out using a reagent such as compound (6), results in branched bis-carbamate crosslinks between biomolecules of the biological samples, as shown by the generalized reaction of Scheme 4, Scheme 4

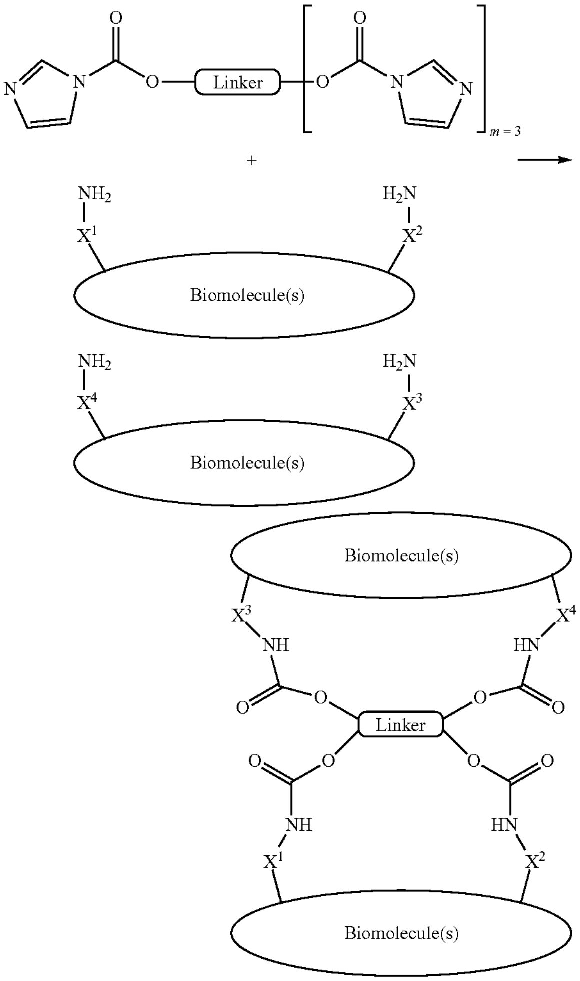

C. Methods Using Combinations of Fixing Reagents

It is also contemplated that a mixture of the bis-imidazole carbon/late fixing reagent compounds of formula (I) can be used in the methods of the present disclosure. For example, in at least one embodiment, the fixing reagent composition comprises a compound of formula (II), which comprises a Linker having an alkyl chain, and a compound of formula (III), which comprising a Linker having an ethylene glycol chain. Without being bound by theory, it is contemplated that the compounds of formula (III) having an ethylene glycol chain "Linker" moiety are more soluble in aqueous solution and well-suited for fixing biomolecules on the surfaces of cells. In contrast, it is contemplated that the fixing reagent compounds of formula (II), which comprise a more hydrophobic alkyl chain in the Linker moiety are less soluble in aqueous environments and better suited for fixing biomolecules in interior of a cell. Accordingly, in at least one embodiment, the method can be carried out wherein the method comprises contacting the sample with a first fixing reagent composition comprising a compound of formula (II) and a compound of formula (III). Generally, the selection of the particular bis-imidazole-carboxylate compounds to be used in a fixing reagent composition useful in methods for preparing a biological sample is guided by factors typically considered in the development of sample preparation methods. Such factors include, but are not limited to, reagent solubility and compatibility with the type of biological sample, the conditions used, and the desired amount of fixation/preservation.

Further, the bis-imidazole carboxylate fixing reagent compounds of formula (I) can be used in combination with a second fixing reagent compound that does not form bis-carboxylate crosslinks. Examples of fixing reagent compounds that can be used in combination with the bis-imidazole carboxylate fixing reagent compounds of formula (I) include but are not limited to aldehyde fixatives (e.g., formaldehyde, also commonly referred to as "paraformaldehyde" and "formalin"; glutaraldehyde; etc.), imidoesters, NHS (N-Hydroxysuccinimide) esters, and the like.

In some embodiments, the second fixing reagent useful in the methods of the present disclosure is paraformaldehyde (or "PFA"). Generally, the term "paraformaldehyde" in the context of a fixative is used interchangeably with "formaldehyde" and "formalin." Thus, a PFA-fixed biological sample may also be referred to as formalin-fixed or formaldehyde-fixed. Protocols and methods for the use of PFA as a fixation reagent with biological samples are well known in the art, and can be used in the methods and compositions of the present disclosure.

PFA is a strong fixative that crosslinks the nucleobases of nucleic acids in a sample with animal bonds that are difficult to reverse (or un-fix) under conditions that also maintain the integrity of the nucleic acids for further analysis—e.g., in an RNA profiling assay. Typically, a fixing reagent solution of 4% PFA is used for preparing biological samples. It is contemplated that a significantly lower concentration of PFA can be used in a method of preparing a biological sample when used in combination with a bis-imidazole carboxylate fixing reagent compounds of formula (I). For example, a biological sample can be treated with first fixing reagent composition comprising compound (2a), then treated with a second fixing reagent composition comprising a 1% PFA. Without intending to be bound by theory, it is believed that the initial treatment with the bis-imidazole carboxylate fixing reagent of compound (2a) results in the fixation of available mRNA with DETA-reversible bis-carbamate crosslinks, and the secondary treatment with 1% PFA stabilizes proteins and other biomolecules with aminal cross-links. The use of only 1% PFA, however, provides sufficient sample stability in view of the prior treatment with compound (2a), for some period of time (e.g., >7 days), and also allows for sufficient ability to un-fix the sample and carry out assays, such as RNA expression profiling. Accordingly, in at least one embodiment, the present disclosure provides a method for preparing a biological sample comprising contacting the sample with a first fixing reagent composition comprising a compound of formula (I) and a second fixing reagent composition, wherein the second fixing reagent composition comprises PFA at concentration of 2% or less, 1% or less, or 0.5% or less.

Conditions for reversing the effects of PFA fixation of a biological sample are known in the art, however, these conditions tend to be harsh. See e.g., WO2001/46402; US2005/0014203A1, and US2009/0202998A1. For example, treatment of PFA-treated tissue samples includes heating to 60-70 C in Tris buffer for several hours, and yet typically results in removal of only a fraction of the PFA-induced crosslinks. The use of such harsh un-fixing treatment conditions can result in permanent damage to biomolecules, particularly nucleic acids, in the sample. Less harsh techniques and conditions have been proposed that utilize un-fixing compounds capable of catalytically cleaving the animal bond that result from PFA fixation are described in e.g., Karmakar et al., "Organocatalytic removal of formaldehyde adducts from RNA and DNA bases," Nature Chemistry, 7: 752-758 (2015); US 2017/0283860A1; and US 2019/0135774A1. See e.g., Karmakar et al., "Organocatalytic removal of formaldehyde adducts from RNA and DNA bases," Nature Chemistry, 7: 752-758 (2015); US 2017/0283860A1; and US 2019/0135774A1. Accordingly, in at least one embodiment of the methods of the present disclosure it is contemplated that the method can further comprise use of an catalytic unfixing agent compound capable reversing PFA fixation. Exemplary catalytic compounds capable of reversing PFA fixation are disclosed in Table 2 below.

TABLE 2

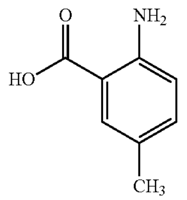

(7a)

2-amino-5-methylbenzoic acid
(CAS No. 2941-78-8; Sigma-Aldrich)

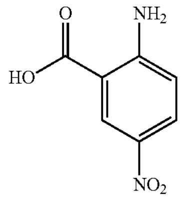

(7b)

2-amino-5-nitrobenzoic acid
(CAS No. 616-79-5; Sigma-Aldrich)

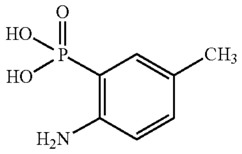

(7c)

(2-amino-5-methylphenyl)phosphonic acid
(CAS 69675-98-5; Ambeed Inc.)

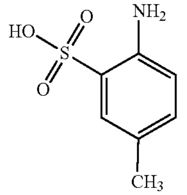

(7d)

2-amino-5-methylbenzenesulfonic acid
(CAS No. 88-44-8; Sigma-Aldrich)

TABLE 2-continued (7e)

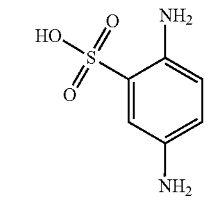 [SMILES: Nc1ccc(N)c(S(=O)(=O)O)c1]

2,5-diaminobenzenesulfonic acid
(CAS No. 88-45-9; Sigma-Aldrich)

(7f)

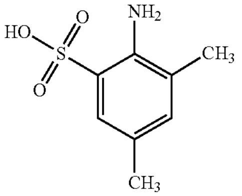

2-amino-3,5-dimethylbenzenesulfonic acid
(CAS No. 88-22-2; TCI Co. Ltd., Tokyo, JP)

(7g)

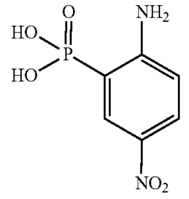 [SMILES: Nc1ccc([N+](=O)[O-])cc1P(=O)(O)O]

(2-amino-5-nitrophenyl)phosphonic acid (7h)

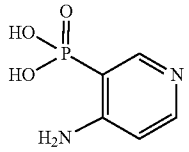 [SMILES: Nc1ccncc1P(=O)(O)O]

(4-aminopyridin-3-yl)phosphonic acid (7i)

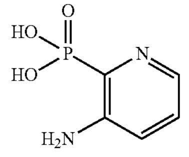

(3-aminopyridin-2-yl)phosphonic acid (7j)

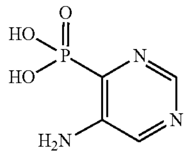

(5-aminopyrimidin-4-yl)phosphonic acid

TABLE 2-continued (7k)

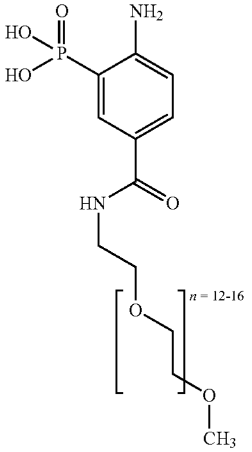

(2-amino-5-{[2-(2-poly-ethoxy)ethyl]carbamoyl}
phenyl)phosphonic acid (7l)

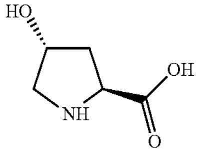

(2S,4R)-4-hydroxypyrrolidine-2-carboxylic acid
("trans-4-hydroxy-L-proline;" CAS No. 51-35-4; Sigma-Aldrich)

(7m)

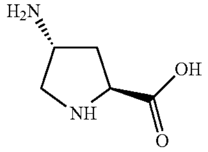

(2S,4R)-4-aminopyrrolidine-2-carboxylic acid
("trans-4-aminoproline;" CAS No. 16257-88-8)

(7n)

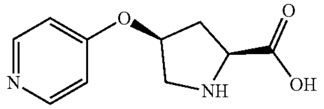 [SMILES: O=C(O)[C@@H]1C[C@H](Oc2ccncc2)CN1]

(2S,4S)-4-[(pyridin-4-yl)oxy]pyrrolidine-2-carboxylic acid
(CAS No. 2309431-82-9; Enamine Ltd.)

(7o)

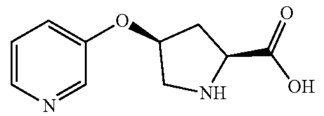 [SMILES: O=C(O)[C@@H]1C[C@H](Oc2cccnc2)CN1]

(2S,4S)-4-[(pyridin-3-yl)oxy]pyrrolidine-2-carboxylic acid
("cis-m-O-Py-Pro")

Compounds (7a)-(7f), (7l), and (7n) are commercially available. The compounds (7g), (7 h), (7i), (7j), (7k), (7m), and (7o) can be prepared from commercially available reagents using standard chemical synthesis techniques well-known in the art. See e.g., Crisalli et al., "Importance of ortho Proton Donors in Catalysis of Hydrazone Formation," *Org. Lett.* 2013, 15, 7, 1646-1649.

Briefly, compound (7h) can be prepared in a 2-step synthesis from a commercially available compound as follows. Step 1: Diethyl (4-aminopyridin-3-yl)phosphonate is prepared according to the procedure described in Guilard, R. et al. *Synthesis,* 2008, 10, 1575-1579. Briefly, to a solution of 3-bromopyridine-4-amine (2.5 g, 14.5 mmol, 1 equiv) (CAS:13534-98-0, Sigma Aldrich) in ethanol (58 mL) is added diethyl phosphite (2.2 mL, 17.3 mmol, 1.2 equiv.) triethylamine (3 mL, 1.5 equiv), $PPh_3$ (1.1 g, 4.3 mmol, 30 mol %) and $Pd(OAc)_2$ (0.39 g, 1.73 mmol, 12 mol %). The reaction mixture is purged with Argon for 5 min. After heating to reflux for 24 h, the reaction mixture is cooled to room T and concentrated in vacuo. The residue is purified by silica gel chromatography (MeOH/DCM) to yield diethyl (4-aminopyridin-3-yl)phosphonate NMR (80 MHz, $CDCl_3$): δ=1.15 (t, 6H, $CH_3$), 4.18-3.69 (m, 4H, $CH_2$), 5.99 (br-s, 2H, $NH_2$), 6.49 (d, 1H), 8.03-7.93 (m, 1H), 8.22 (d, 1H)). Step 2: The precursor compound of Step 1, diethyl (4-aminopyridin-3-yl)phosphonate (0.35 g, 1.52 mmol, 1 equiv) is suspended in 6 N HCl (aq.) (8 mL). After refluxing for 12 h, the reaction mixture is concentrated in vacuo. The residue is washed with DCM, ether and conc in vacuo to afford the target 4-aminopyridin-3-yl-phosphonic acid of compound (7h) NMR (80 MHz, $D_2O$): δ=6.85-6.55 (m, 1H), 8.05-7.94 (m, 1H), 8.40-8.26 (m, 1H) 0.

Compound (7k) can be prepared in a 4-step synthesis from a commercially available compound as follows. Step 1: To a solution of methyl 4-amino-3-iodobenzoate (2 g, 7.2 mmol, 1 equiv) (CAS:19718-49-1, Sigma Aldrich) in acetonitrile (20 mL) is added triethyl phosphite (1.9 mL, 10.8 mmol, 1.5 equiv.) and $Pd(OAc)_2$ (0.16 g, 0.72 mmol, 10 mol %). This reaction mixture is purged with Argon for 5 min. After heating to reflux for 18 h, the reaction mixture is cooled to room temperature and conc. in vacuo. The residue was partitioned between ethyl acetate and water, and the organic layer was dried with MgSO4 and conc. in vacuo. The crude mixture was purified by silica gel chromatography (ethyl acetate/hexane) to yield methyl-4-amino-3-(diethoxyphosphoryl)benzoate ($^1H$ NMR (500 MHz, DMSO-$d_6$): δ=1.27 (t, 6H, $CH_3$), 3.80 (s, 3H, OMe), 3.97-4.11 (m, 4H, $OCH_2$), 6.76 (br-s, 2H, $NH_2$), 6.80-6.83 (m, 1H), 7.82 (dd, 1H), 7.98 (dd, 1H)). Step 2: To a solution of methyl-4-amino-3-(diethoxyphosphoryl)benzoate (0.96 g, 3.15 mmol, 1 equiv) in THF:methanol:water (10 mL:2.5 mL, ratio: 4:1:1) from Step 1 is added solid LiOH (0.45 g, 18.9 mmol, 6 equiv). After heating at 60° C. for 6 h, the reaction mixture is concentrate in vacuo, acidified to pH 2 and solid precipitated out. The solid is filtered and washed twice with 1N HCl to yield 4-amino-3-(diethoxyphosphoryl)benzoic acid ((0.49 mg, 57% yield). $^1H$ NMR (80 MHz, $CDCl_3$): δ=1.34 (t, 6H, $CH_3$), 3.85-4.38 (m, 4H, $OCH_2$), 5.74 (br-s, 2H, $NH_2$), 6.50-6.76 (m, 1H), 7.86-8.36 (m, 2H)). Step 3: To a solution of 4-amino-3-(diethoxyphosphoryl)benzoic acid (0.25 g, 0.92 mmol, 1 equiv) from Step 2 and PEG-amine (0.75 g, 1.01 mmol, 1.1 equiv) in MeOH (4.6 mL) is added 4-(4,6-dimethoxy-1,3,5-triazin-2-yl)-4-methylmorpholinium chloride (DMTMM) under Argon. After stirring at room temperature for 18 h, the reaction mixture is concentrated in vacuo, and the residue is partitioned between DCM and brine. The organic layer was washed with 1N HCl, saturated sodium bicarbonate solution, dried with MgSO4, filtered and conc. in vacuo to yield PEG-amide ethyl phosphonate (0.35 g, 36% yield) which was subjected without purification to the next step. $^1H$ NMR (80 MHz, $CD_3OD$): δ=1.34 (t, 6H, $CH_3$), 3.44 (s, 3H, OCH3), 3.56-3.91 (m, PEG), 4.02-4.22 (m, 4H, $OCH_2$), 6.62-6.93 (m, 1H), 7.74-8.45 (m, 2H). Step 4: PEG-amide ethyl phosphonate (0.35 g, 0.36 mmol, 1 equiv) from Step 3 is suspended in 6 N HCl (aq.) (8 mL). After refluxing for 12 h, the reaction mixture is concentrated in vacuo. The residue is washed with MeOH, DCM and conc in vacuo to afford the PEG-amide phosphonic acid of compound (7k) ((0.31 g, 94% yield). $^1H$ NMR (80 MHz, $D_2O$): δ=3.02-4.06 (m, PEG), 7.36-7.52 (m, 1H), 7.99-8.09 (m, 1H)).

Compounds (7i) and (7j) can be prepared from similarly straightforward procedures. For example, compound (7i) can be prepared in 2-steps from 2-bromopyridin-3-amine (CAS Reg. #39856-58-1; Sigma-Aldrich, St. Louis, MO) as shown in the scheme below.

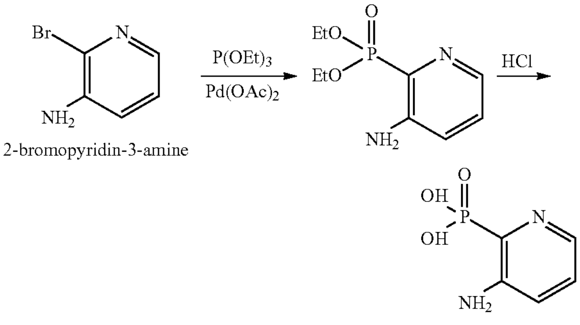

2-bromopyridin-3-amine (9)

Compound (7j) is prepared similarly in 2-steps from 4-bromopyrimidin-5-amine (CAS Reg. #849353-34-0; Ambeed, Inc., Arlington Heights, IL., USA) as shown in the scheme below.

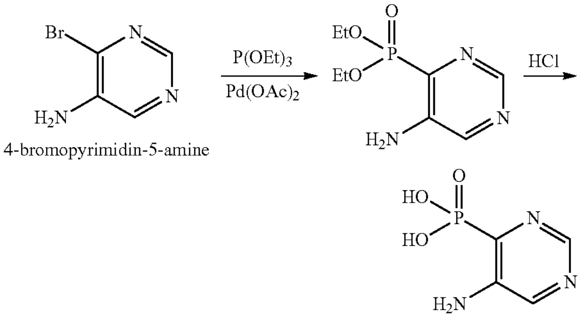

4-bromopyrimidin-5-amine (10)

The proline analog compounds (7m) and (7o) are prepared via a straightforward single step deprotection from commercially available protected precursor compounds. Accordingly, in at least one embodiment of the methods of the present disclosure that comprise the use of PFA, the method can further comprise contacting the sample with an unfixing agent capable of reversing PFA fixation, optionally, where the unfixing agent is selected from any one of compounds (7a)-(7o) shown in Table 2.

D. Compositions of Bis-Carbamate Crosslinked Biomolecules

As shown by the reactions depicted in Schemes 2, 3, and 4, the use of the bis-imidazole carboxylate compounds of formula (I) in a method of fixing a biological sample results in the formation of bis-carbamate crosslinks between amine-bearing moieties of the biomolecules of the sample, e.g., proteins and nucleic acids. The bis-carbamate crosslinks formed between amine-bearing moieties of the biomolecule as a result of treatment with a compound of formula (I) can be represented by a structure of formula (Ia)

(Ia)

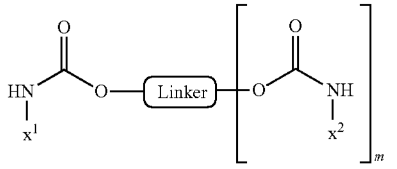

The structure of formula (Ia) depicts the amine-bearing moieties of the biomolecule as $X^1$ and $X^2$, and it is contemplated that $X^1$ and $X^2$ can be moieties on the same or on different biomolecules of the biological sample. The "Linker" can vary as it does in the compound of formula (I), comprising an ethylene glycol moiety, and/or a linear or branched alkane moiety of 2-24 carbons; and m is 1 to 12.

The bis-carbamate crosslinked biomolecules of formula (Ia) represent the "fixed" components of the fixed biological sample. As in other known fixation methods, it is believed that the covalent bis-carbamate crosslinks reduce and/or inhibit the ability of the biomolecule compounds of formula (Ia) to undergo the chemical processes resulting in degradation of the biological sample. Accordingly, the present disclosure also provides fixed biomolecules and compositions of such biomolecules that comprise the covalent bis-carbamate structure of formula (Ia), which is not found in the naturally occurring biomolecules. In at least one embodiment, the present disclosure provides a composition comprising a fixed biological sample, wherein the sample comprises crosslinks of formula (Ia), wherein, $X^1$ and $X^2$ are amine-bearing moieties of the same or different biomolecules of the sample; and "Linker" comprises an ethylene glycol moiety, and/or a linear or branched alkane moiety of 2-24 carbons; and m is 1 to 12.

Further, in at least one embodiment, the present disclosure also provides a composition comprising a fixed biological sample, wherein the sample comprises:

(a) a crosslinked biomolecule of formula (IIa)

(IIa)

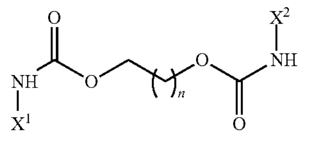

wherein n is 1 to 13;

(b) a crosslinked biomolecule of formula (IIIa)

(IIIa)

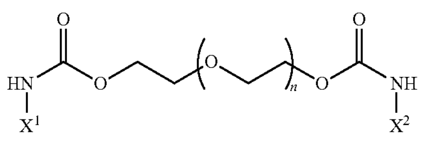

wherein, n is 1 to 12;

(c) a crosslinked biomolecule of formula (IVa)

(IVa)

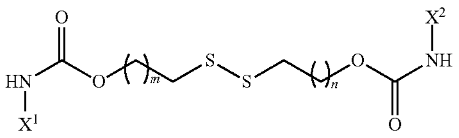

wherein m is 1 to 13, and n is 1 to 13;

(d) a crosslinked biomolecule of formula (Va)

(Va)

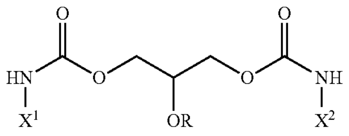

wherein R is selected from —H, —O(CO)—$CH_3$, and —O(CO)-imidazole; and/or (e) a crosslinked biomolecule of formula (VIa)

(VIa)

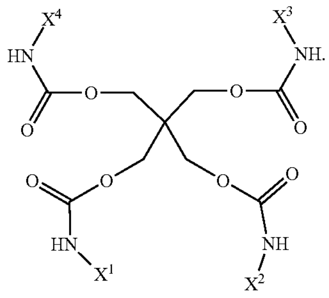

E. Methods for Use of Unfixing Agents

As shown in the above Scheme 2, the fixed biological samples prepared using the fixing reagents of the present disclosure (e.g., compound of formula (I)) comprise bis-carbamate crosslinks. The bis-carbamate crosslinks that act to fix the biomolecules in a biological molecule with a structure of formula (Ia) can be reversed with standard carbamate-cleaving compositions and methods. Thus, a further advantageous technical effect of the fixing reagent compositions and methods of present disclosure is their facile reversibility. The generalized un-fixing reaction that reverses the bis-carbamate crosslinks is shown in Scheme 5, Scheme 5

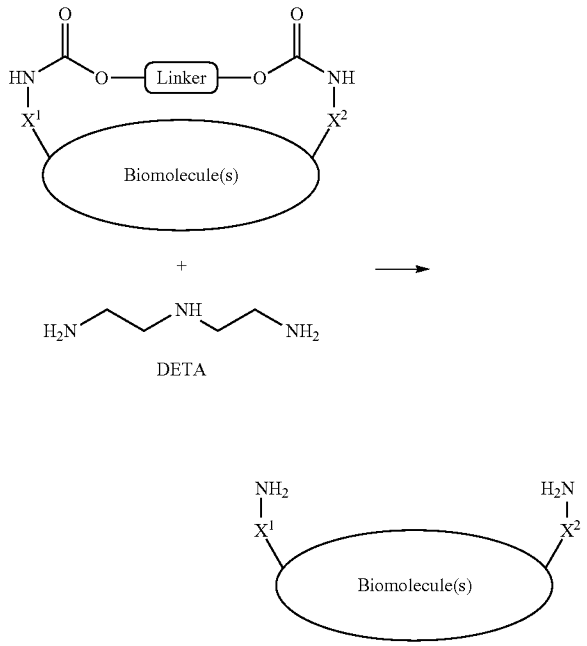

Accordingly, the methods for preparing a biological sample using a bis-imidazole carboxylate fixing reagent compound of formula (I) can further include a subsequent step of reversing the fixation by contacting the sample with unfixing agent. As shown in Scheme 5, the compound diethylenetriamine ("DETA") is effective for the cleavage of carbamate bonds. See e.g., Noshita et al., "Diethylenetriamine-Mediated Direct Cleavage of Unactivated Carbamates and Ureas," Org. Lett. 18: 6062-6065 (2016). Similarly, the diamine compounds, including ethylenediamine ("EDA"), triethylenetetramine ("TETA"), and hydrazine monohydrate can cleave carbamate bonds. The carboxyesterase class of enzymes are capable of cleaving carbamate bonds, and it is contemplated that a carboxyesterase can also be used as an unfixing agent in a method of the present disclosure. Thus, in at least one embodiment, the present disclosure provides a method for preparing a biological sample by contacting the sample with a fixing reagent composition comprising a compound of formula (I), wherein the method further comprises contacting the sample with an unfixing agent, wherein the unfixing agent is a compound capable of cleaving a carbamate bond. In at least one embodiment that includes the unfixing agent, the compound capable of cleaving a carbamate bond is selected from DETA, EDA, TETA, hydrazine monohydrate, a carboxyesterase, or a combination thereof.

As illustrated by the fixing reagent compound of formula (IV), in some embodiments the "Linker" can include a disulfide bond. The addition of a disulfide to the bis-imidazole carboxylate fixing reagent compound allows for the formation of crosslinked biomolecules of formula (IVa). The presence of crosslinked biomolecules of formula (IVa) in a biological sample allows for an alternative two-step un-fixing reaction as illustrated in Scheme 6.

Scheme 6

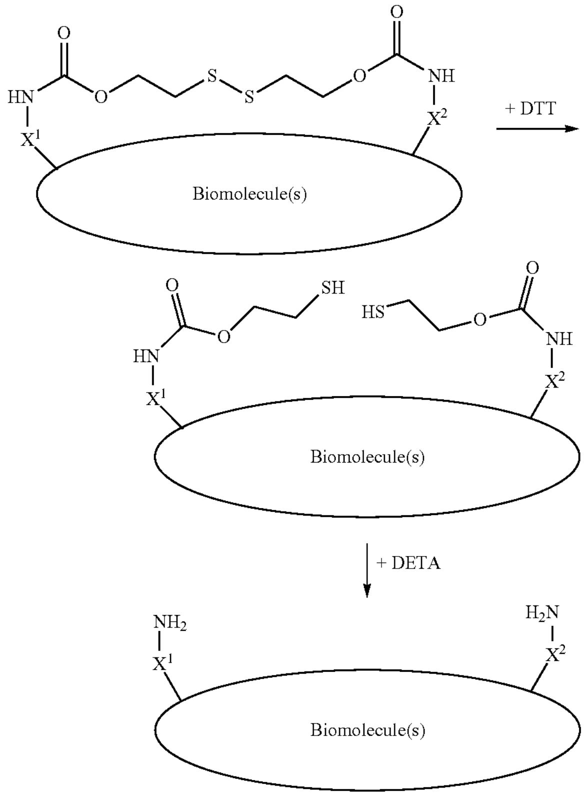

In the first step of the reaction of Scheme 6, the crosslinked biomolecule is treated with the well-known reagent, dithiothreitol ("DTT") that results in the reductive cleavage of the disulfide bonds in the crosslinks. DTT treatment is commonly used and is easily carried out to completion under mild biological conditions. By cleaving the crosslinks, the DTT treatment un-fix the biomolecules to the extent that the crosslinks act to stabilize them from degradation. The resulting un-fixed biomolecules, however, still retain amine-bearing moieties that are modified with sulfhydryl-ethylene-carboxylate moieties. The carbamate-modified amine moieties can potentially interfere with certain subsequent assays of the biomolecules. For example, carbamate-modified nucleobases of nucleic acids will interfere with assays that utilize reverse transcription and amplification of nucleic acid sequences. Accordingly, in at least one embodiment, the present disclosure provides a method wherein a biological sample treated with composition comprising a fixation reagent compound of formula (IV) is contacted with a disulfide cleaving compound, such as DTT, and then contacted with a carbamate-cleaving compound, such as DETA. As shown in Scheme 6, following this two-step treatment, the bis-carbamate crosslinked amine-bearing moieties of the biomolecules are returned to their native state.

F. Fixed Biological Samples in Partitions with Unfixing Agents

Recognized herein is the need for methods, compositions, kits, and systems for analyzing multiple cellular analytes (e.g., genomic, epigenomic, transcriptomic, metabolomic, and/or proteomic information) from fixed biological samples, e.g., individual cells, a population of cells, tissue samples, and other kinds of biological samples. The compositions and methods of the present disclosure are useful to prepare biological samples that are reversibly fixed with a fixing reagent compound of formula (I), then provided (or encapsulated) in discrete partitions along with an unfixing agent capable of reversing the fixed state of the biomolecules while sequestered in the partition. Accordingly, in some embodiments, the present disclosure provides a method for preparing a biological sample comprising: generating a discrete partition comprising (or encapsulating) a biological sample that has been fixed using a bis-imidazole carboxylate compound of formula (I), and an unfixing agent that is capable of reversing the bis-carbamate crosslinked molecules of formula (Ia). This method can further comprise an initial step of fixing the biological sample prior to generating the discrete partition.

The present disclosure provides methods, composition, kits, and systems for treating fixed biological samples in order to process cellular analytes. Cellular analytes that are suitable for use with the compositions and methods of the present disclosure include, without limitation, intracellular and partially intracellular analytes. The cellular analyte may be a protein, a metabolite, a metabolic byproduct, an antibody or antibody fragment, an enzyme, an antigen, a carbohydrate, a lipid, a macromolecule, or a combination thereof (e.g., proteoglycan) or other biomolecule. The cellular analyte may be a nucleic acid molecule. The cellular analyte may be a deoxyribonucleic acid (DNA) molecule or a ribonucleic acid (RNA) molecule. The DNA molecule may be a genomic DNA molecule. The cellular analyte may comprise coding or non-coding RNA. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA.

In some instances, the cellular analyte is associated with an intermediary entity, wherein the intermediary entity is analyzed to provide information about the cellular analyte and/or the intermediary entity itself. For instance, an intermediary entity (e.g., an antibody) may be bound to a partially intracellular analyte (e.g., a cell surface receptor), where the intermediary entity is processed to provide information about the intermediary entity, the partially intracellular analyte, or both. In one embodiment, the intermediary entity comprises an identifier (e.g., a barcode molecule) that can be used to generate barcode molecules (e.g., droplet-based barcoding) as further described herein.

The term "partition," as used herein, generally, refers to a space or volume that may be suitable to contain one or more species or conduct one or more reactions. A partition may be a physical compartment, such as a droplet or well (e.g., a microwell). The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments Methods, techniques, and protocols useful for partitioning biological samples (e.g., individual cells, biomolecular contents of cells, etc.) into discrete partitions (e.g., wells or droplets) are described in the art. In one embodiment, the discrete partitions generated act a nanoliter-scale container that can maintain separation of the partition contents from the contents of other partitions (e.g., droplets in the emulsion).

Methods and systems for creating stable discrete droplets comprising or encapsulating individual particles from biological samples in non-aqueous or oil emulsions are described in, e.g., U.S. Patent Application Publication Nos. 2010/0105112 and 2019/0100632, each of which is entirely incorporated herein by reference for all purposes. Briefly, discrete droplets in an emulsion comprising or encapsulating a biological sample is accomplished by introducing a flowing stream of an aqueous fluid containing the biological sample into a flowing stream of a non-aqueous fluid with which it is immiscible, such that droplets are generated at the junction of the two streams (see FIGS. 1-3). By providing the aqueous stream at a certain concentration and/or flow rate of the biological sample, the occupancy of the resulting droplets can be controlled. For example, the relative flow rates of the immiscible fluids can be selected such that, on average, the discrete droplet each contains less than one biological particle. Such a flow rate ensures that the droplets that are occupied are primarily occupied by a single sample (e.g., a single cell). Discrete droplets in an emulsion comprising or encapsulating a biological sample is also accomplished using a microfluidic architecture comprising a channel segment having a channel junction with a reservoir (see FIGS. 4-6).

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle.

In some cases, the droplets among a plurality of discrete droplets formed in the manner contain at most one particle (e.g., one support such as a bead) and one biological particle (e.g., one cell including one fixed cell or one un-fixed cell). The flows and microfluidic channel architectures also can be controlled to ensure a given number of singly occupied droplets, less than a certain level of unoccupied droplets, and/or less than a certain level of multiply occupied droplets.

In another aspect of the disclosure, fixed cells (e.g., cells fixed according to the fixing reagent compositions described herein) may then be partitioned (e.g., in a droplet or well)

with other reagents for processing of one or more analytes as described herein. In one embodiment, the fixed cell may be co-partitioned with an unfixing agent. In one other embodiment, the partition comprising the fixed cell further comprises a support (e.g., a bead) comprising nucleic acid molecules suitable for barcoding of the one or more analytes. In another embodiment, the nucleic acid molecules may include nucleic acid sequences that provide identifying information, e.g., barcode sequence(s).

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence (e.g., targeted by a primer sequence) or a non-targeted sequence. For example, in the methods, compositions, kits, and systems described herein, hybridization and reverse transcription of the nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

FIG. 1 shows an exemplary microfluidic channel structure 100 useful for generating discrete droplets comprising or encapsulating a particle from a biological sample, such as a single cell. The channel structure 100 can include channel segments 102, 104, 106 and 108 communicating at a channel junction 110. In operation, a first aqueous fluid 112 that that includes suspended particles (e.g., cells) from a biological sample 114 are transported along channel segment 102 into junction 110, while a second fluid 116 (or "partitioning fluid") that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual particle from a biological sample 114 (such as droplet 118), or discrete droplet can be generated that includes more than one particle 114 (not shown in FIG. 1). A discrete droplet may contain no biological particle 114 (such as droplet 120). Each discrete droplet is capable of maintaining separation of its own contents (e.g., individual biological sample particle 114) from the contents of other droplets.

Typically, the second fluid 116 comprises an oil, such as a fluorinated oil, that includes a fluoro-surfactant that helps to stabilize the resulting droplets. Examples of useful partitioning fluids and fluoro-surfactants are described in e.g., U.S. Patent Application Publication No. 2010/0105112, which is entirely incorporated herein by reference for all purposes.

The microfluidic channels for generating discrete droplets as exemplified in FIG. 1 may be coupled to any of a variety of different fluid sources or receiving components, including reservoirs, tubing, manifolds, or fluidic components of other systems. Additionally, the microfluidic channel structure 100 may have other geometries, including geometries having more than one channel junction. For example, the microfluidic channel structure can have 2, 3, 4, or 5 channel segments each carrying biological sample particles, assay reagents, and/or beads that meet at a channel junction.

Generally, the fluids used in generating the discrete droplets are directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

One of ordinary skill will recognize that numerous different microfluidic channel designs are available that can be used with the methods and compositions of the present disclosure to provide discrete droplets containing a particle of a biological sample fixed with a compound of formula (I), an unfixing agent capable of cleaving bis-carbamate cross-links (e.g., DETA), and/or a bead with a barcode and/or other assay reagents.

The inclusion of a barcode in a discrete partition (e.g., a well or a droplet) along with the biological sample provides a unique identifier that allows data from the biological sample to be distinguished and individually analyzed. Barcodes can be delivered previous to, subsequent to, or concurrent with the biological sample in discrete partition. For example, barcodes may be injected into droplets previous to, subsequent to, or concurrently with droplet generation. Barcodes useful in the methods and compositions of the present disclosure typically comprise a nucleic acid molecule (e.g., an oligonucleotide). The nucleic acid barcode molecules typically are delivered to a partition via a support, such as bead. In some cases, barcode nucleic acid molecules are initially associated with the bead upon providing the discrete partition (e.g., providing a discrete well or upon generation of the discrete droplet), and then released from the bead upon application of a stimulus to the partition (e.g., the well or the droplet). Barcode carrying beads useful in the methods and compositions of the present disclosure are described in further detail elsewhere herein.

Methods and systems for partitioning barcode carrying beads into droplets are provided in U.S. Pat. No. 10,480,029, 10,858,702, and 10,725,027, US. Patent Publication Nos. 2019/0367997 and 2019/0064173, and International Application Nos. PCT/US20/17785 and PCT/US20/020486, each of which is herein entirely incorporated by reference for all purposes.

Figure 8:
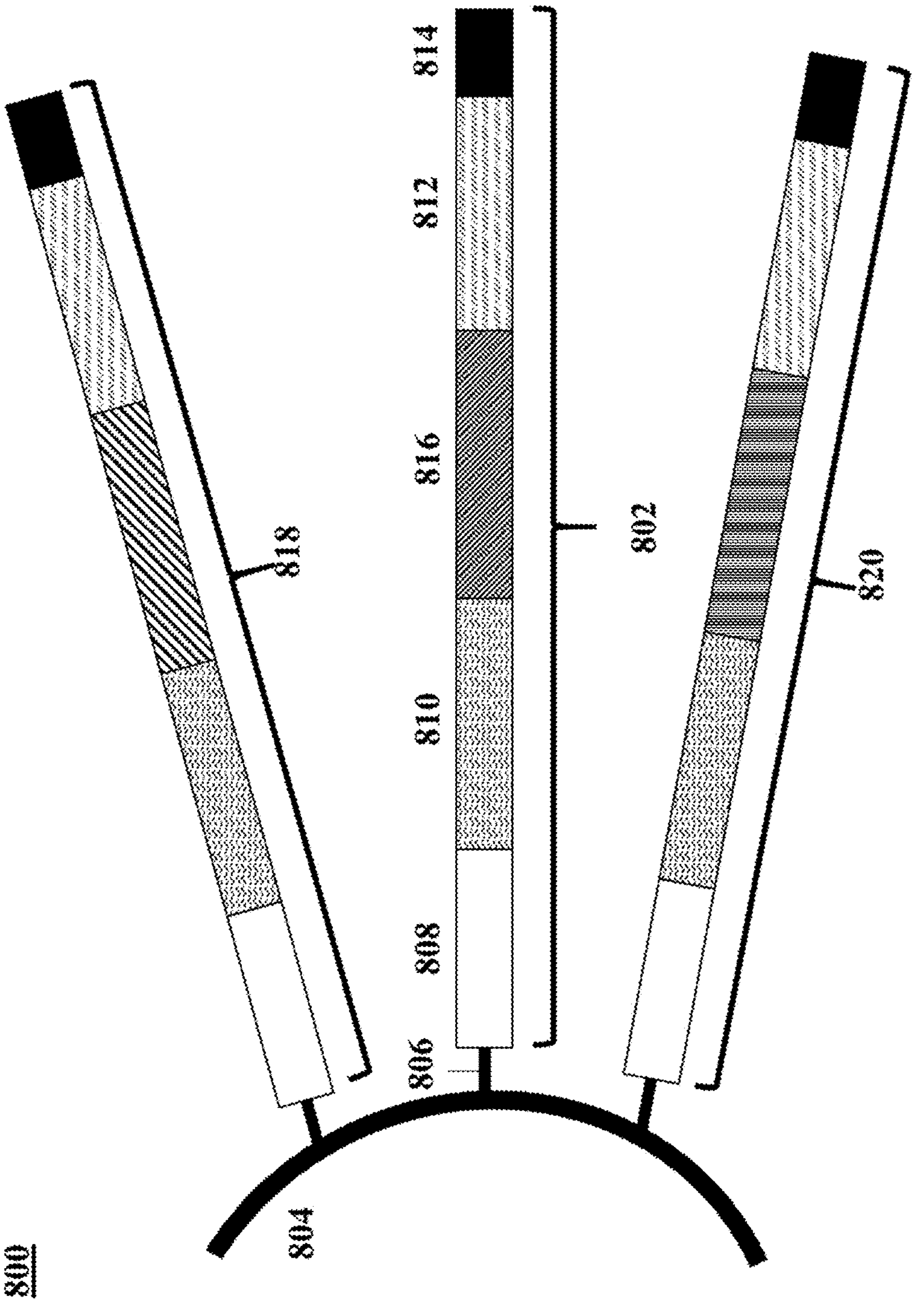
FIG. 8 shows an exemplary barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumine® sequencing systems) and a sequencing primer sequence (e.g., a R1 primer for Illumine® sequencing systems). The nucleic acid molecule 802 may comprise a barcode sequence 810 for use in barcoding the sample (e.g., DNA, RNA, protein, antibody, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

A biological particle (e.g., cell, fixed cell, un-fixed cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810.

However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., a cell, a fixed cell, an un-fixed cell, etc.). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing). The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where the nucleic acid molecules from the sample remain attached to the bead, the beads from various partitions may be collected, pooled, and subjected to further processing (e.g., reverse transcription, adapter attachment, amplification, clean up, sequencing). In other instances, the processing may occur in the partition. For example, conditions sufficient for barcoding, adapter attachment, reverse transcription, or other nucleic acid processing operations may be provided in the partition and performed prior to clean up and sequencing.

Figure 9:
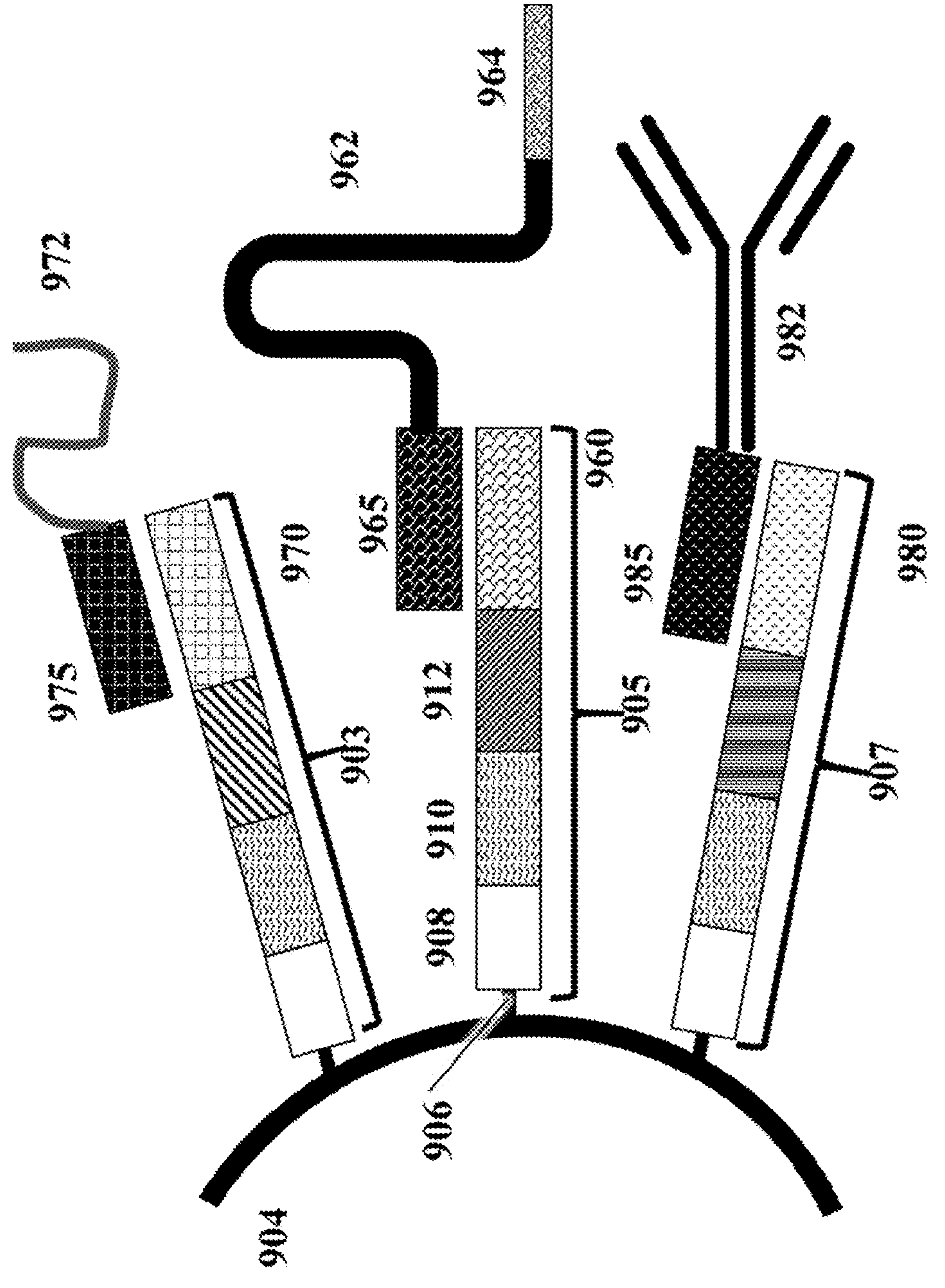
FIG. 9 shows another exemplary barcode carrying bead.

FIG. 9 illustrates another example of a barcode carrying bead. A nucleic acid molecule 905, such as an oligonucleotide, can be coupled to a bead 904 by a releasable linkage 906, such as, for example, a disulfide linker. The nucleic acid molecule 905 may comprise a first capture sequence 960. The same bead 904 may be coupled (e.g., via releasable linkage) to one or more other nucleic acid molecules 903, 907 comprising other capture sequences. The nucleic acid molecule 905 may be or comprise a barcode. As noted elsewhere herein, the structure of the barcode may comprise a number of sequence elements, such as a functional sequence 908 (e.g., flow cell attachment sequence, sequencing primer sequence, etc.), a barcode sequence 910 (e.g., bead-specific sequence common to bead, partition-specific sequence common to partition, etc.), and a unique molecular identifier 912 (e.g., unique sequence within different molecules attached to the bead), or partial sequences thereof. The capture sequence 960 may be configured to attach to a corresponding capture sequence 965. In some instances, the corresponding capture sequence 965 may be coupled to another molecule that may be an analyte or an intermediary carrier. For example, as illustrated in FIG. 9, the corresponding capture sequence 965 is coupled to a guide RNA molecule 962 comprising a target sequence 964, wherein the target sequence 964 is configured to attach to the analyte. Another oligonucleotide molecule 907 attached to the bead 904 comprises a second capture sequence 980 which is configured to attach to a second corresponding capture sequence 985. As illustrated in FIG. 9, the second corresponding capture sequence 985 is coupled to an antibody 982. In some cases, the antibody 982 may have binding specificity to an analyte (e.g., surface protein). Alternatively, the antibody 982 may not have binding specificity. Another oligonucleotide molecule 903 attached to the bead 904 comprises a third capture sequence 970 which is configured to attach to a second corresponding capture sequence 975. As illustrated in FIG. 9, the third corresponding capture sequence 975 is coupled to a molecule 972. The molecule 972 may or may not be configured to target an analyte. The other oligonucleotide molecules 903, 907 may comprise the other sequences (e.g., functional sequence, barcode sequence, UMI, etc.) described with respect to oligonucleotide molecule 905. While a single oligonucleotide molecule comprising each capture sequence is illustrated in FIG. 9, it will be appreciated that, for each capture sequence, the bead may comprise a set of one or more oligonucleotide molecules each comprising the capture sequence. For example, the bead may comprise any number of sets of one or more different capture sequences. Alternatively, or in addition, the bead 904 may comprise other capture sequences. Alternatively, or in addition, the bead 904 may comprise fewer types of capture sequences (e.g., two capture sequences). Alternatively or in addition, the bead 904 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

Figure 2:
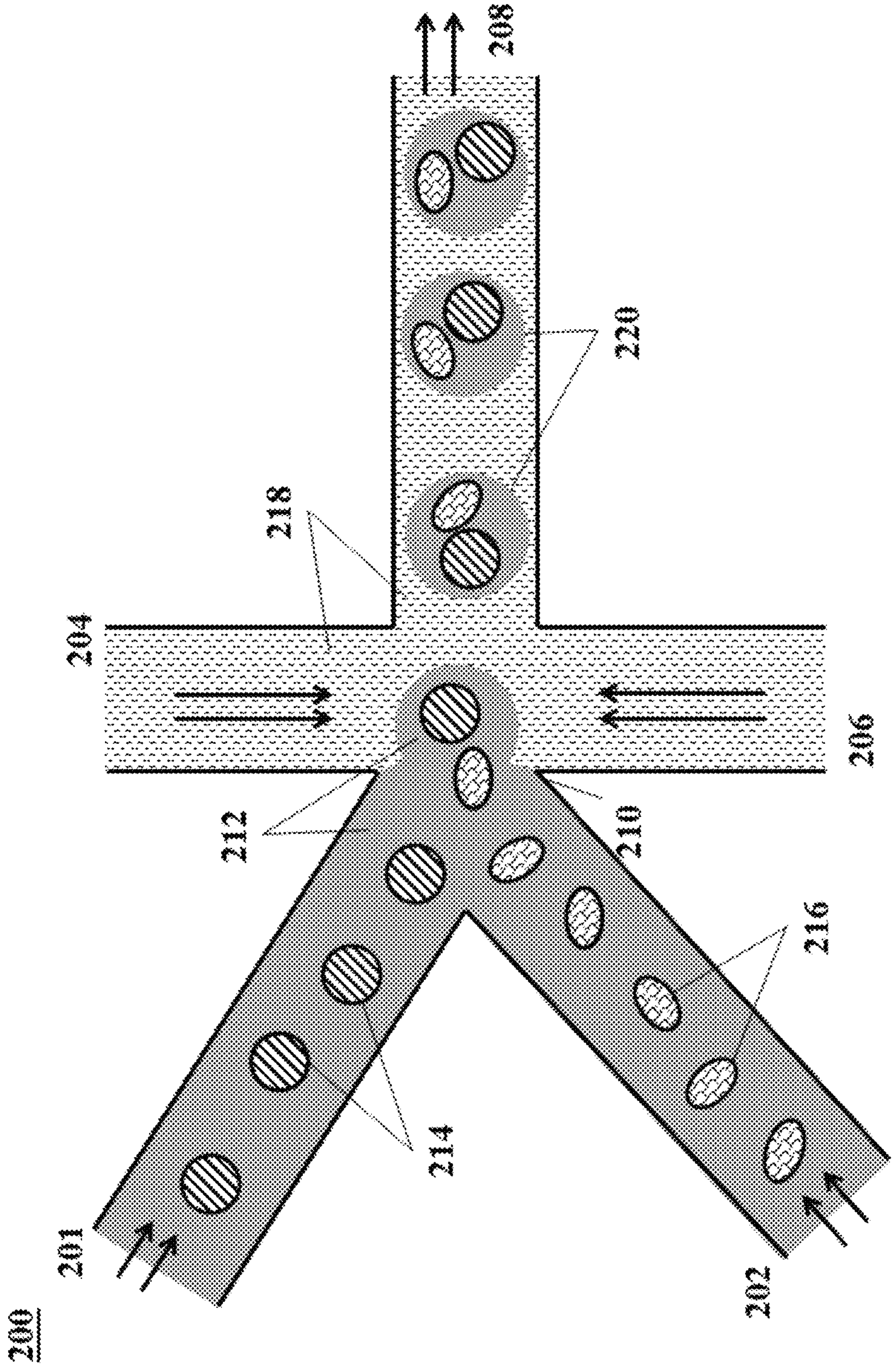
FIG. 2 shows an example of a microfluidic channel structure for delivering barcode carrying beads to droplets.

FIG. 2 shows an exemplary microfluidic channel structure 200 for generating discrete droplets comprising or encapsulating a barcode carrying bead 214 along with a biological sample particle 216. The channel structure 200 includes channel segments 201, 202, 204, 206 and 208 in fluid communication at a channel junction 210. In operation, the channel segment 201 transports an aqueous fluid 212 that can include a plurality of beads 214 (e.g., beads carrying barcode oligonucleotides) along the channel segment 201 into junction 210. The plurality of beads 214 may be sourced from a suspension of beads. For example, the channel segment 201 can be connected to a reservoir comprising an aqueous suspension of beads 214. The channel segment 202 transports the aqueous fluid 212 that includes a plurality of biological sample particles 216 along the channel segment 202 into junction 210. The plurality of biological sample particles 216 may be sourced from a suspension of biological sample particles. For example, the channel segment 202 may be connected to a reservoir comprising an aqueous suspension of biological sample particles 216. In some instances, the aqueous fluid 212 in either the first channel segment 201 or the second channel segment 202, or in both segments, can include one or more reagents, as further described elsewhere herein. For example, in some embodiments of the present disclosure, where the biological sample particles are fixed with a compound of formula (I), the aqueous fluid in the first and/or second channel segments that delivers the biological sample and beads, respectively, can include an unfixing agent capable of cleaving bis-carbamate crosslinks (e.g., DETA). The second fluid 218 that is immiscible with the aqueous fluid 212 is delivered to the junction 210 from each of channel segments 204 and 206. Upon meeting of the aqueous fluid 212 from each of channel segments 201 and 202 and the second fluid 218 (e.g., a fluorinated oil) from each of channel segments 204 and 206 at the channel junction 210, the aqueous fluid 212 is partitioned into discrete droplets 220 in the second fluid 218 and flow away from the junction 210 along channel segment 208. The channel segment 208 can then deliver the discrete droplets comprising or encapsulating the biological sample particle and barcode carrying bead to an outlet reservoir fluidly coupled to the channel segment 208, where they can be collected.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Using such a channel system as exemplified in FIG. 2, discrete droplets 220 can be generated that comprise or encapsulate an individual biological particle of a biological sample, and one bead, wherein the bead can carry a barcode and/or another reagent. It is also contemplated, that in some instances, a discrete droplet may be generated using the channel system of FIG. 2, wherein droplet includes more than one individual biological sample particle or includes no biological sample. Similarly, in some embodiments, the discrete droplet may include more than one bead or no bead. A discrete droplet also may be completely unoccupied (e.g., no bead or biological sample).

In some embodiments, it is desired that the beads, biological sample particles, and generated discrete droplets flow along channels at substantially regular flow rates that generate a discrete droplet containing a single bead and a single biological sample particle. Regular flow rates and devices that may be used to provide such regular flow rates are known in the art, see e.g., U.S. Patent Publication No. 2015/0292988, which is hereby incorporated by reference herein in its entirety. In some embodiments, the flow rates are set to provide discrete droplets containing a single bead and a biological sample particle with a yield rate of greater than 5%, 10%, 20%, 30%, 40%, 50%, 60%, 70%, 80%, 90%, or 95%.

G. Uses of Supports Provided in Partitions

Supports that can carry barcodes and/or other reagents that are useful with the compositions and methods of the present disclosure and can include, without limitation, beads that are porous, non-porous, solid, semi-solid, semi-fluidic, fluidic, and/or a combination thereof. In some embodiments, the bead can be made of a material that is dissolvable, disruptable, and/or degradable, such as a gel bead comprising a hydrogel. Alternatively, in some embodiments, the bead is not degradable.

In some embodiments of the present disclosure, the bead is provided in a discrete partition (e.g., the bead is provided or encapsulated in a discrete droplet or provided in a discrete well) with a biological sample is a bead. Typically, the bead useful in the embodiments disclosed herein comprise a hydrogel. Such gel beads can be formed from molecular precursors, such as a polymeric or monomeric species, that undergo a reaction to form crosslinked gel polymer. Another semi-solid bead useful in the present disclosure is a liposomal bead. In some embodiments, beads used can be solid beads that comprise a metal including iron oxide, gold, and silver. In some cases, the bead may be a silica bead. In some cases, the bead can be rigid. In other cases, the bead may be flexible and/or compressible. Generally, the beads can be of any suitable shape. Examples of bead shapes include, but are not limited to, spherical, non-spherical, oval, oblong, amorphous, circular, cylindrical, and variations thereof.

The plurality beads used in the embodiments can be of uniform size or they can comprise a collection of heterogeneous sizes. In some cases, the diameter of a bead is at least about 1 micron (μm), 5 μm, 10 μm, 20 μm, 30 μm, 40 μm, 50 μm, 60 μm, 70 μm, 80 μm, 90 μm, 100 μm, 250 μm, 500 μm, 1000 μm (1 mm), or greater. In some cases, a bead may have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In some embodiments, the beads used are a population or plurality of beads having a relatively monodisperse size distribution. Typically, where it is desirable to provide a consistent amount of reagent within a discrete partition (e.g., a well or a droplet), the use of relatively consistent bead characteristics, such as size, provides overall consistency in the content of each partition. For example, the beads useful in the embodiments of the present disclosure can have size distributions that have a coefficient of variation in their cross-sectional dimensions of less than 50%, less than 40%, less than 30%, less than 20%, and in some cases less than 15%, less than 10%, less than 5%, or less.

The beads useful in the methods and compositions of the present disclosure can comprise a range of natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly (tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

Although FIG. 1 and FIG. 2 have been described in terms of providing substantially singly occupied discrete droplets, it is also contemplated in certain embodiments that it is desirable to provide multiply occupied discrete droplets, e.g., a single droplet that contains two, three, four or more cells from a biological sample, and/or multiple different beads, such as a bead carrying a barcode nucleic acid molecule and/or a bead carrying a reagent such as a lysis agent, an unfixing agent and/or assay reagent. Accordingly, as noted elsewhere herein, the flow characteristics of the biological particle and/or the beads can be controlled to provide for such multiply occupied droplets. In particular, the flow parameters of the liquids used in the channel structures may be controlled to provide a given droplet occupancy rate greater than about 50%, greater than about 75%, and in some cases greater than about 80%, 90%, 95%, or higher.

In some embodiments, the beads useful in the compositions and methods of the present disclosure are beads capable of delivering reagents (e.g., an unfixing agent, and/or an assay reagent) into the discrete partition (e.g., a droplet) containing the biological sample particle that has been fixed by treatment with a compound of formula (I). In some embodiments, the different beads (e.g., containing different reagents) can be introduced from different sources into different inlets leading to a common droplet generation junction (e.g., junction 210). In such cases, the flow and frequency of the different beads into the channel or junction may be controlled to provide for a certain ratio of beads from each source, while ensuring a given pairing or combination of such beads into a partition with a given number of biological particles (e.g., one biological particle and one bead per partition).

The discrete droplets described herein generally comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. In some embodiments, the discrete droplets generated that comprise or encapsulate a biological particle from a sample have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. It will be appreciated that the sample fluid volume, e.g., including co-partitioned biological particles and/or beads, within the droplets may be less than about 90% of the above described volumes, less than about 80%, less than about 70%, less than about 60%, less than about 50%, less than about 40%, less than about 30%, less than about 20%, or less than about 10% of the above described volumes.

The methods of generating discrete droplets useful with the compositions and methods of the present disclosure, result in the generation of a population or plurality of discrete droplets containing a biological sample particle (e.g., a biological sample fixed treatment with a compound of formula (I)) and other reagents (e.g., an unfixing agent, such as DETA). Generally, the methods are easily controlled to provide for any suitable number of droplets. For example, at least about 1,000 discrete droplets, at least about 5,000 discrete droplets, at least about 10,000 discrete droplets, at least about 50,000 discrete droplets, at least about 100,000 discrete droplets, at least about 500,000 discrete droplets, at least about 1,000,000 discrete droplets, at least about 5,000, 000 discrete droplets, at least about 10,000,000 discrete droplets, or more discrete droplets can be generated or otherwise provided. Moreover, the plurality of discrete droplets may comprise both unoccupied and occupied droplets.

As described elsewhere herein, in some embodiments of the compositions and methods of the present disclosure, the generated discrete droplets comprising or encapsulating a biological sample particle, and optionally, one or more different beads, also contain other reagents. In some embodiments, the other reagents contained in or encapsulated in the droplet include lysis and/or unfixing agents that act to release and/or un-fix the biomolecule contents of the biological sample particle within the droplet. In some embodiments, the lysis and/or unfixing agents can be contacted with the biological sample suspension concurrently with, or immediately prior to, the introduction of the biological sample particles into the droplet generation junction of the microfluidic system (e.g., junction 210). In some embodiments, the agents are introduced through an additional channel or channels upstream of the channel junction.

Figure 3:
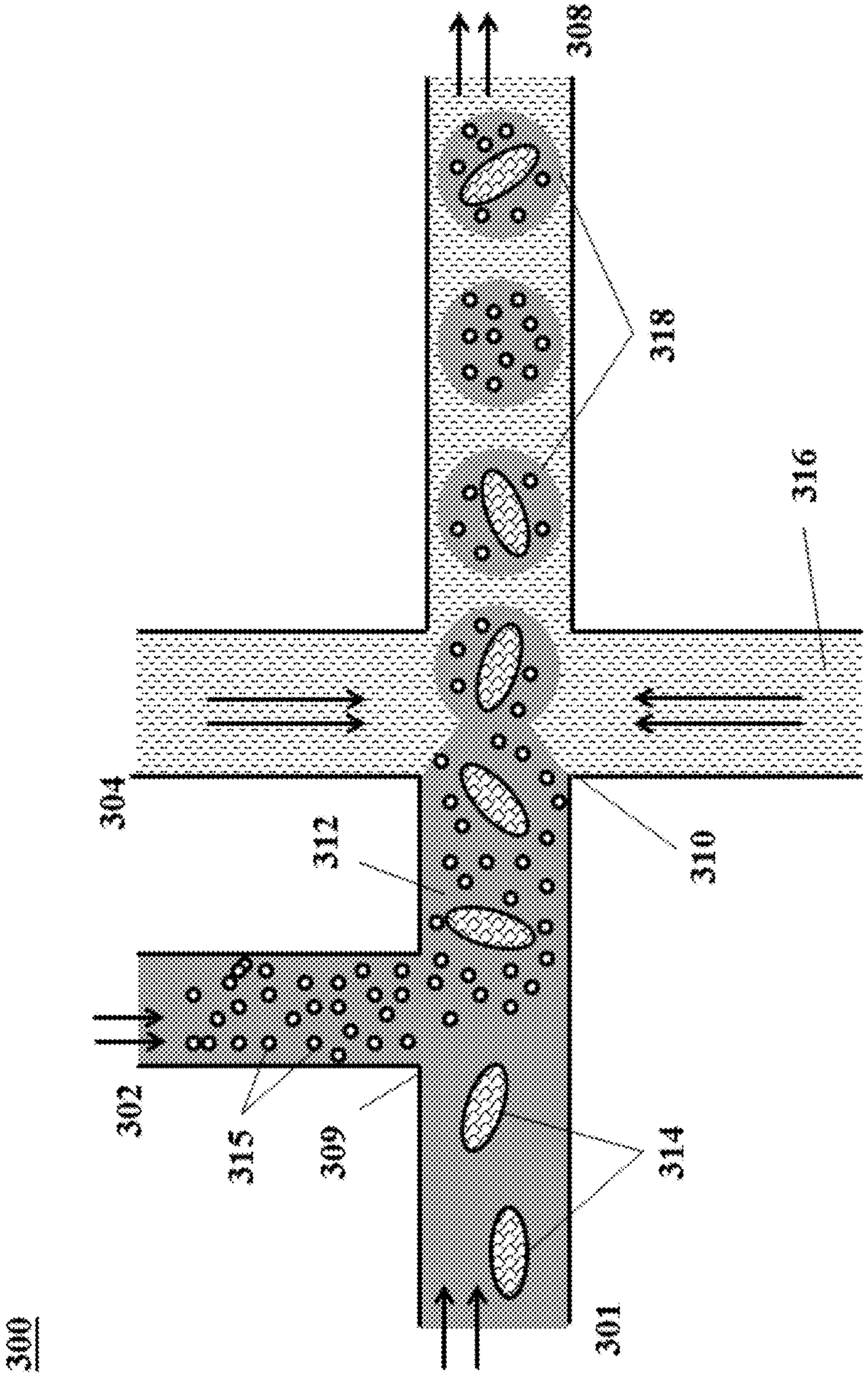
FIG. 3 shows an example of a microfluidic channel structure for co-partitioning biological particles and reagents.

In some embodiments, a biological sample particle can be co-partitioned along with the other reagents. FIG. 3 shows an example of a microfluidic channel structure 300 for co-partitioning biological sample particles and other reagents, including lysis and/or unfixing agents. The channel structure 300 can include channel segments 301, 302, 304, 306 and 308. Channel segments 301 and 302 communicate at a first channel junction 309. Channel segments 302, 304, 306, and 308 communicate at a second channel junction 310. In exemplary co-partitioning operation, the channel segment 301 may transport an aqueous fluid 312 that includes a plurality of biological sample particles 314 (e.g., a fixed biological sample) along the channel segment 301 into the second junction 310. As an alternative or in addition to, channel segment 301 may transport beads (e.g., gel beads that carry barcodes). For example, the channel segment 301 may be connected to a reservoir comprising an aqueous suspension of biological sample particles 314. Upstream of, and immediately prior to reaching, the second junction 310, the channel segment 301 may meet the channel segment 302 at the first junction 309. The channel segment 302 can transport a plurality of reagents 315 (e.g., lysis or unfixing agents) in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological sample particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., a fluorinated oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 is partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be collected for further analysis.

Discrete droplets generated can include an individual biological sample particle 314 and/or one or more reagents 315, depending on what reagents are included in channel segment 302. In some instances, a discrete droplet generated may also include a barcode carrying bead (not shown), such as can be added via other channel structures described elsewhere herein. In some instances, a discrete droplet may be unoccupied (e.g., no reagents, no biological particles). Generally, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological sample particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Figure 4:
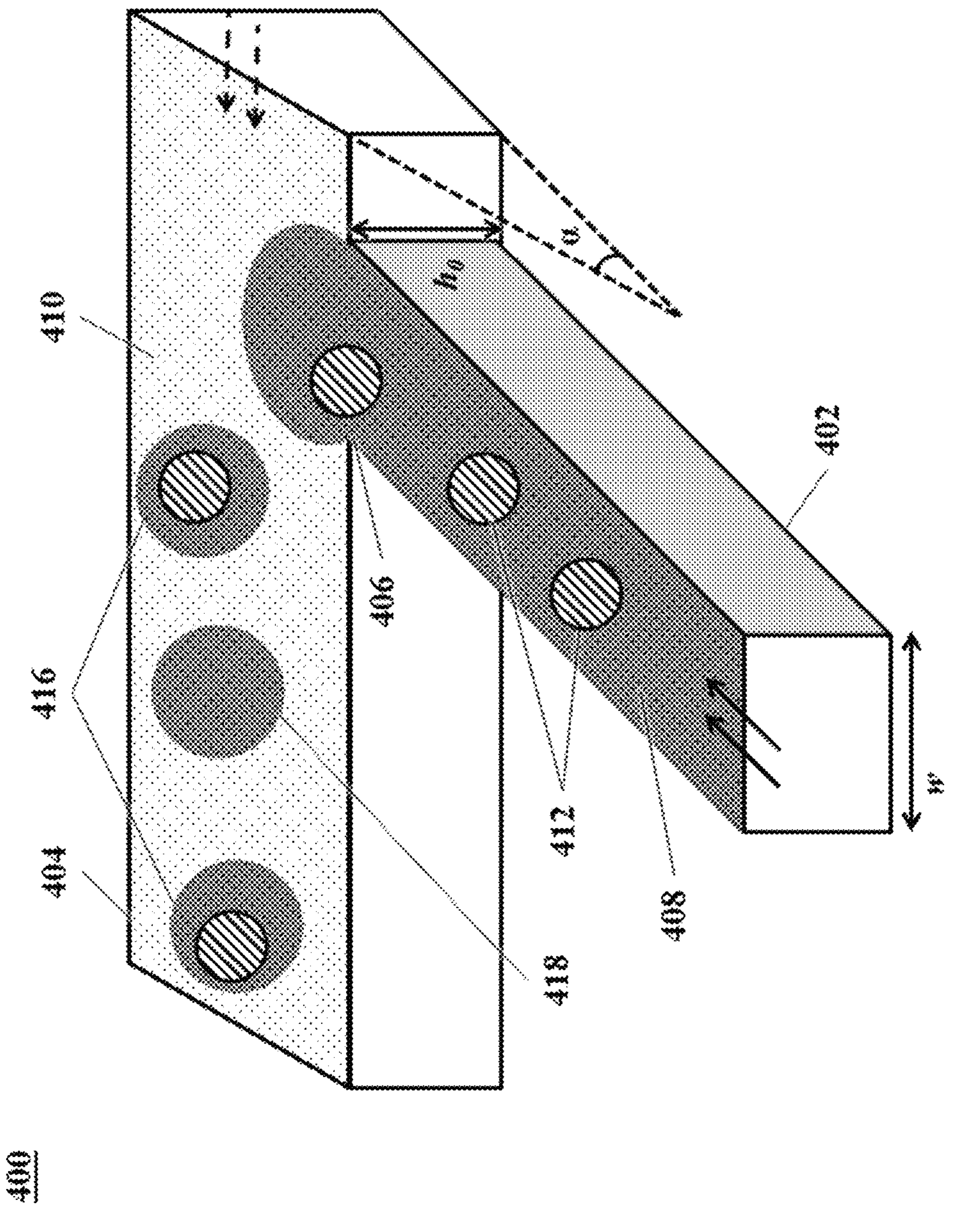
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, ho, a, etc.) of the channel structure 400. A plurality of droplets can be collected in the reservoir 404 by continuously injecting the aqueous fluid 408 from the channel segment 402 through the junction 406.

Figure 5:
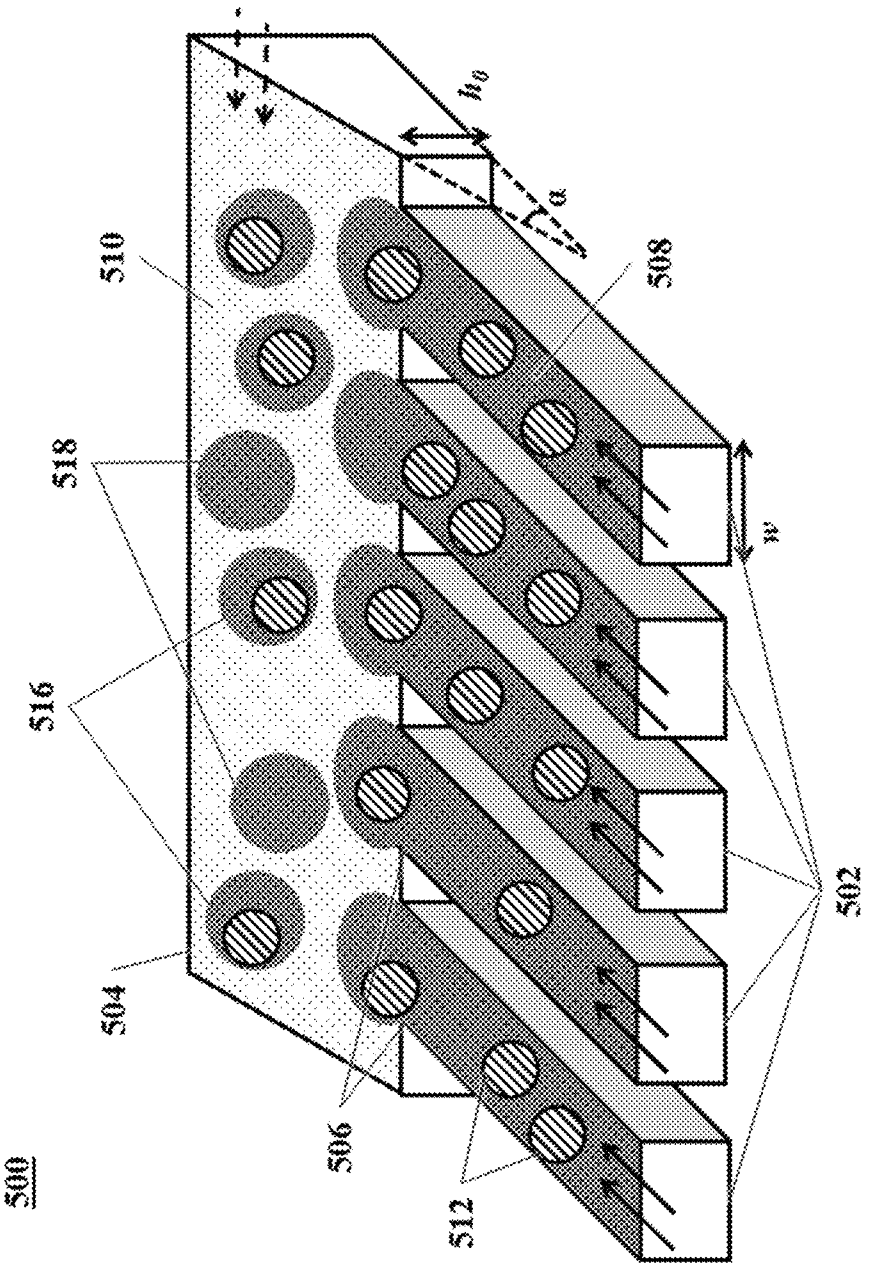
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Figure 6:
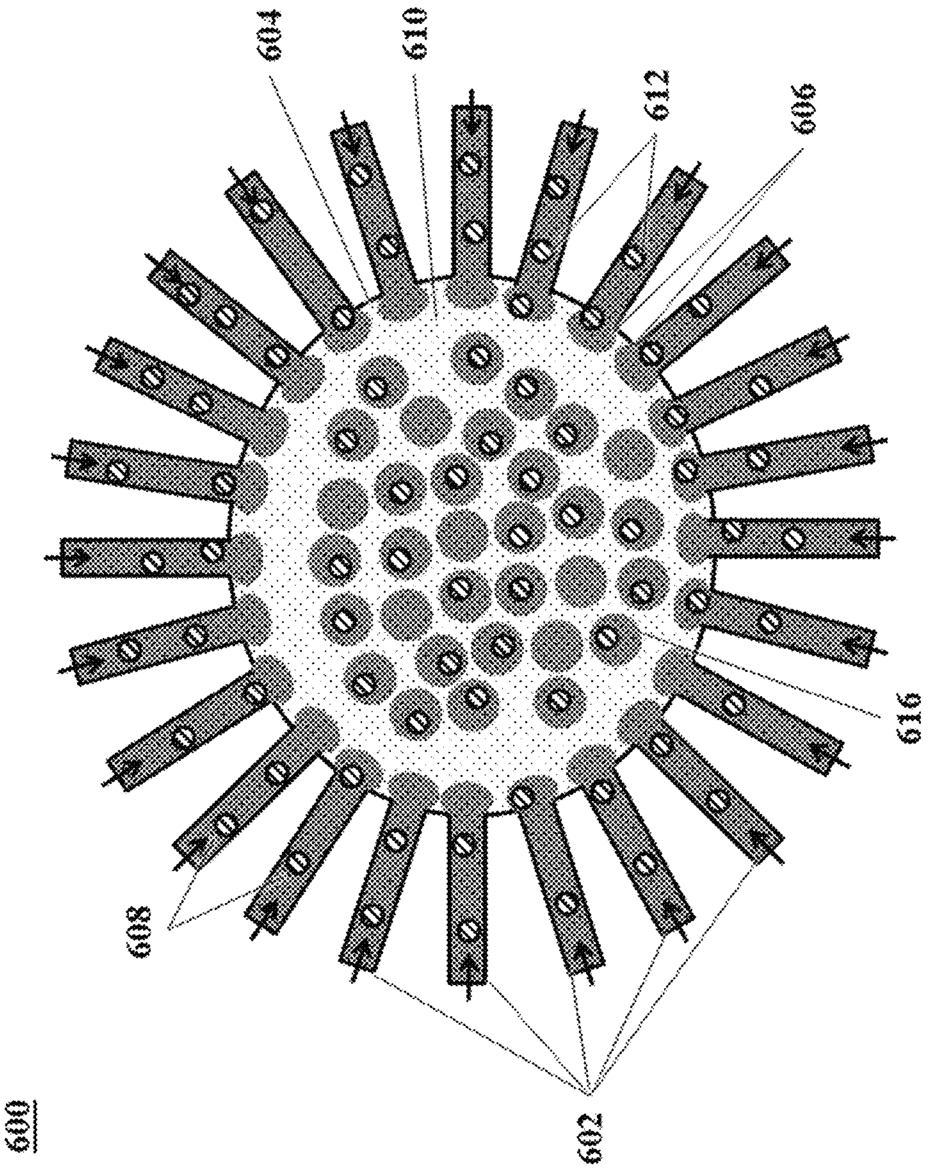
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 4 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof. Additional aspects of such microfluidic structures, including systems and methods implementing the same, are provided in US Published Patent Application No 20190323088, which is incorporated herein by reference in its entirety.

Once the lysis and/or unfixing agents are co-partitioned in a partition (e.g., a well or a droplet) with a particle of a biological sample fixed with a compound of formula (I), these reagents can facilitate the release and un-fixing of the biomolecular contents of the biological sample particle within the partition. As described elsewhere herein, the un-fixed biomolecular contents released in a partition remain discrete from the contents of other partitions, thereby allowing for detection and quantitation of the biomolecular analytes of interest present in that distinct biological sample.

Examples of lysis agents useful in the compositions and methods of the present disclosure include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological samples' contents into the partition (e.g., the well or the droplet). For example, in some cases, surfactant-based lysis solutions may be used to lyse cells, although these may be less desirable for emulsion based systems where the surfactants can interfere with stable emulsions. In some embodiment, the lysis solutions can include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as the provision or encapsulation of biological particles that may be in addition to or in place of droplet partitioning, where any pore size of the encapsulating material is sufficiently small to retain nucleic acid fragments of a given size, following cellular disruption.

In addition to the lysis and/or unfixing agents co-partitioned into discrete partitions (e.g., wells or droplets) with the biological sample particles, it is further contemplated that other assay reagents can also be co-partitioned in the partition. For example, DNase and Rnase inactivating agents or inhibitors, such as proteinase K, chelating agents, such as EDTA, and other reagents employed in removing or otherwise reducing negative activity or impact of different cell lysate components on subsequent processing of nucleic acids.

In some embodiments, the biological sample particles provided in or encapsulated in discrete partitions (e.g., wells or droplets) with other reagents are exposed to an appropriate stimulus to release the biomolecular contents of the sample particles and/or the contents of a co-partitioned bead. For example, in some embodiments, a chemical stimulus may be co-partitioned in the partition along with a biological sample particle and a bead (e.g., a gel bead) to allow for the degradation of the bead and release of its contents into the partition. In some embodiments, a discrete partition can be provided (e.g., a droplet can be generated) along with a particle of a biological sample fixed with a compound of formula (I) and an unfixing agent capable of cleaving bis-carbamate crosslinks (e.g., DETA), wherein the unfixing agent is contained in a bead (e.g., a gel bead) that can be degraded by heat stimulus. In such an embodiment, the partition is exposed to heat stimulus thereby degrading the bead and releasing the unfixing agent. In another embodiment, it is contemplated that a partition containing (e.g., a droplet providing or encapsulating) a particle of a biological sample fixed with a compound of formula (I), and two different beads (e.g., one bead carrying an unfixing agent, and one bead carrying assay reagents), wherein the contents of the two different beads are released by non-overlapping stimuli (e.g., a chemical stimulus and a heat stimulus). Such an embodiment can allow the release of the different reagents into the same discrete partition at different times. For example, a first bead, triggered by heat stimulus, releases an unfixing agent into the partition, and then after a set time, a second bead, triggered by a chemical stimulus, releases assay reagents that detect analytes of the biological sample particle that has been un-fixed by contact the unfixing agent.

Additional assay reagents may also be co-partitioned into discrete partitions (e.g., wells or droplets) with the biological samples, such as endonucleases to fragment a biological sample's DNA, DNA polymerase enzymes and dNTPs used to amplify the biological sample's nucleic acid fragments and to attach the barcode molecular tags to the amplified fragments. Other enzymes may be co-partitioned, including without limitation, polymerase, transposase, ligase, proteinase K, Dnase, etc. Additional assay reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching.

In some embodiments, template switching can be used to increase the length of cDNA generated in an assay. In some embodiments, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner.

Once the contents of a biological sample cell are released into a discrete partition (e.g., a well or a droplet), the biomolecular components (e.g., macromolecular constituents of biological samples, such as RNA, DNA, or proteins) contained therein may be further processed within the partition. In accordance with the methods and systems described herein, the biomolecular contents of individual biological samples can be provided with unique barcode identifiers, and upon characterization of the biomolecular components (e.g., in a sequencing assay) they may be attributed as having been derived from the same biological sample. The ability to attribute characteristics to individual biological samples or groups of biological samples is provided by the assignment of a nucleic acid barcode sequence specifically to an individual biological sample or groups of biological samples.

In some embodiments, the unique identifier barcodes are provided in the form of nucleic acid molecules (e.g., oligonucleotides) that comprise sequences that may be attached to or otherwise associated with the nucleic acid contents of individual biological sample, or to other components of the biological sample, and particularly to fragments of those nucleic acids. In some embodiments, only one nucleic acid barcode sequence is associated with a given discrete partition (e.g., a well or a droplet), although in some cases, two or more different barcode sequences may be present. The nucleic acid barcode sequences can include from about 6 to about 20 or more nucleotides within the sequence of the nucleic acid molecules (e.g., oligonucleotides). In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

In some embodiments, the nucleic acid barcode molecules can also comprise other functional sequences useful in the processing of the nucleic acids from the biological sample in the partition (e.g., the well or the droplet). These functional sequences can include, e.g., targeted or random/universal amplification primer sequences for amplifying the nucleic acid molecules from the individual biological samples within the partitions while attaching the associated barcode sequences, sequencing primers or primer recognition sites, hybridization or probing sequences, e.g., for identification of presence of the sequences or for pulling down barcoded nucleic acid molecules, or any of a number of other potential functional sequences.

In some embodiments, large numbers of nucleic acid barcode molecules (e.g., oligonucleotides) are releasably attached to beads, wherein all of the nucleic acid molecules attached to a particular bead will include the same nucleic acid barcode sequence, but where a large number of diverse barcode sequences are represented across the population of beads used. In some embodiments, gel beads (e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more.

The nucleic acid barcode molecules can be released from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for provision or encapsulation of biological samples and may be degraded for release of the attached nucleic acid molecules through exposure to a reducing agent, such as DTT.

H. Use of Fixed Biological Samples and Unfixing Agents in Partition-Based Assays As disclosed elsewhere herein, the compositions and methods of the present disclosure allow for the preparation of a biological sample that has been fixed with a bis-imidazole-carboxylate compound of formula (I) to be provided in a discrete partition (e.g., provided in a discrete well, or provided or encapsulated in a discrete droplet (optionally, as a single cell)), optionally, together with a lysis agent and/or an unfixing agent that is capable of reversing bis-carbamate crosslinks of the sample, and thereby allowing the cellular analytes of the sample to be assayed as if they were obtained from a fresh biological sample. In one embodiment, a single cell (e.g., a single fixed cell) is provided in a discrete partition. The fixing reagent compounds, methods, and associated unfixing agents of the present disclosure allow for a fresh biological sample to be immediately preserved, and then stored for a period of time before it is provided in a partition (e.g., provided in a well, or provided in or encapsulated in a droplet) with a lysis agent and/or an unfixing agent. Typically, other materials, such as a unique nucleic acid barcode molecule and assay reagents are also provided in the partition (e.g., provided in the well, or provided or encapsulated in the droplet). Accordingly, it is contemplated that the methods of the present disclosure can be carried out wherein the amount of time between the fixation of the biological sample with a bis-imidazole-carboxylate compound of formula (I) and providing the sample in a discrete partition (e.g., in a well, in a droplet, or by encapsulation in a discrete droplet) for processing is at least 1 hour, at least 2 hours, at least 6 hours, at least 12 hours, at least 24 hours, at least 72 hours, at least 1 week, at least 1 month, at least 6 months, or longer.

Generally, it is contemplated that any of the methods for preparing a biological sample using a fixing reagent composition comprising a compounds of formula (I) (including compounds of formulas (II), (III), (IV), (V), or compound (6)) disclosed herein can also be used to prepare a fixed biological sample that is provided in a partition (e.g., provided in a well or encapsulated in a droplet), optionally, together with a lysis agent and/or an unfixing agent. Similarly, it is contemplated that any of the compositions disclosed herein comprising bis-carbamate crosslinked biomolecules of formula (Ia) (including compounds of formulas (IIa), (IIIa), (Iva), (Va), or (VIa)) can be provided in a partition (e.g., provided in a well or encapsulated in a droplet) with an unfixing agent and used in a partition-based assay method (e.g., a well- or a droplet-based assay method). Accordingly, in at least one embodiment, the present disclosure provides an assay method comprising:

(a) generating a discrete partition comprising a fixed biological sample (a well comprising or a droplet comprising or encapsulating a fixed biological sample), a lysis and/or an unfixing agent, and assay reagents, wherein the fixed sample comprises a crosslinked biomolecule of formula (Ia)

(Ia)

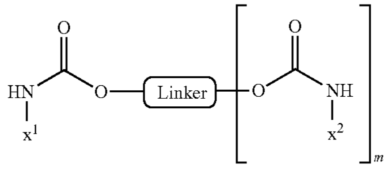

wherein, $X^1$ and $X^2$ are amine-bearing moieties of the same or different biomolecules of the sample; "Linker" comprises an ethylene glycol moiety, and/or a linear or branched alkane moiety of 2-24 carbons; and m is 1 to 12; the unfixing agent comprises a compound capable of cleaving a carbamate bond; optionally, wherein the compound capable of cleaving a carbamate bond selected from DETA, EDA, hydrazine monohydrate, a carboxyesterase, or a combination thereof; and (b) detecting analytes from the reaction of the assay reagents and the un-fixed biological sample.

Optionally, the steps of the assay method can further comprise preparing the biological sample by contacting the sample with a fixing reagent composition comprising a compound of formula (I) prior to generating the discrete partition (e.g., the well or the droplet).

A wide range of droplet-based assays and systems are known in the art. Assays and systems that are suitable for use with the compositions and methods of the present disclosure include, without limitation, those described in U.S. Pat. Nos. 9,694,361, 10,357,771, 10,273,541, and 10,011,872, as well as US Published Patent Application Nos. 20180105808, 20190367982, and 20190338353, each of which is incorporated herein by reference in its entirety. It is contemplated that any assay that can be carried out using a fresh biological sample, such as a single cell provided in or encapsulated in a droplet with a bead carrying a barcode, can also be carried out using a fixed biological sample, prepared using the fixing reagents, and associated methods of the present disclosure. That is, in any droplet-based assay using a fresh biological sample, the droplet-based assay protocol can also be carried out wherein the fresh biological sample is fixed prior to running the assay protocol. In such an assay the protocol can comprise providing or encapsulating the fixed biological sample in a discrete droplet together with a lysis agent and/or an unfixing agent and assay reagents.

In some embodiments of the assay methods, the discrete partition (e.g., a well or a droplet) further comprises one or more beads. In some embodiments, the bead(s) can contain the assay reagents and/or the unfixing agent. In some embodiments, a barcode is carried by or contained in a bead. Compositions, methods and systems for sample preparation, amplification, and sequencing of biomolecules from single cells encapsulated with barcodes in droplets are provided in e.g., US Pat. Publication No. 20180216162A1, which is hereby incorporated by reference herein.

Assay reagents can include those used to perform one or more additional chemical or biochemical operations on a biological sample provided or encapsulated in a partition (e.g., in a well, in a droplet, or encapsulated in a droplet). Accordingly, assay reagents useful in the assay method include any reagents useful in performing a reaction such as nucleic acid modification (e.g., ligation, digestion, methylation, random mutagenesis, bisulfite conversion, uracil hydrolysis, nucleic acid repair, capping, or decapping), nucleic acid amplification (e.g., isothermal amplification or PCR), nucleic acid insertion or cleavage (e.g., via CRISPR/Cas9-mediated or transposon-mediated insertion or cleavage), and/or reverse transcription. Additionally, useful assay reagents can include those that allow the preparation of a target sequence or sequencing reads that are specific to the macromolecular constituents of interest at a higher rate than to non-target sequence specific reads.

In addition, the present disclosure provides compositions and systems related to the analysis of fixed biological samples. In one embodiment, the present disclosure provides a composition comprising a plurality of partitions, wherein a subset of said plurality of partitions comprises cells fixed using a fixing reagent composition and/or associated methods described herein. The partitions may further comprise a lysis agent and/or an unfixing agent. In another embodiment, a partition of the plurality of partitions comprises a fixed cell and a lysis agent and/or an unfixing agent. In certain embodiments, the fixed cell is a single fixed cell. In other embodiments the present disclosure provides a composition comprising a partition, wherein the partition comprises a fixed cell, prepared with a fixing reagent of the present disclosure, a lysis agent and/or an unfixing agent, as described herein. The partition may be a droplet or a well. In another embodiment, the partition can further comprise a protease. In another embodiment, the partition or partitions described herein comprising a fixed cell may further comprise assay reagents, optionally where the assay reagents comprise one or more of the following: a reverse transcriptase, a bead, and reagents for a nucleic acid extension reaction. In an additional embodiment, the compositions of the present disclosure have or are provided at a temperature other than ambient temperature or non-ambient temperature. In one embodiment, the temperature is below ambient temperature or above ambient temperature.

As described elsewhere herein, partitioning approaches may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions. For example, an occupied partition according the present disclosure comprises a fixed cell (e.g., fixed according to a fixing reagent composition as described herein) and an unfixing agent.

In another aspect, the present disclosure concerns methods and compositions for the partitioning of a plurality of fixed cells (e.g., fixed according to a fixing reagent composition as described herein) into individual partitions. In some cases, about 10, about 20, about 30, about 40, about 50, about 60, about 70, about 80, about 90, about 100, about 200, about 300, about 400, about 500, about 600, about 700, about 800, about 900, about 1000, about 2000, about 3000, about 4000, about 5000, about 6000, about 7000, about 8000, about 9000, about 10,000, about 15,000, about 20,000, about 25,000, about 30,000, about 35,000, about 40,000, about 50,000, about 60,000, about 70,000, about 80,000, about 90,000 or about 100,000 fixed cells may be partitioned into individual partitions. In some instances, the method further comprises partitioning about 50 to about 20,000 fixed cells with each of a plurality of supports comprising the adaptor comprising the barcode sequence, wherein the barcode sequence is unique among each of the plurality of supports.

Figure 10:
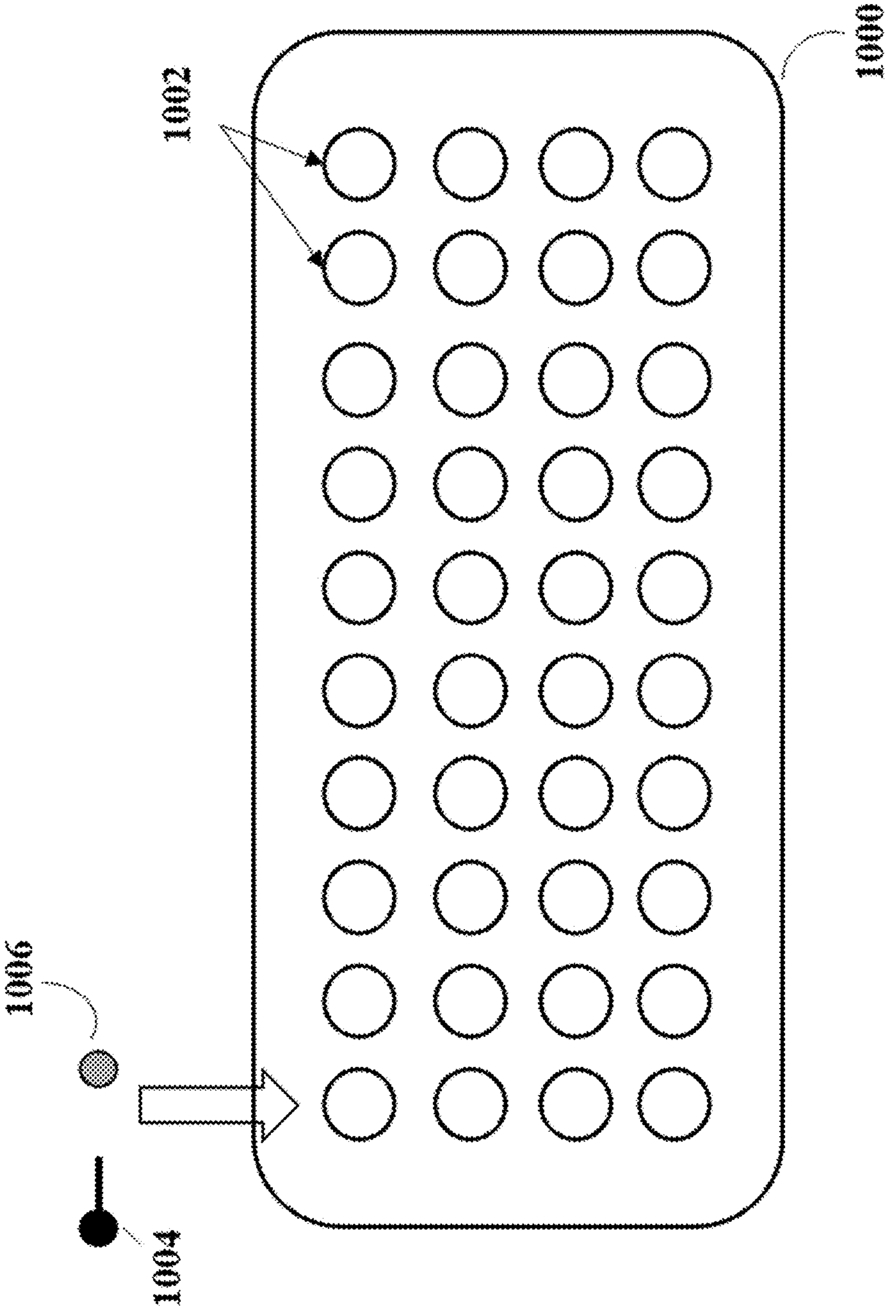
FIG. 10 shows an exemplary microwell array schematic.

FIG. 10 schematically illustrates an example of a microwell array. The array can be contained within a substrate 1000. The substrate 1000 comprises a plurality of wells 1002. The wells 1002 may be of any size or shape, and the spacing between the wells, the number of wells per substrate, as well as the density of the wells on the substrate 1000 can be modified, depending on the particular application. In one such example application, a sample molecule 1006, which may comprise a cell (e.g., a fixed cell or an un-fixed cell) or cellular components (e.g., nucleic acid molecules) is co-partitioned with a bead 1004, which may comprise a nucleic acid barcode molecule coupled thereto. The wells 1002 may be loaded using gravity or other loading technique (e.g., centrifugation, liquid handler, acoustic loading, optoelectronic, etc.). In some instances, at least one of the wells 1002 contains a single sample molecule 1006 (e.g., cell) and a single bead 1004.

Reagents may be loaded into a well either sequentially or concurrently. In some cases, reagents are introduced to the device either before or after a particular operation. In some cases, reagents (which may be provided, in certain instances, in droplets or beads) are introduced sequentially such that different reactions or operations occur at different steps. The reagents (or droplets or beads) may also be loaded at operations interspersed with a reaction or operation step. For example, droplets or beads comprising reagents for fragmenting polynucleotides (e.g., restriction enzymes) and/or other enzymes (e.g., transposases, ligases, polymerases, etc.) may be loaded into the well or plurality of wells, followed by loading of droplets or beads comprising reagents for attaching nucleic acid barcode molecules to a sample nucleic acid molecule. Reagents may be provided concurrently or sequentially with a sample, such as a cell (e.g., a fixed cell or an un-fixed cell) or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a bead or droplet. These beads or droplets may be loaded into a partition (e.g., a microwell) before, after, or concurrently with the loading of a cell (e.g., a fixed cell or an un-fixed cell), such that each cell is contacted with a different bead or droplet. This technique may be used to attach a unique nucleic acid barcode molecule to nucleic acid molecules obtained from each cell (e.g., a fixed cell or an un-fixed cell). Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell, e.g., a single fixed cell or a single un-fixed cell) and a single bead (such as those described herein, which may, in some instances, also be provided or encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where cells, e.g., fixed cells or un-fixed cells are loaded in the microwells, one of the droplets may comprise reagents for further processing, e.g., lysis reagents for lysing the cell, upon droplet merging.

A droplet or support (e.g., a bead) may be partitioned into a well. The droplets may be selected or subjected to pre-processing prior to loading into a well. For instance, the droplets may comprise cells, e.g., fixed cells or un-fixed cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell (e.g., a fixed cell or an un-fixed cell) distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell or cellular components) or derivatives thereof. Characterization techniques such as microscopy or imaging may be useful in measuring sample profiles in fixed spatial locations. For instance, when cells (e.g., fixed cells or un-fixed cells) are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, cell-cell interactions (when two or more cells are co-partitioned). Alternatively or in addition to, imaging may be used to characterize a quantity of amplification products in the well.

In operation, a well may be loaded with a sample and reagents, simultaneously or sequentially. When cells (e.g., fixed cells or un-fixed cells) are loaded, the well may be subjected to washing, e.g., to remove excess cells from the well, microwell array, or plate. Similarly, washing may be performed to remove excess beads or other reagents from the well, microwell array, or plate. In addition, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 11:
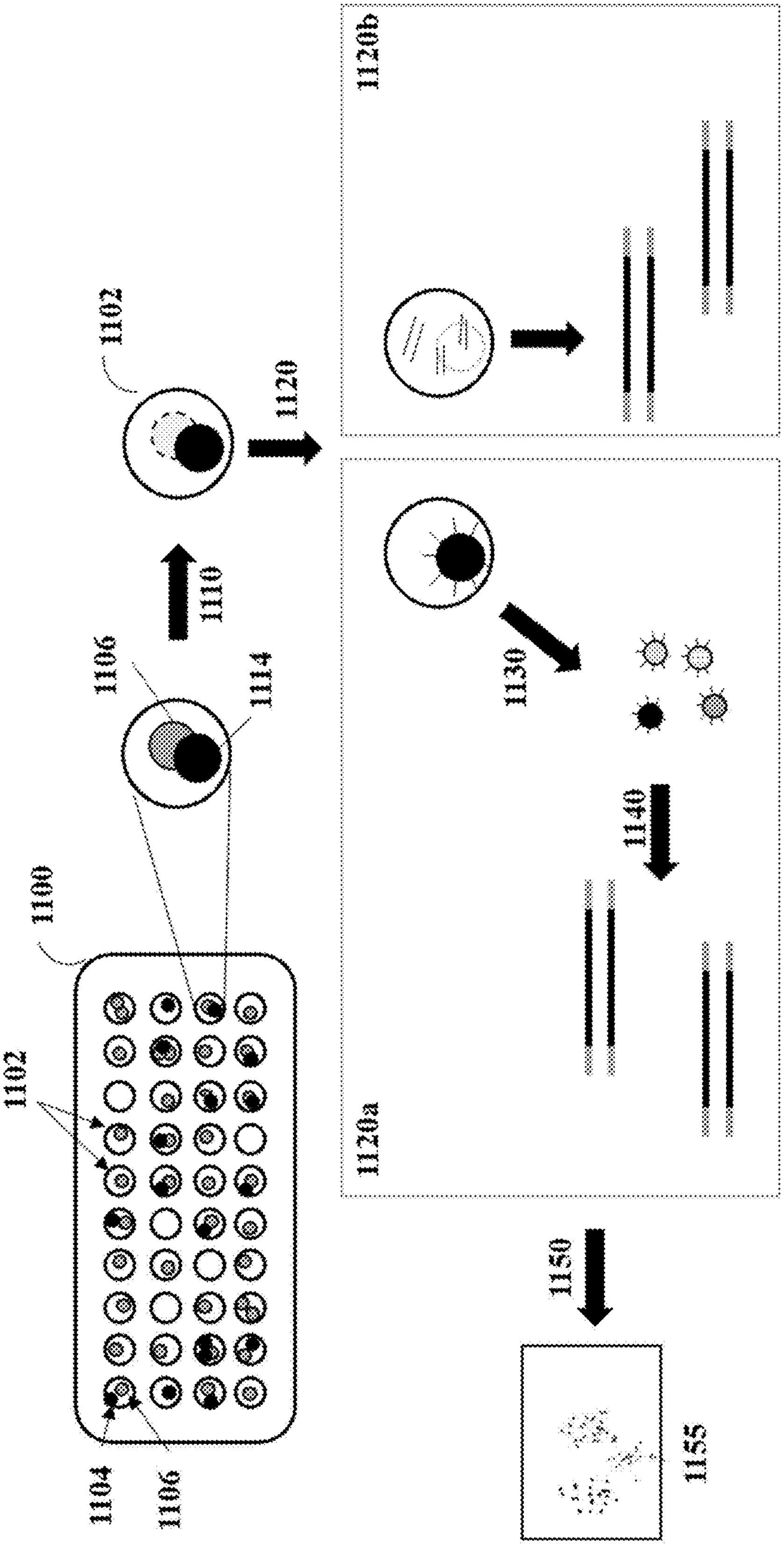
FIG. 11 shows an exemplary microwell array workflow for processing nucleic acid molecules.

FIG. 11 schematically shows an example workflow for processing nucleic acid molecules within a sample. A substrate 1100 comprising a plurality of microwells 1102 may be provided. A sample 1106 which may comprise a cell (e.g., a fixed cell or an un-fixed cell), cellular components or analytes (e.g., proteins and/or nucleic acid molecules) can be co-partitioned, in a plurality of microwells 1102, with a plurality of beads 1104 comprising nucleic acid barcode molecules. During process 1110, the sample 1106 may be processed within the partition. For instance, the cell may be subjected to conditions sufficient to lyse the cells (e.g., fixed cells or un-fixed cells) and release the analytes contained therein. In process 1120, the bead 1104 may be further processed. By way of example, processes 1120*a* and 1120*b* schematically illustrate different workflows, depending on the properties of the bead 1104.

In 1120*a*, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 1130, the beads 1104 from multiple wells 1102 may be collected and pooled. Further processing may be performed in process 1140. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1150, further characterization, such as sequencing may be performed to generate sequencing reads. The sequencing reads may yield information on individual cells or populations of cells (e.g., fixed cells or un-fixed cells), which may be represented visually or graphically, e.g., in a plot 1155.

In 1120*b*, the bead comprises nucleic acid barcode molecules that are releasably attached thereto, as described below. The bead may degrade or otherwise release the nucleic acid barcode molecules into the well 1102; the nucleic acid barcode molecules may then be used to barcode nucleic acid molecules within the well 1102. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1150, further characterization, such as sequencing may be performed to generate sequencing reads. The sequencing reads may yield information on individual cells or populations of cells (e.g., fixed cells or un-fixed cells), which may be represented visually or graphically, e.g., in a plot 1155

In 1120*b*, the bead comprises nucleic acid barcode molecules that are releasably attached thereto, as described below. The bead may degrade or otherwise release the nucleic acid barcode molecules into the well 1102; the nucleic acid barcode molecules may then be used to barcode nucleic acid molecules within the well 1102. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1150, further characterization, such as sequencing may be performed to generate sequencing reads. The sequencing reads may yield information on individual cells or populations of cells (e.g., fixed cells or un-fixed cells), which may be represented visually or graphically, e.g., in a plot 1155.

I. Additional Partition-Based Methods

The present disclosure provides methods and systems for multiplexing, and otherwise increasing throughput of samples for analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cells or cell features may be used to characterize cells and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, each of which is herein entirely incorporated by reference for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In other aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

For workflows comprising the use of fixation agents and/or un-fixing agents, labelling agents may be used to label samples (e.g., cells, fixed cells or un-fixed cells) at different points in time. In one embodiment, a plurality of cells is labeled prior to treatment with a fixation agent and/or after treatment with a fixation agent. In another embodiment, a plurality of fixed cells is labeled prior to treatment with an un-fixing agent and/or after treatment with an un-fixing agent. In one additional embodiment, a plurality of un-fixed cells is labeled prior to partitioning into partitions (e.g., wells or droplets) for further processing. In another embodiment, the methods, compositions, systems, and kits described herein provide labeled cells, labeled fixed cells or labeled un-fixed cells.

Labelling agents capable of binding to or otherwise coupling to one or more cells (including fixed cells and un-fixed cells) may be used to characterize a cell as belonging to a particular set of cells. For example, labeling agents may be used to label a sample of cells or a group of cells (including fixed cells and un-fixed cells). In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling a cell (including a fixed or an un-fixed cell) may comprise subjecting the antibody-linked barcode molecule or the epitope binding fragment-linked barcode molecule to conditions suitable for binding the antibody to a molecule present on a surface of the cell. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 μM, 90 μM, 80 μM, 70 μM, 60 μM, 50 μM, 40 μM, 30 μM, 20 μM, 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 μM.

In another example, a reporter oligonucleotide may be coupled to a cell-penetrating peptide (CPP), and labeling cells may comprise delivering the CPP coupled reporter oligonucleotide into an analyte carrier. Labeling analyte carriers may comprise delivering the CPP conjugated oligonucleotide into a cell and/or cell bead by the cell-penetrating peptide. A CPP that can be used in the methods provided herein can comprise at least one non-functional cysteine residue, which may be either free or derivatized to form a disulfide link with an oligonucleotide that has been modified for such linkage. Non-limiting examples of CPPs that can be used in embodiments herein include penetratin, transportan, plsl, TAT (48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The CPP may be an arginine-rich peptide transporter. The CPP may be Penetratin or the Tat peptide. In another example, a reporter oligonucleotide may be coupled to a fluorophore or dye, and labeling cells may comprise subjecting the fluorophore-linked barcode molecule to conditions suitable for binding the fluorophore to the surface of the cell. In some instances, fluorophores can interact strongly with lipid bilayers and labeling cells may comprise subjecting the fluorophore-linked barcode molecule to conditions such that the fluorophore binds to or is inserted into a membrane of the cell. In some cases, the fluorophore is a water-soluble, organic fluorophore. In some instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. PLoS One. 2014 Feb. 4; 9(2):e87649, which is hereby incorporated by reference in its entirety for all purposes, for a description of organic fluorophores.

A reporter oligonucleotide may be coupled to a lipophilic molecule, and labeling cells may comprise delivering the nucleic acid barcode molecule to a membrane of a cell or a nuclear membrane by the lipophilic molecule. Lipophilic molecules can associate with and/or insert into lipid membranes such as cell membranes and nuclear membranes. In some cases, the insertion can be reversible, in some cases, the association between the lipophilic molecule and the cell or nuclear membrane may be such that the membrane retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus. In one embodiment, a reporter oligonucleotide coupled to a lipophilic molecule will remain associated with and/or inserted into lipid membrane (as described herein) via the lipophilic molecule until lysis of the cell occurs, e.g., inside a partition.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

As described elsewhere herein, libraries of labelling agents may be associated with a particular cell feature as well as be used to identify analytes as originating from a particular cell population, or sample. Cell populations may be incubated with a plurality of libraries such that a cell or cells comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 12:
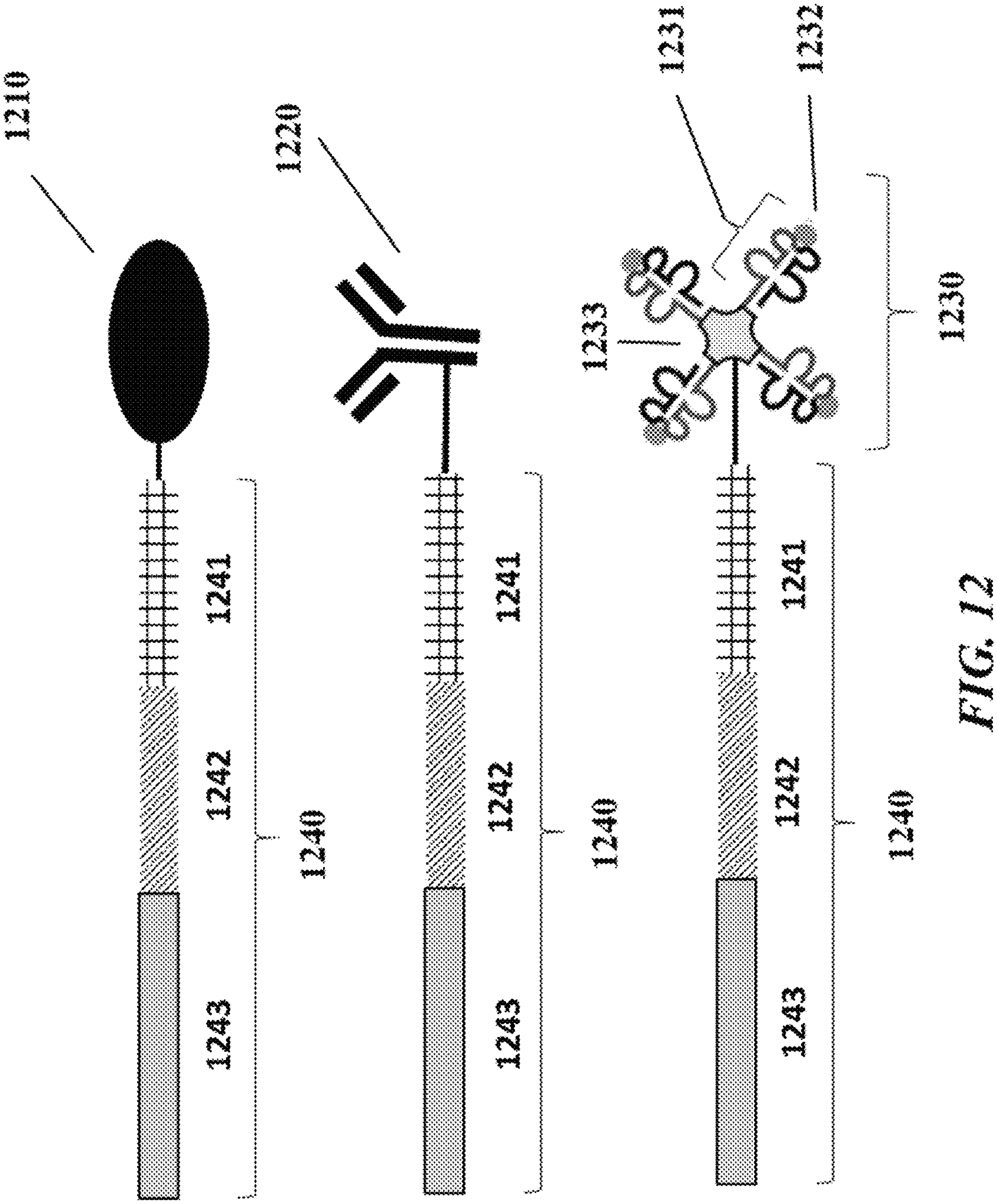
FIG. 12 schematically illustrates examples of labelling agents.

FIG. 12 describes exemplary labelling agents (1210, 1220, 1230) comprising reporter oligonucleotides (1240) attached thereto. Labelling agent 1210 (e.g., any of the labelling agents described herein) is attached (either directly, e.g., covalently attached, or indirectly) to reporter oligonucleotide 1240. Reporter oligonucleotide 1240 may comprise barcode sequence 1242 that identifies labelling agent 1210. Reporter oligonucleotide 1240 may also comprise one or more functional sequences 1243 that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 12, in some instances, reporter oligonucleotide 1240 conjugated to a labelling agent (e.g., 1210, 1220, 1230) comprises a primer sequence 1241, a barcode sequence 1242 that identifies the labelling agent (e.g., 1210, 1220, 1230), and functional sequence 1243. Functional sequence 1243 may be configured to hybridize to a complementary sequence, such as a complementary sequence present on a nucleic acid barcode molecule 1290 (not shown), such as those described elsewhere herein. In some instances, nucleic acid barcode molecule 1290 is attached to a support (e.g., a bead, such as a gel bead), such as those described elsewhere herein. For example, nucleic acid barcode molecule 1290 may be attached to the support via a releasable linkage (e.g., comprising a labile bond), such as those described elsewhere herein. In some instances, reporter oligonucleotide 1240 comprises one or more additional functional sequences, such as those described above.

In some instances, the labelling agent 1210 is a protein or polypeptide (e.g., an antigen or prospective antigen) comprising reporter oligonucleotide 1240. Reporter oligonucleotide 1240 comprises barcode sequence 1242 that identifies polypeptide 1210 and can be used to infer the presence of an analyte, e.g., a binding partner of polypeptide 1210 (i.e., a molecule or compound to which polypeptide 1210 can bind). In some instances, the labelling agent 1210 is a lipophilic moiety (e.g., cholesterol) comprising reporter oligonucleotide 1240, where the lipophilic moiety is selected such that labelling agent 1210 integrates into a membrane of a cell or nucleus. Reporter oligonucleotide 1240 comprises barcode sequence 1242 that identifies lipophilic moiety 1210 which in some instances is used to tag cells (e.g., groups of cells, cell samples, etc.) and may be used for multiplex analyses as described elsewhere herein. In some instances, the labelling agent is an antibody 1220 (or an epitope binding fragment thereof) comprising reporter oligonucleotide 1240. Reporter oligonucleotide 1240 comprises barcode sequence 1242 that identifies antibody 1220 and can be used to infer the presence of, e.g., a target of antibody 1220 (i.e., a molecule or compound to which antibody 1220 binds). In other embodiments, labelling agent 1230 comprises an MHC molecule 1231 comprising peptide 1232 and reporter oligonucleotide 1240 that identifies peptide 1232. In some instances, the MHC molecule is coupled to a support 1233. In some instances, support 1233 may be a polypeptide, such as streptavidin, or a polysaccharide, such as dextran. In some instances, reporter oligonucleotide 1240 may be directly or indirectly coupled to MHC labelling agent 1230 in any suitable manner. For example, reporter oligonucleotide 1240 may be coupled to MHC molecule 1231, support 1233, or peptide 1232. In some embodiments, labelling agent 1230 comprises a plurality of MHC molecules, (e.g. is an MHC multimer, which may be coupled to a support (e.g., 1233)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

Figure 13:
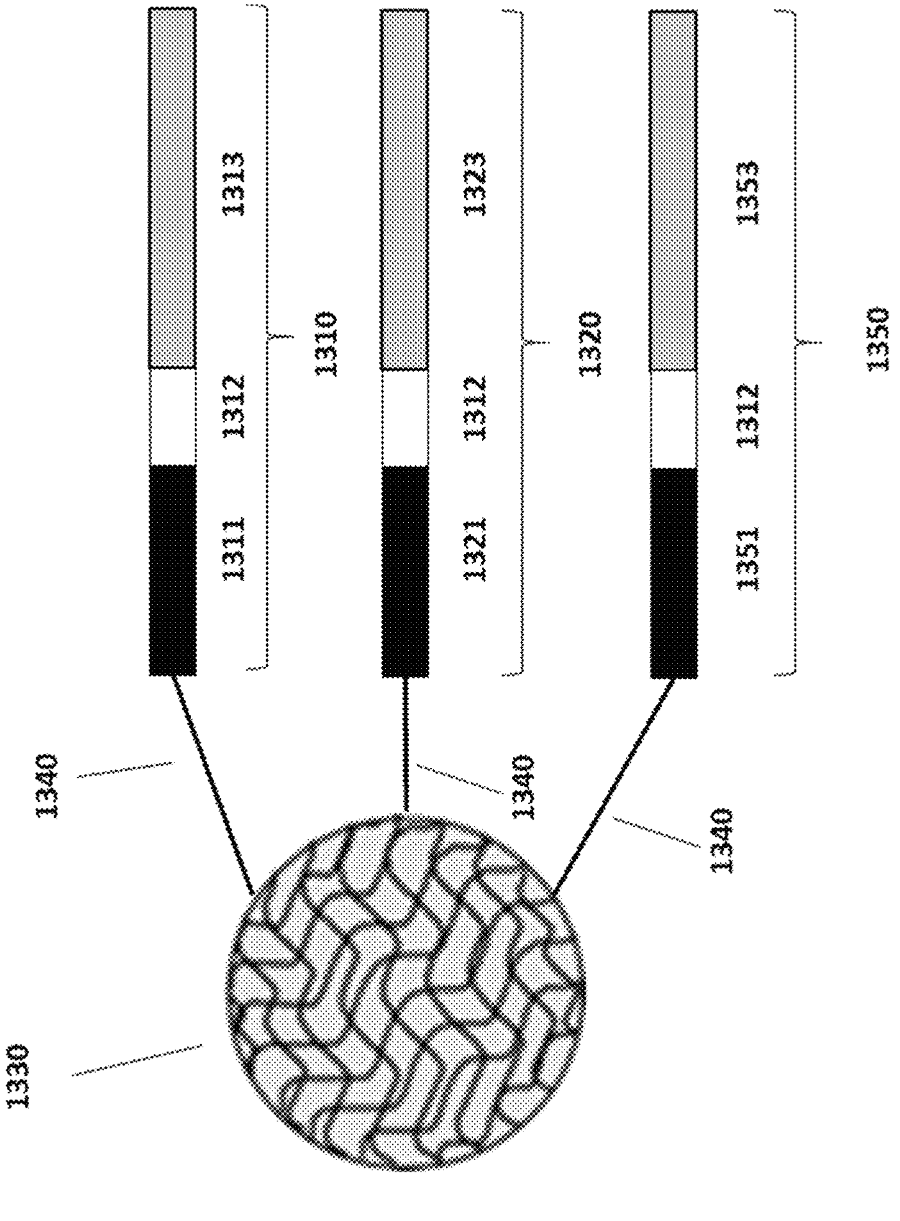
FIG. 13 depicts an example of a barcode carrying bead.

FIG. 13 illustrates another example of a barcode carrying bead. In some embodiments, analysis of multiple analytes (e.g., RNA and one or more analytes using labelling agents described herein) may comprise nucleic acid barcode molecules as generally depicted in FIG. 13. In some embodiments, nucleic acid barcode molecules 1310 and 1320 are attached to support 1330 via a releasable linkage 1340 (e.g., comprising a labile bond) as described elsewhere herein. Nucleic acid barcode molecule 1310 may comprise adapter sequence 1311, barcode sequence 1312 and adapter sequence 1313. Nucleic acid barcode molecule 1320 may comprise adapter sequence 1321, barcode sequence 1312, and adapter sequence 1323, wherein adapter sequence 1323 comprises a different sequence than adapter sequence 1313. In some instances, adapter 1311 and adapter 1321 comprise the same sequence. In some instances, adapter 1311 and adapter 1321 comprise different sequences. Although support 1330 is shown comprising nucleic acid barcode molecules 1310 and 1320, any suitable number of barcode molecules comprising common barcode sequence 1312 are contemplated herein. For example, in some embodiments, support 1330 further comprises nucleic acid barcode molecule 1350. Nucleic acid barcode molecule 1350 may comprise adapter sequence 1351, barcode sequence 1312 and adapter sequence 1353, wherein adapter sequence 1353 comprises a different sequence than adapter sequence 1313 and 1323. In some instances, nucleic acid barcode molecules (e.g., 1310, 1320, 1350) comprise one or more additional functional sequences, such as a UMI or other sequences described herein. The nucleic acid barcode molecules 1310, 1320 or 1350 may interact with analytes as described elsewhere herein, for example, as depicted in FIGS. 14A-C.

Figure 14A:
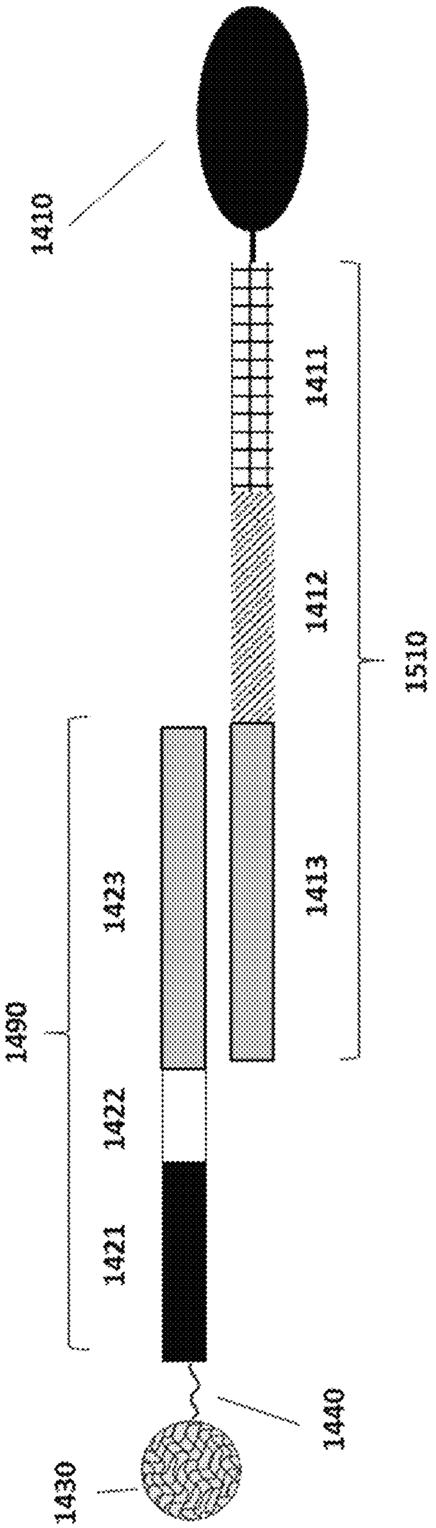
FIGS. 14A, 14B, and 14C schematically depict an example workflow for processing nucleic acid molecules.

Referring to FIG. 14A, in an instance where cells are labelled with labeling agents, sequence 1423 may be complementary to an adapter sequence of a reporter oligonucleotide. Cells may be contacted with one or more reporter oligonucleotide 1510 conjugated labelling agents 1410 (e.g., polypeptide, antibody, or others described elsewhere herein). In some cases, the cells may be further processed prior to barcoding. For example, such processing steps may include one or more washing and/or cell sorting steps. In some instances, a cell that is bound to labelling agent 1410 which is conjugated to oligonucleotide 1510 and support 1430 (e.g., a bead, such as a gel bead) comprising nucleic acid barcode molecule 1490 is partitioned into a partition amongst a plurality of partitions (e.g., a droplet of a droplet emulsion or a well of a microwell array). In some instances, the partition comprises at most a single cell bound to labelling agent 1410. In some instances, reporter oligonucleotide 1510 conjugated to labelling agent 1410 (e.g., polypeptide, an antibody, pMHC molecule such as an MHC multimer, etc.) comprises a first adapter sequence 1411 (e.g., a primer sequence), a barcode sequence 1412 that identifies the labelling agent 1410 (e.g., the polypeptide, antibody, or peptide of a pMHC molecule or complex), and an adapter sequence 1413. Adapter sequence 1413 may be configured to hybridize to a complementary sequence, such as sequence 1423 present on a nucleic acid barcode molecule 1490. In some instances, oligonucleotide 1510 comprises one or more additional functional sequences, such as those described elsewhere herein.

Figure 14B:
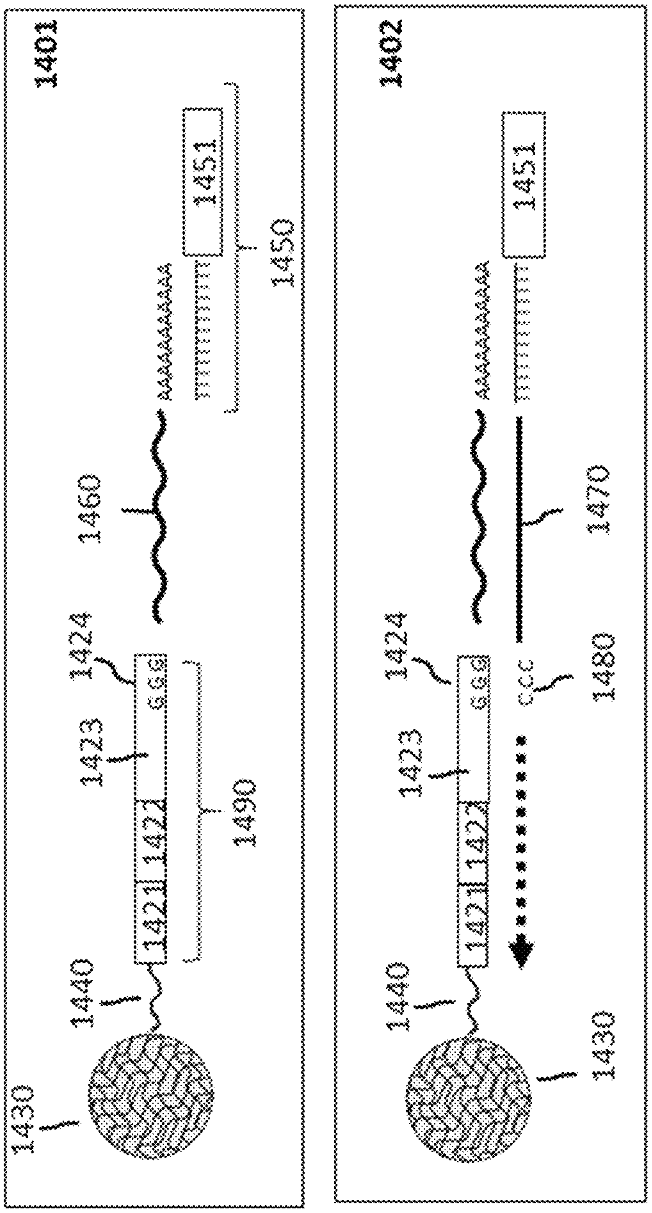
Figure 14C:
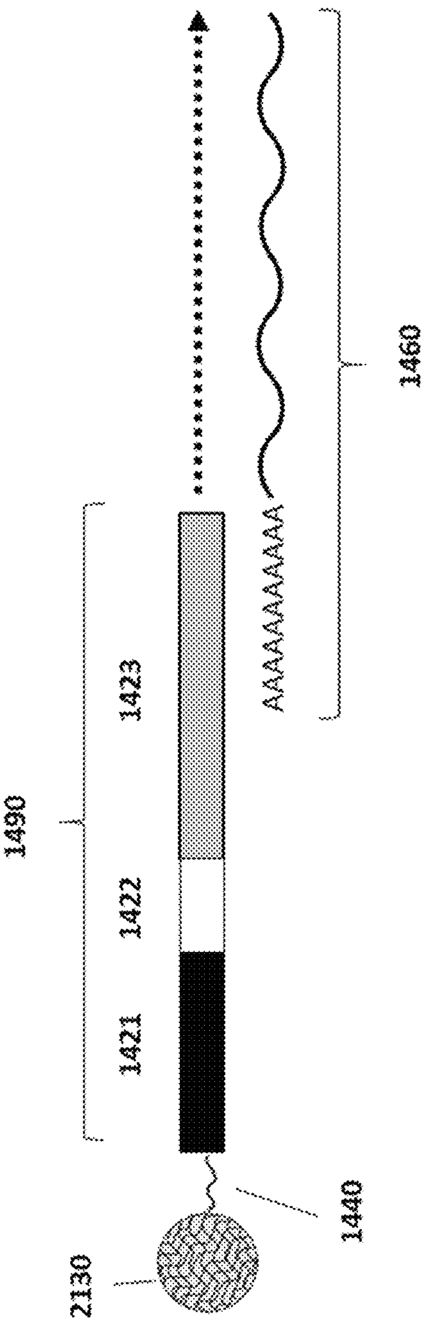

Barcoded nucleic may be generated (e.g., via a nucleic acid reaction, such as nucleic acid extension or ligation) from the constructs described in FIGS. 14A-C. For example, sequence 1413 may then be hybridized to complementary sequence 1423 to generate (e.g., via a nucleic acid reaction, such as nucleic acid extension or ligation) a barcoded nucleic acid molecule comprising cell (e.g., partition specific) barcode sequence 1422 (or a reverse complement thereof) and reporter sequence 1412 (or a reverse complement thereof). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 14A-C, or a combination of workflows for an individual analyte, as described elsewhere herein. For example, by using a combination of the workflows as generally depicted in FIGS. 14A-C, multiple analytes can be analyzed.

In some instances, analysis of an analyte (e.g. a nucleic acid, a polypeptide, a carbohydrate, a lipid, etc.) comprises a workflow as generally depicted in FIG. 14A. A nucleic acid barcode molecule 1490 may be co-partitioned with the one or more analytes. In some instances, nucleic acid barcode molecule 1490 is attached to a support 1430 (e.g., a bead, such as a gel bead), such as those described elsewhere herein. For example, nucleic acid barcode molecule 1490 may be attached to support 1430 via a releasable linkage 1440 (e.g., comprising a labile bond), such as those described elsewhere herein. Nucleic acid barcode molecule 1490 may comprise a barcode sequence 1421 and optionally comprise other additional sequences, for example, a UMI sequence 1422 (or other functional sequences described elsewhere herein). The nucleic acid barcode molecule 1490 may comprise a sequence 1423 that may be complementary to another nucleic acid sequence, such that it may hybridize to a particular sequence.

For example, sequence 1423 may comprise a poly-T sequence and may be used to hybridize to mRNA. Referring to FIG. 14C, in some embodiments, nucleic acid barcode molecule 1490 comprises sequence 1423 complementary to a sequence of RNA molecule 1460 from a cell. In some instances, sequence 1423 comprises a sequence specific for an RNA molecule. Sequence 1423 may comprise a known or targeted sequence or a random sequence. In some instances, a nucleic acid extension reaction may be performed, thereby generating a barcoded nucleic acid product comprising sequence 1423, the barcode sequence 1421, UMI sequence 1422, any other functional sequence, and a sequence corresponding to the RNA molecule 1460.

In another example, sequence 1423 may be complementary to an overhang sequence or an adapter sequence that has been appended to an analyte. For example, referring to FIG. 14B, in some embodiments, primer 1450 comprises a sequence complementary to a sequence of nucleic acid molecule 1460 (such as an RNA encoding for a BCR sequence) from an analyte carrier. In some instances, primer 1450 comprises one or more sequences 1451 that are not complementary to RNA molecule 1460. Sequence 1451 may be a functional sequence as described elsewhere herein, for example, an adapter sequence, a sequencing primer sequence, or a sequence the facilitates coupling to a flow cell of a sequencer. In some instances, primer 1450 comprises a poly-T sequence. In some instances, primer 1450 comprises a sequence complementary to a target sequence in an RNA molecule. In some instances, primer 1450 comprises a sequence complementary to a region of an immune molecule, such as the constant region of a TCR or BCR sequence. Primer 1450 is hybridized to nucleic acid molecule 1460 and complementary molecule 1470 is generated. For example, complementary molecule 1470 may be cDNA generated in a reverse transcription reaction. In some instances, an additional sequence may be appended to complementary molecule 1470. For example, the reverse transcriptase enzyme may be selected such that several non-templated bases 1480 (e.g., a poly-C sequence) are appended to the cDNA. In another example, a terminal transferase may also be used to append the additional sequence. Nucleic acid barcode molecule 1490 comprises a sequence 1424 complementary to the non-templated bases, and the reverse transcriptase performs a template switching reaction onto nucleic acid barcode molecule 1490 to generate a barcoded nucleic acid molecule comprising cell (e.g., partition specific) barcode sequence 1422 (or a reverse complement thereof) and a sequence of complementary molecule 1470 (or a portion thereof). In some instances, sequence 1423 comprises a sequence complementary to a region of an immune molecule, such as the constant region of a TCR or BCR sequence. Sequence 1423 is hybridized to nucleic acid molecule 1460 and a complementary molecule 1470 is generated. For example, complementary molecule 1470 may be generated in a reverse transcription reaction generating a barcoded nucleic acid molecule comprising cell (e.g., partition specific) barcode sequence 1422 (or a reverse complement thereof) and a sequence of complementary molecule 1470 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in international Patent Application WO2018/075693, U.S. Patent Publication No, 2018/0105808, U.S. Patent Publication No. 2015/0376609, filed Jun. 26, 2015, and U.S. Patent Publication No, 2019/0367969, each of which applications is herein entirely incorporated by reference for all purposes,

EXAMPLES

Various features and embodiments of the disclosure are illustrated in the following representative examples, which are intended to be illustrative, and not limiting. Those skilled in the art will readily appreciate that the specific examples are only illustrative of embodiments of the disclosure as described more fully in the claims which follow thereafter. Every embodiment and feature described in the application should be understood to be interchangeable and combinable with every embodiment contained within.

Example 1: Synthesis of a Reversible Fixing Reagent

This example illustrates the synthesis and method of use of a reversible fixing reagent of the present disclosure, ethane-1,2-diyl bis(1H-imidazole-1-carboxylate) (compound (2a)). The fixing reagent of compound (2a) reacts with the amine-bearing moieties of biomolecules in a biological sample to forms bis-carbamate crosslinks that are reversible upon treatment with an unfixing agent that cleaves carbamate bonds, such as DETA.

Synthesis of compound (2a): The synthesis of compound (2a) is summarized in Scheme 7.

Scheme 7

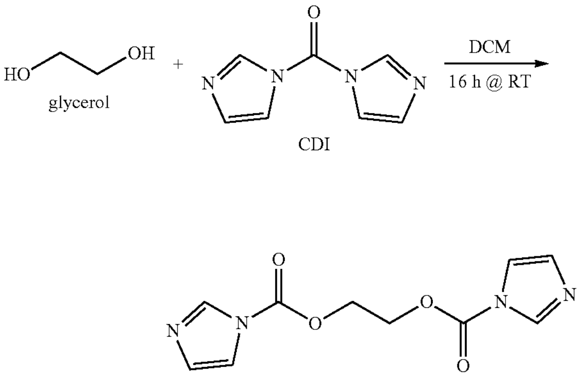

(2a)

All reagents were obtained commercially (Millipore Sigma) and used without further purification. 20 g carbonyldiimdazole ("CDI") (123 mmol, 3.0 eq.) was added to a 250 mL single neck RBF with stir bar. 100 mL dichloromethane ("DCM") solvent was added, and the solution was rapidly stirred to afford a fine white suspension. Glycerol (2.30 mL, 40.1 mmol, 1 eq.) was added via syringe. The reaction vessel was sealed and topped with an Ar balloon to maintain an inert atmosphere. The reaction was allowed to proceed for 16 h and the solution turned from a white suspension to a clear pale yellow. The resulting solution was washed 3× with 100 mL deionized water and dried over $MgSO_4$. The solvent was removed under vacuum to provide a fine white/off-white powder. The formation of the desired product of compound (2a) was confirmed by NMR, which shows 3 peaks between 7.0-8.5 ppm and a single peak for the two $CH_2$ groups of the alkyl bridge. The resulting compound (2a) was used without further purification as a fixing reagent as described in Example 2.

Synthesis of compound (5a): The synthesis of bis-imidazole-glycerol (compound (5a)) is summarized in Scheme 8.

Scheme 8

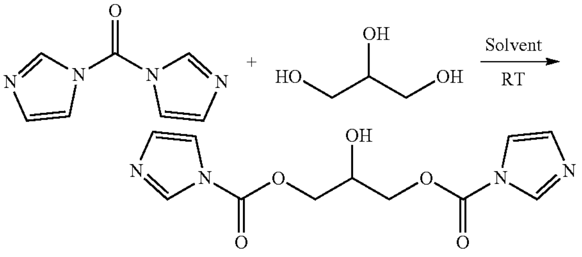

The bis-imidazole glycerol scaffold of compound (5a) is synthesized according to the conditions used for compound (2a) except that 2.5 equivalents of CDI in dichloromethane was added and the reaction allowed to proceed 16 h at RT. The formation of compound (5a) can be identified by $^1H$ NMR by integrating aryl peaks corresponding to imidazole (δ=7.00-8.5 ppm) and $CH_2$ peaks (δ=4.6 ppm) which integrate for 6H and 4H respectively.

Synthesis of compound (5b): The synthesis of acetyl-bis-imidazole-glycerol (compound (5b)) is summarized in Scheme 9.

Scheme 9

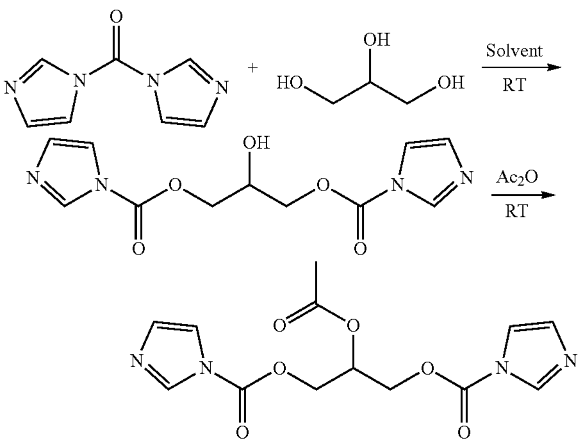

Compound (5b), the acetylated analogue of compound (5a), is synthesized according to the conditions described above for compound (2a) except that after 16 h, 1.5 eq. acetic anhydride is added, and the reaction is allowed to stir for an additional 4 h. The acetylated product is identified by the appearance of a $CH_3$ peak at 6=2.00 ppm and the broadening of multiplets corresponding to the glycerol backbone.

Synthesis of compound (5c): The synthesis of tris-imidazole-glycerol (compound (5c)) is summarized in Scheme 10.

Scheme 10

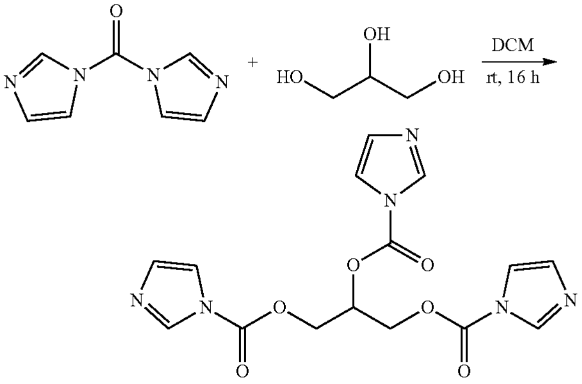

Compound (5c) is synthesized according to the conditions described above for compound (2a) except with an increase to 4-fold excess CDI in dichloromethane. The reaction is allowed to proceed for 16 h at RT. The product is confirmed by the integration of 9 aromatic protons and 5 alkyl protons.

Example 2: Use of a Reversible Fixing Reagent

This example illustrates the use of a reversible fixing reagent, compound (2a). The fixing reagent of compound (2a) reacts with the amine-bearing moieties of biomolecules in a biological sample to forms bis-carbamate crosslinks that are reversible upon treatment with an unfixing agent that cleaves carbamate bonds, such as DETA. This example illustrates the use of compound (2a) to fix PBMCs, which were then stored for up to 21 days followed by un-fixing with DETA to yield RNA.

Fixation of PBMCs: Compound (2a), prepared as described in Example 1, was formulated as a 200 mM stock solution in anhydrous DMSO. The final target fixative solutions were prepared by dilution of the stock solution in PBS to provide the desired concentration. The formulated fixative solutions of compound (2a) were used within 10 mins of formulation to prevent hydrolysis of the reactive imidazole-carboxylates. PBMCs were fixed in 100 μL of 15 mM fixative solution of compound (2a) for either 30 min or 1 h, then quenched with 10% Fetal Bovine Serum (FBS) in PBS. For comparison, separate PBMC samples were fixed in 1 mL of 4% paraformaldehyde ("PFA") in PBS for 20 min and quenched with 10% FBS in PBS. The fixed PBMCs were stored for up to 21 days at either RT, 4° C., or −80° C.

RNA assay of un-fixed PBMCs: At weekly time points, cells from the fixed PBMC samples were centrifuged at 450 g for 5 min, and supernatant was collected and retained. The pellet of the compound (2a)-fixed PBMCs was un-fixed (or "de-crosslinked") by incubation in solutions of 0.1% diethylenetriamine (DETA) in PBS at 50° C. for 15 min or with 0.1% SDS in PBS/0.3% fos-choline in PBS at 40° C. for 2 h. The pellet of the PFA-fixed PBMCs was un-fixed by incubation in 0.1% SDS, 30 mM Tris, pH 6.8 at 40° C. for 2 h. After unfixing agent treatment, the PBMCs were centrifuged at 450 g for 5 min and both pellet (if any) and supernatant were collected.

RNA was isolated from the supernatant obtained before treatment with unfixing agent (labeled "storage solution") and the supernatant collected after the unfixing agent treatment (labeled "supernatant") was isolated using the RNAeasy MinElute Cleanup kit (Qiagen, Cat #74204). RNA from the cell pellets obtained after unfixing agent treatment ("pellet") was isolated using the RNAeasy Plus Mini Kit (Qiagen, Cat #74134). The isolated RNA was evaluated by Qubit™ RNA HS Assay Kit (Invitrogen, Cat #Q32855) and Agilent RNA ScreenTape System (Agilent Technologies).

Results: As shown by the results in Table 3, all samples, fresh or treated with fixing reagent, showed significant leakage of RNA into the storage solution during storage. The samples treated with fixing reagent for 60 minutes and stored for 21 days showed significantly higher RNA recovery from the Pellet and Supernatant with relatively low leakage even after 21 days storage.

Example 3: Solvent Conditions for Use of a Reversible Fixation Reagent

The results of Example 2 suggest some leakage of RNA from PBMCs fixed with compound (2a) and it was hypothesized that the solvent conditions used for fixation, particularly the amount of DMSO present, may contribute to this leakage. This example illustrates experimental studies to determine optimal solvent conditions for use of the reversible fixation reagent, compound (2a), in fixing a biological sample of PBMCs.

Materials and Methods: Compound (2a), was prepared as described in Example 1, and formulated as a 200 mM stock solution in anhydrous DMSO. Fixative solutions of compound (2a) were prepared by dilution of the stock solution in PBS at the following fixative reagent and DMSO concentrations: 15 mM compound (2a) in 15% DMSO; 15 mM compound (2a) in 10% DMSO; 15 mM compound (2a) in 7.5% DMSO; 10 mM compound (2a) in 5% DMSO; or 5 mM compound (2a) in 2.5% DMSO. Fresh PBMCs were fixed in 100 μL of each of the range of fixative solutions for either 30 min or 1 h, then quenched with 100 mM Tris followed by a wash in 10% FBS in PBS.

At Day 0 and Day 3 time points, cells from the fixed PBMC samples were centrifuged at 450 g for 5 min, and supernatant was collected and retained. The pellet of the compound (2a)-fixed cells was un-fixed by incubation in solutions of 1% diethylenetriamine (DETA). After unfixing agent treatment, the samples were centrifuged at 450 g for 5 min and both pellet (if any) and supernatant were collected. RNA was isolated from the supernatant obtained before treatment with unfixing agent (labeled "storage solution") and the supernatant collected after the unfixing agent treatment (labeled "supernatant") was isolated using the RNAeasy MinElute Cleanup Kit (Qiagen, Cat #74204). RNA from the cell pellets obtained after unfixing agent treatment ("pellet") was isolated using the RNAeasy Plus Mini Kit (Qiagen, Cat #74134). RNA isolated was evaluated for mass recovery and quality (Qubit or Tapestation respectively).

Results: It was observed that lower DMSO concentration during fixation with compound (2a) resulted in improved amounts of RNA retention. For example, fixation of cells in the sample with a 2.5% DMSO solution of only 5 mM compound (2a) resulted in significantly higher RNA retention after 3 days at 4 C compared to fixation with a 15 mM solution of compound (2a) in 10% or 15% DMSO.

TABLE 3

| | Conditions | | | | | | | | | | |
|---|---|---|---|---|---|---|---|---|---|---|---|
| | Fixation | Storage | Pellet | | | Supernatant | | | Storage Solution | | |
| Sample | time (min) | time (day) | RNA (ng) | SD | DV200 | RNA (ng) | SD | DV200 | RNA (ng) | SD | DV200 |
| Fresh | 0 | 0 | 159.3 | 0 | 80.1 | | | | 203 | 0 | 66.6 |
| Fresh, 4 C. | 0 | 7 | 340 | 108 | 84.7 | | | | 165 | 68.3 | 71.9 |
| Fresh, 4 C. | 0 | 14 | 9.4 | 2.4 | 67.4 | | | | 63.1 | 13.6 | 54.6 |
| 15 mM, 4 C. | 30 | 0 | 21.4 | 11.8 | 87.6 | 526 | 140 | 93.8 | | | |
| 15 mM, 4 C. | 30 | 7 | 18.4 | 3.2 | 91.5 | 54.0 | 46.1 | 91 | 130 | 95.4 | 87.5 |
| 15 mM, 4 C. | 30 | 14 | 17.2 | 0.84 | 48.8 | 85.0 | 7.4 | 61.6 | 121 | 20.3 | 68.2 |
| 15 mM, 4 C. | 30 | 21 | 16.2 | 5.6 | 81.3 | 363 | 21.8 | 80.7 | 260 | 54.4 | 71.3 |
| 15 mM, 4 C. | 30 | 21 | 16.2 | 5.6 | 81.3 | 363 | 21.8 | 80.7 | 260 | 54.4 | 71.3 |
| 15 mM, 4 C. | 60 | 21 | 211 | 55.8 | 76.0 | 307 | 1.98 | 79.4 | 98.6 | 26.0 | 56.5 |

Example 4: Preparation of a Reversibly Fixed Biological Sample in a Discrete Droplet with a Carbamate-Reversing Unfixing Agent This example illustrates preparation of discrete droplets (GEMs) containing a biological sample of PBMCs previously fixed with compound (2a), and the carbamate-cleaving unfixing agent DETA, and then performing a single-cell RNA sequence expression profiling experiment using the un-fixed samples in the droplets.

Preparation of Fixed Biological Sample:

A fixed biological sample of fixed PBMCs is prepared as described above in Example 1. The fixed biological sample can be stored at 4 C or −20 C for several days or more before being processed in a droplet-based assay (e.g., a single cell assay).

Preparation of Unfixing Agent:

A 0.1% stock solution of the unfixing agent DETA is prepared as described in Example 2.

Generation of Droplets (GEMs) with Fixed Cells, Unfixing Agent, and Barcoded Gel-Beads The fixed biological sample comprising fixed PBMCs is changed into the standard master mix used with the Chromium System (10× Genomics, Pleasanton, CA, USA) for partitioning samples together with barcoded gel beads in discrete droplets called GEMs ("Gel Beads in Emulsion"). The Chromium System is prepared with the unfixing agent solution added as a separate reagent in generating the GEM containing the sample PBMC and the barcode gel bead. Alternatively, the unfixing agent solution is added to the reservoir containing the suspension of barcoded gel-beads and introduced into the GEMs through the same inlet channel with the gel-beads. Once generated, the GEMs are collected, and a heat incubation step is carried out. The heating step facilitates lysis and release of the cell contents, barcode oligonucleotides, and the RT reaction that results in the cDNA synthesis reaction incorporating the barcodes in the 3' synthons. In incorporating an unfixing agent with the GEMs, the heat incubation step can be extended as necessary to allow for the un-fixing reaction of the DETA that removes the carbamate crosslinks from biomolecules released from the PBMC sample in the GEM.

Example 5: Reversible Fixation with Compound (2a) and the Enzymatic Unfixing Agent, Carboxyesterase (CES)

This example illustrates the use of compound (2a) to fix Jurkats cells, which were then stored for up to 3 days followed by un-fixing using carboxyesterase to yield RNA.

Materials and Methods

A. Preparation of Stock Solutions:

The fixative of compound (2a), was prepared as described in Example 1. A 200 mM stock solution of compound (2a) was prepared in anhydrous DMSO.

Stock solutions of the small molecule unfixing agents, EDA, hydrazine, FosCholine, glycine, and ethanolamine were prepared as follows. EDA, hydrazine, or ethanolamine was diluted in 50 mM Tris buffer, pH 8.3 to make 0.1% w/v solution. Glycine was diluted in 50 mM Tris buffer, pH 8.3 to make 100 mM solution. In some groups, FosCholine was added to provide a final concentration of 2%. In each prepared solution, Qiagen RNAse inhibitor (Qiagen, Cat #129916) was included with a final concentration of 1 unit/μL.

A stock solution of the enzymatic unfixing agent, carboxyesterase ("CES") was prepared as follows. Carboxylesterase 1 or 2 was diluted in 50 mM Tris buffer, pH 8.3 to make final concentration 1 unit/μL. In some groups, FosCholine was added to provide a final concentration of 2%. In each prepared solution, Qiagen RNAse inhibitor (Qiagen, Cat #129916) was included with a final concentration of 1 unit/μL.

B. Fixation of Jurkats:

The final target fixative solutions were prepared by dilution of the stock solution in PBS to provide a concentration of 10 mM. The formulated fixative solutions of compound (2a) were used within 10 mins of formulation to prevent hydrolysis of the reactive imidazole-carboxylates. Fresh Jurkats cells were fixed in 100 μL of the 10 mM fixative solution of compound (2a) for 1 h, then quenched with 10% Fetal Bovine Serum (FBS) in PBS.

C. Unfixing Agent Treatment of Fixed Cells:

At Day 0 and Day 3 time points, cells from the fixed samples were centrifuged at 300 g for 5 min, and supernatant was collected and retained. The pellet of the compound (2a)-fixed cells was un-fixed by incubation with carboxyesterase or the small-molecule unfixing agents as follows. Cell pellets were resuspended and incubated with un-fixing solution containing EDA, hydrazine, ethanolamine, or hydrazine with and without FosCholine at 50° C. for 15 min. Cell pellets were resuspended and incubated with un-fixing solution containing CES 1 or 2 with and without FosCholine at 37° C. for 30 min.

D. Extracted RNA Quantitation

After unfixing agent treatment, the samples were centrifuged at 300 g for 5 min and both pellet (if any) and supernatant were collected. RNA was isolated from the supernatant obtained before treatment with unfixing agent (labeled "storage solution") and the supernatant collected after the unfixing agent treatment (labeled "supernatant") was isolated using the RNAeasy MinElute Cleanup Kit (Qiagen, Cat #74204). RNA from the cell pellets obtained after unfixing agent treatment ("pellet") was isolated using the RNAeasy Plus Mini Kit (Qiagen, Cat #74134). RNA isolated was evaluated for mass recovery and quality (Qubit or Tapestation respectively).

Results: As shown in Table 4, use of the enzymatic unfixing agent, carboxyesterase resulted in much higher RNA recovery from cells fixed with compound (2a) (relative to Fresh cells) than other small molecule unfixing agents, including EDA, hydrazine, FosCholine, glycine, and ethanolamine. Indeed, the total RNA recovered was comparable to the amount recovered from fresh cells that were not fixed.

TABLE 4

| Sample | Unfixing Agent Treatment | Total Recovered RNA (ng) |
|---|---|---|
| Fresh | | 1237.5 |
| Fixed | None | 84.2 |
| Fixed | 0.1% EDA | 147.2 |
| Fixed | 0.1% EDA + 2% FosCholine | 97.7 |
| Fixed | 0.1% hydrazine | 242.6 |
| Fixed | 0.1% hydrazine + 2% FosCholine | 223.1 |
| Fixed | 100 mM glycine | 136.4 |
| Fixed | 100 mM glycine + 2% FosCholine | 391.5 |
| Fixed | 0.1% ethanolamine | 232.2 |
| Fixed | 0.1% ethanolamine + 2% FosCholine | 75.9 |
| Fixed | 1 unit/μL CES1 | 857.3 |
| Fixed | 1 unit/μl CES 1 + 2% FosCholine | 1458.0 |

TABLE 4-continued

| Sample | Unfixing Agent Treatment | Total Recovered RNA (ng) |
|---|---|---|
| Fixed | 1 unit/μL CES 2 | 316.34 |
| Fixed | 1 unit/μl CES 2 + 2% FosCholine | 0 |

Example 6: Recovery of High Quality RNA from Cells Fixed with Compound (2a) without Use of an Unfixing Agent This example illustrates the use of compound (2a) to fix Jurkats cells, which are then stored for up to 3 days in a storage buffer solution, lysed to extract RNA, without the use of an unfixing agent, and 3'-sequenced to determine quality of the extracted RNA.

Materials and Methods

A. Preparation of Stock Solutions:

A stock solution of the fixative of compound (2a), was prepared as described in Example 5.

Storage buffers solutions of sucrose, SSC, and BSA in PBS solutions were prepared at the following concentrations. The CellCover storage buffer solution was obtained from Anacyte Laboratories. The 50% sucrose storage buffer solution was prepared by dissolving sucrose in PBS to provide a final concentration of 50% w/v. The 20×SSC storage buffer solution was purchased from Sigma Aldrich (Sigma Cat #S6639) and diluted 3× in PBS before use. The 0.04% BSA in PBS storage buffer solution was prepared by diluting 10% BSA (Miltenyi Biotec Cat #130-091-376) in PBS to a final concentration of 0.04%.

B. Fixation of Jurkats:

Fixative solutions were prepared by dilution of the compound (2a) stock solution in PBS to provide a concentration of 10 mM compound (2a). The formulated fixative solutions of compound (2a) were used within 10 mins of formulation to prevent hydrolysis of the reactive imidazole-carboxylates. Fresh Jurkats cells were fixed in 100 μL of the 10 mM fixative solution of compound (2a) for 1 h, then quenched with 10% Fetal Bovine Serum (FBS) in PBS. The fixed cells were centrifuged at 300 g for 5 min to remove supernatant and then resuspended in 100 μL of storage buffer solution selected from CellCover, 50% sucrose, 3×SSC, or 0.04% BSA in PBS, and stored at 4° C. for 3 days.

C. Single Cell 3' Gene Expression Analysis

The fixed cells in storage buffer solutions were centrifuged at 300 g for 5 min to remove supernatant then resuspended in 100 μL PBS. The resuspended cells were then processed and sequenced according to the 10× Genomics Single Cell Gene Expression protocol (10× Genomics, Pleasanton, CA, USA).

Results: As shown by the results in Table 5, Jurkats cells fixed with compound (2a), stored for 3 days at 4° C. in 3×SSC or 50% sucrose storage buffer solution, followed by gene expression sample preparation using the 10× Genomics Single Cell Gene Expression protocol, provide high quality gene expression data comparable to data obtained from fresh cells. Significantly, the Pearson's Correlation (R2) between the Day 0 fresh cells and the Day 3 compound (2a)-fixed cells in SSC or sucrose storage buffer was 0.918 and 0.897, respectively. It is also surprising that the expression protocol did not include unfixing agent, and only a lysis agent. The ability to obtain high quality gene expression data from the fixed cells without the use of an unfixing agent indicates that treatment of cells with the fixing reagent of compound (2a) results in preferential fixation of cellular proteins that cause cellular degradation with a substantial amount of mRNA remaining unfixed yet preserved.

TABLE 5

| Sample | Fraction of Reads Total | Fraction of Reads Usable | GRCh38 Median Genes per Cell | Pearson's Correlation ($R^2$) of Gene Expression w/Fresh Cells |
|---|---|---|---|---|
| Fresh Cells | | | | |
| Day 0 | 68.3% | 41.7% | 2444 | N/A |
| Day 3 + CellCover | 80.5% | 30.6% | 591 | 0.733 |
| Day 3 + PBS | 29.9% | 14.4% | 907 | 0.750 |
| Day 3 + sucrose | 18.4% | 8.5% | 693 | 0.781 |
| Fixed Cells | | | | |
| Day 0 | 81.3% | 42.6% | 1937 | 0.819 |
| Day 3 + CellCover | 72.1% | 9.7% | 1054 | 0.765 |
| Day 3 + PBS | 57.3% | 17.3% | 1108 | 0.834 |
| Day 3 + SSC | 67.3% | 31.4% | 1877 | 0.918 |
| Day 3 + sucrose | 70.2% | 26.6% | 1797 | 0.897 |

Example 7: Recovery of High Quality RNA from Cells Fixed with Compound (2a) and Un-Fixed with CES and Hydrazine This example illustrates the use of compound (2a) to fix PBMCs, which are then stored for up to 3 days in a storage buffer solution, un-fixed with a mixture of CES and hydrazine, and then 3'-sequenced to determine quality of the extracted RNA.

Materials and Methods

A. Preparation of Stock Solutions:

The fixative of compound (2a), was prepared as described in Example 1. A 200 mM stock solution of compound (2a) was prepared in anhydrous DMSO.

A stock solution of the enzymatic unfixing agent, carboxyesterase ("CES") was obtained from Creative Biomart (Cat #CES1-29351TH) with a concentration of 20 ng/μL.

A stock solution of the small molecule unfixing agent, hydrazine was prepared by diluting hydrazing in 50 mM Tris buffer, pH 8.3 to make 10% w/v solution.

B. Storage Buffer Solution

A storage buffer solution of 0.04% BSA and 5% Superase in PBS was prepared by dissolving RNase free BSA (Cat #B6917; Sigma-Aldrich) in PBS to a final concentration of 0.04%. Superase (Cat #AM2694; Thermo Fisher Scientific) then was added to a concentration of 5%.

C. Fixation of PBMCs

Fixative solutions were prepared by dilution of the compound (2a) stock solution in PBS to provide a concentration of 10 mM or 20 mM compound (2a). The formulated fixative solutions of compound (2a) were used within 10 mins of formulation to prevent hydrolysis of the reactive imidazole-carboxylates. Fresh PBMCs were fixed in 100 μL of the 10 mM or 20 mM fixative solution of compound (2a) for 1 h, then quenched with 3% RNase BSA in PBS. The fixed cells were centrifuged at 300 g for 5 min to remove supernatant and then resuspended in 100 μL of storage buffer solution of 0.04% BSA in PBS with 5% Superase at 4° C. for 3 days.

D. Partitioning and Single Cell 3' Gene Expression Analysis

At Day 0 and Day 3 time points, cells from Fresh and Fixed samples were collected, counted, and suspended into the Single Cell 3'V3 protocol standard master mix used with the Chromium System (10× Genomics, Pleasanton, CA, USA). CES was added to the same master mix to make the final concentration 0.01 ng/μL. Meanwhile, hydrazine was added to barcoded gel beads (10× Genomics, Pleasanton, CA, USA) to make the final w/v concentration 0.1%. Both master mix and gel beads were loaded into the Chromium System (10× Genomics, Pleasanton, CA, USA) for partitioning samples together with barcoded gel beads in discrete droplets called GEMs ("Gel Beads in Emulsion"). Once generated, the GEMs are collected, and a heat incubation step is carried out. The heating step facilitates release of the cell contents and RNA, capture of RNA by barcode oligonucleotides, and the reverse-transcription (RT) reaction that results in cDNA synthesis incorporating the barcodes in the 3' synthons.

Determination and mapping of PBMC cell types present in the samples was performed by automated meta-analysis of cell clusters identified using differentially expressed marker gene expression. PBMC cell type composition was identified by an automated script that quantifies the number and fraction of cell types known to be detected in PBMC samples by categorizing cells based on a combination of differentially expressed known marker genes for each cell type, with unclassified cells going to the undetermined category.

Results: As shown by the results in Table 6, PBMCs fixed with 10 mM or 20 mM compound (2a), stored for up to 3 days at 4° C., un-fixed using CES and hydrazine, and then prepared and analyzed using the 10× Genomics Single Cell Gene Expression protocol, provide high quality gene expression data comparable to data obtained from fresh cells. As shown in Table 6, the fixation preserves ~60% UMI counts per cell and more than 90% median gene per cell after 3 days. Additionally, the Pearson's Correlation (R2) between the Day 0 fresh cells and the Day 3 compound (2a)-fixed cells, respectively.

TABLE 6

| Sample | Relative Median UMI per Cell | Relative Median Genes per Cell | GRCh38 Median Genes per Cell | Pearson's Correlation ($R^2$) of Gene Expression w/Fresh Cells |
|---|---|---|---|---|
| Fresh Cells | | | | |
| Day 0 | n/a | n/a | 1800 | n/a |
| Day 3 | 32% | 47% | 849 | 0.85 |
| 10 mM (2a) Fixed Cells | | | | |
| Day 0 | 77% | 100% | 1798 | 0.92 |
| Day 3 | 51% | 83% | 1499 | 0.94 |
| 20 mM (2a) Fixed Cells | | | | |
| Day 0 | 53% | 91% | 1635 | 0.90 |
| Day 3 | 56% | 91% | 1641 | 0.88 |

Figure 7:
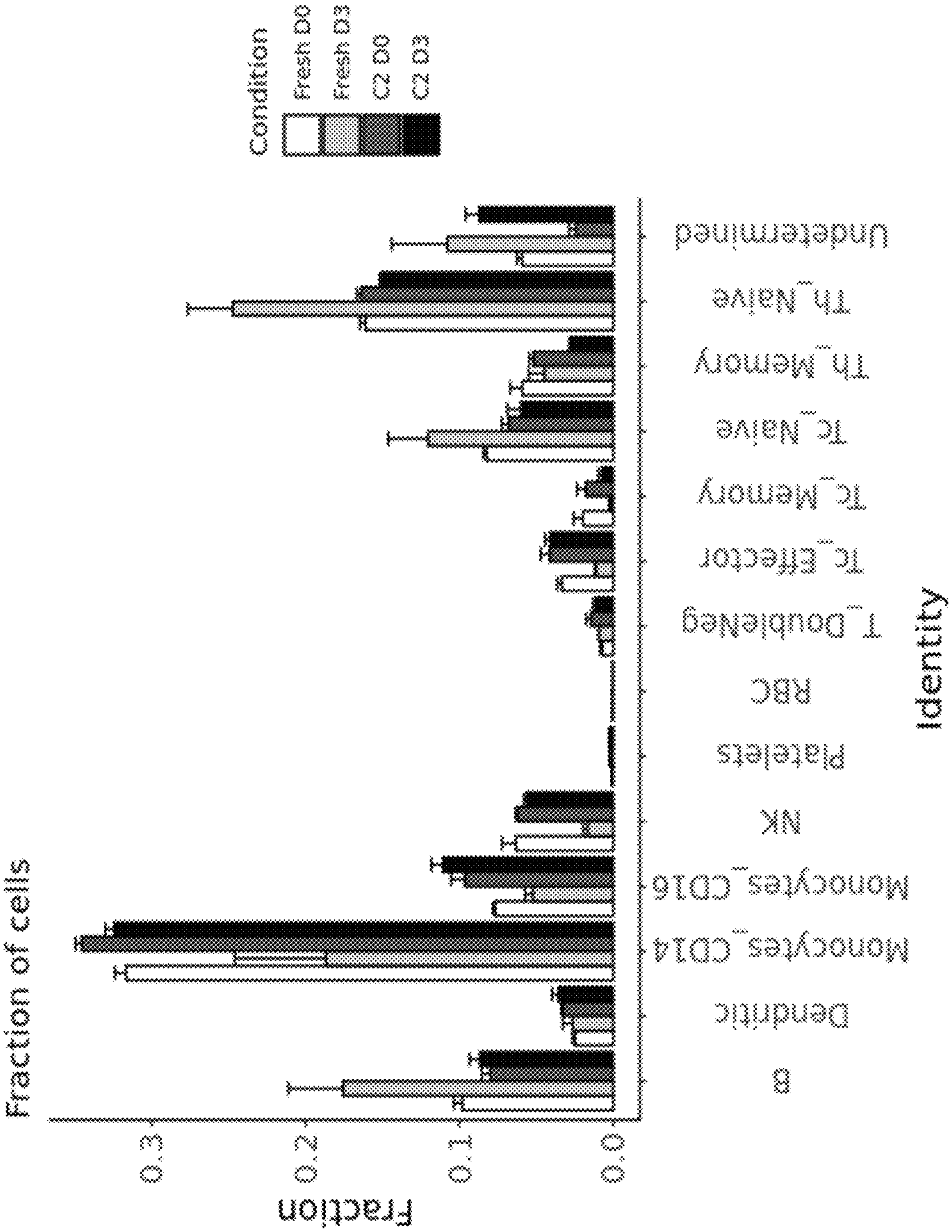
FIG. 7 depicts plots of cell counting of different PBMC cell types found in fresh cells as compared to cells fixed with compound (2a), stored for 3 days, and then subjected to the un-fixing treatment with CES and hydrazine, as described in Example 7.

Additionally, as shown by the plot depicted in FIG. 7, cell counting was carried out to determine the proportion of different PBMC cell types found in the Fresh PBMCs as compared to the PBMCs fixed with compound (2a), stored, and then subjected to the un-fixing treatment of CES and hydrazine. It was observed that the proportions of B cells, T cells, monocyte cells, and undetermined cell populations found in the Fresh cell sample was similar to the proportions found in the fixed cell samples stored for 3 days then subjected to the un-fixing treatment. These comparative PBMC cell counting results indicate that fixation storage and then unfixing of cells using compounds and methods of the present disclosure can be used to analyze relatively cell populations from fixed and stored samples in a droplet-based assay.

The ability to obtain high quality gene expression data from the PBMCs fixed with compound (2a) and un-fixed using CES and hydrazine indicates RNA information in PBMCs can be preserved and retrieved with high efficiency using compound (2a) and the un-fixing conditions described above.

While the foregoing disclosure of the present disclosure has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the disclosure are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

What is claimed is:

1. A method for preparing a biological sample comprising contacting the sample with a first fixing reagent composition comprising:

a compound of formula (I)

(I)

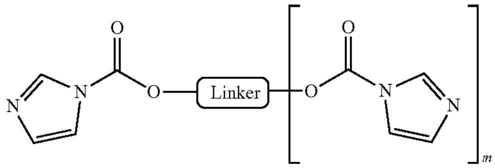

wherein, "Linker" is a linear alkane moiety of 2-24 carbons; a linear alkane moiety of 2-24 carbons comprising a disulfide bond; or a linear alkane moiety of 2-24 carbons substituted with —OR, wherein R is selected from —H, —O(CO)—$CH_3$, and —O(CO)— imidazole; and m is 1 to 12; and a carrier.

2. The method of claim 1, wherein the compound of formula (I) is a compound of formula (II)
(II)
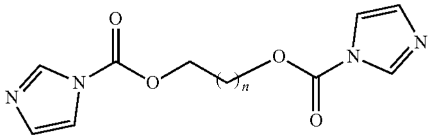
wherein n is 1 to 13.
3. The method of claim 2, wherein the compound of formula (II) is selected from compounds (2a)-(2k)
(2a)
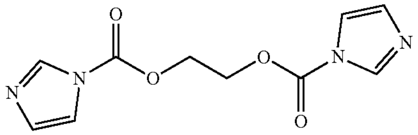
(2b)
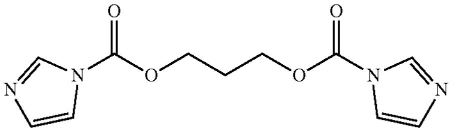
(2c)
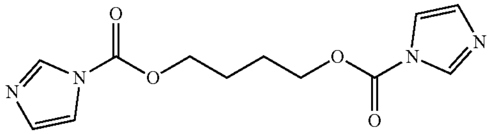
(2d)
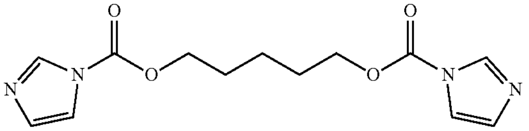
(2e)
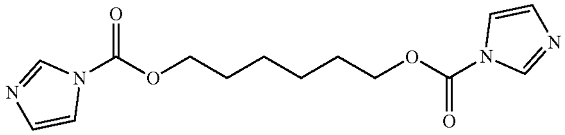
(2f)
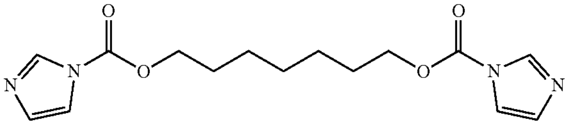
(2g)
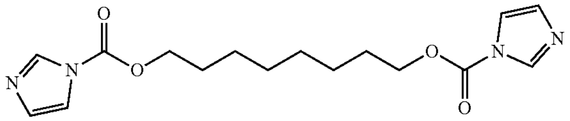
(2h)
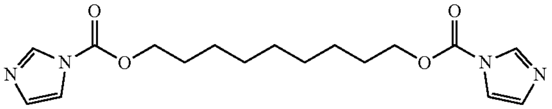
(2i)
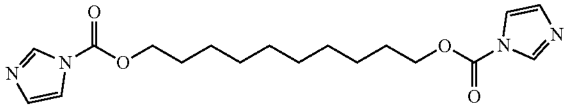
(2j)
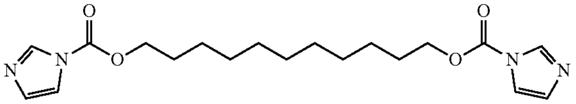
(2k)
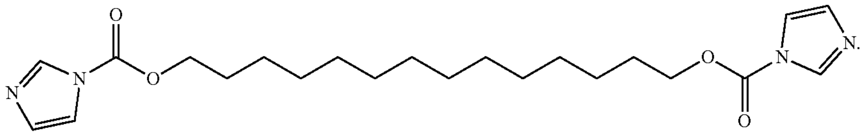
4. The method of claim 1, wherein the compound of formula (I) is a compound of formula (IV)
(IV)
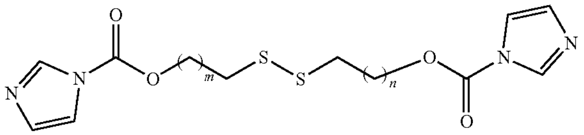
wherein m is 1 to 11, and n is 1 to 11.

5. The method of claim 4, wherein the compound of formula (IV) is selected from compounds (4a)-(4d)

(4a)

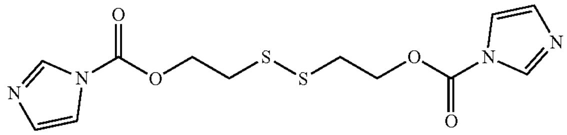

(4b)

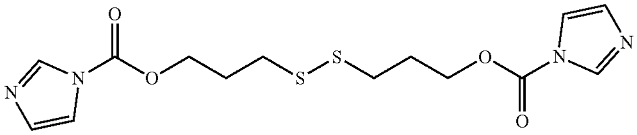

(4c)

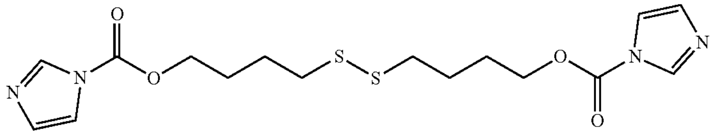

(4d)

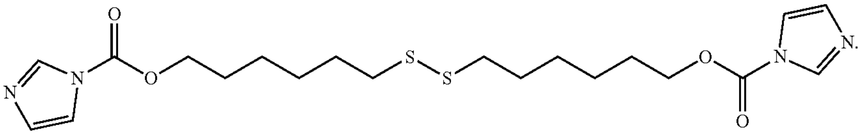

6. The method of claim 1, wherein the compound of formula (I) is compound of formula (V)

(V)

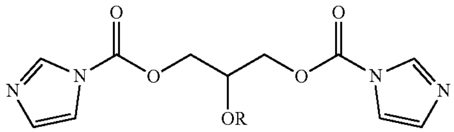

wherein R is selected from —H, —O(CO)—$CH_3$, and —O(CO)— imidazole.

7. The method of claim 6, wherein the compound of formula (V) is selected from compounds (5a)-(5c)

(5a)

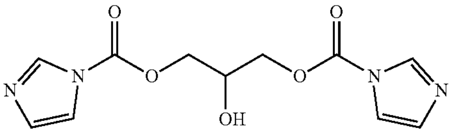

(5b)

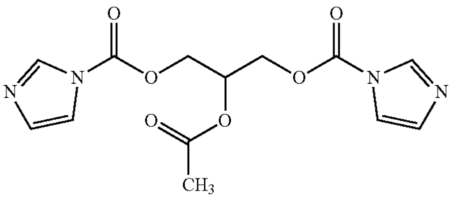

-continued (5c)

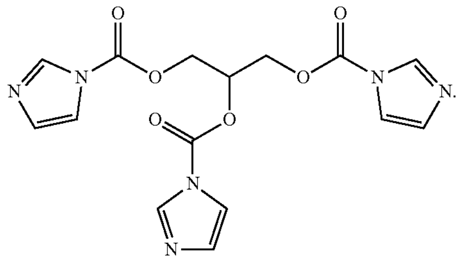

8. The method of claim 1, wherein the first fixing reagent composition comprises:

(a) the compound of formula (I) at a concentration of 5 mM to 50 mM; and (b) DMSO at a concentration of 2.5% to 5%.

9. The method of claim 1, wherein the method further comprises contacting the sample with a second fixing reagent, wherein the second fixing reagent comprises:

i) paraformaldehyde;

ii) a compound of formula (III)

(III)

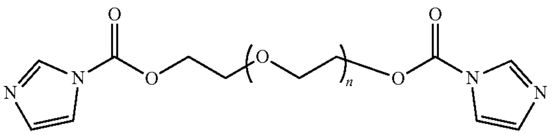

wherein n is 1 to 12; or iii) a compound of formula (V)

(V)

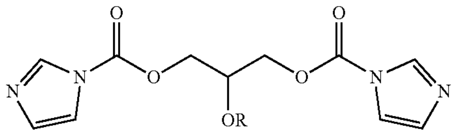

wherein R is selected from —H, —O(CO)—$CH_3$, and —O(CO)— imidazole.

10. The method of claim 1, wherein the method further comprises contacting the sample with a lysis agent and/or an unfixing agent, wherein the lysis agent comprises a compound capable of cleaving a carbamate bond or a compound capable of cleaving a disulfide bond and the unfixing agent comprises a compound capable of reversing paraformaldehyde fixation, wherein:

the compound capable of cleaving a carbamate bond is DETA, EDA, hydrazine monohydrate, a carboxyesterase, or a combination thereof;

the compound capable of cleaving a disulfide bond is DTT; and the compound capable of reversing paraformaldehyde fixation is selected from any one of compounds (7a)-(7o)

(7a)

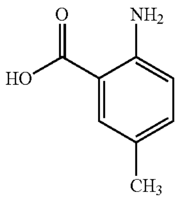

(7b)

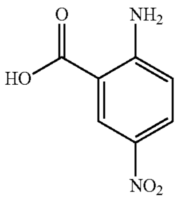

(7c)

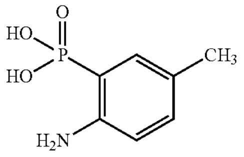

(7d)

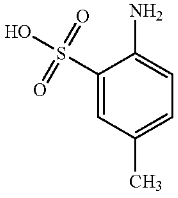

-continued (7e)

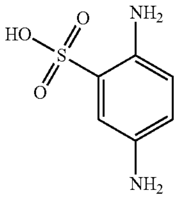

(7f)

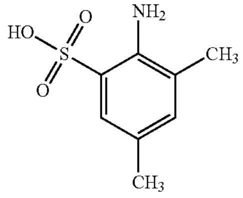

(7g)

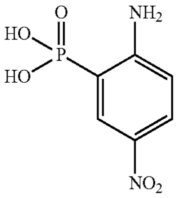

(7h)

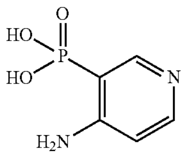

(7i)

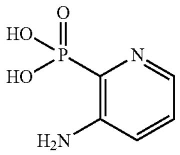

(7j)

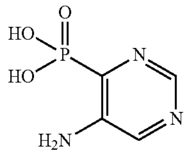

(7k)

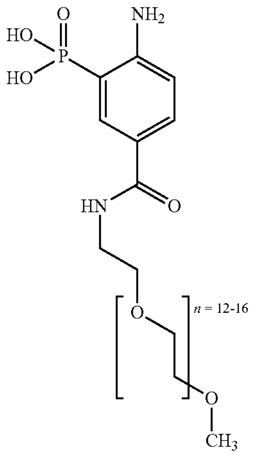

-continued
(7l)
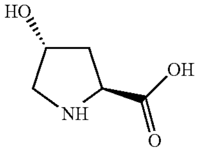
(7m)
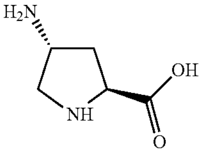
(7n)
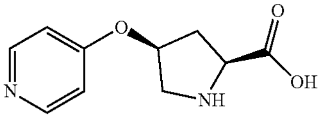
(7o)
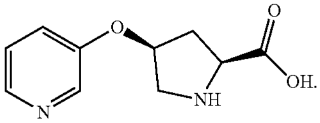
11. The method of claim 1, wherein the biological sample is a tissue sample.
12. The method of claim 5, wherein the compound of formula (IV) is compound (4a).
* * * * *